US008394771B1

(12) United States Patent
Fang et al.

(10) Patent No.: US 8,394,771 B1
(45) Date of Patent: Mar. 12, 2013

(54) MULTIMERIC PROTEINS AND METHODS OF MAKING AND USING SAME

(75) Inventors: Fang Fang, San Diego, CA (US); Guang-Xiang Luo, San Diego, CA (US); Lori Allison Kohlstaedt, La Jolla, CA (US); Catherine Helen Charles, Encinitas, CA (US)

(73) Assignee: Perlan Therapeutics, Inc., San Diego, CA (US)

( * ) Notice: Subject to any disclaimer, the term of this patent is extended or adjusted under 35 U.S.C. 154(b) by 186 days.

(21) Appl. No.: 11/866,960

(22) Filed: Oct. 3, 2007

Related U.S. Application Data

(63) Continuation of application No. 10/199,957, filed on Jul. 19, 2002, now abandoned.

(60) Provisional application No. 60/306,746, filed on Jul. 19, 2001, provisional application No. 60/335,425, filed on Nov. 30, 2001.

(51) Int. Cl.
*A61K 38/17* (2006.01)
*C12P 21/04* (2006.01)
*C07K 14/435* (2006.01)

(52) U.S. Cl. ...... 514/21.2; 514/21.3; 530/350; 435/69.7

(58) Field of Classification Search ........................ None
See application file for complete search history.

(56) References Cited

U.S. PATENT DOCUMENTS

| | | | |
|---|---|---|---|
| 4,522,811 A | 6/1985 | Eppstein et al. |
| 4,698,420 A | 10/1987 | Urnovitz |
| 4,844,904 A | 7/1989 | Hamaguchi et al. |
| 4,863,740 A | 9/1989 | Kissel et al. |
| 4,946,778 A | 8/1990 | Ladner et al. |
| 4,975,282 A | 12/1990 | Cullis et al. |
| 5,000,959 A | 3/1991 | Iga et al. |
| 5,077,195 A | 12/1991 | Blalock et al. |
| 5,081,584 A | 1/1992 | Omichinski |
| 5,223,396 A | 6/1993 | Rothlein et al. |
| 5,223,409 A | 6/1993 | Ladner |
| 5,225,539 A | 7/1993 | Winter |
| 5,260,203 A | 11/1993 | Ladner et al. |
| 5,324,510 A | 6/1994 | Wegner et al. |
| 5,330,101 A | 7/1994 | Turner et al. |
| 5,455,030 A | 10/1995 | Ladner et al. |
| 5,459,127 A | 10/1995 | Felgner et al. |
| 5,475,091 A | 12/1995 | Springer et al. |
| 5,491,074 A | 2/1996 | Aldwin et al. |
| 5,501,979 A | 3/1996 | Geller et al. |
| 5,561,063 A | 10/1996 | Hock et al. |
| 5,565,550 A | 10/1996 | Springer et al. |
| 5,573,925 A | 11/1996 | Halazonetis |
| 5,582,996 A | 12/1996 | Curtis |
| 5,585,089 A | 12/1996 | Queen et al. |
| 5,604,090 A | 2/1997 | Alexander et al. |
| 5,624,820 A | 4/1997 | Cooper |
| 5,639,641 A | 6/1997 | Pedersen et al. |
| 5,656,332 A | 8/1997 | Saito et al. |
| 5,665,577 A | 9/1997 | Sodroski et al. |
| 5,674,703 A | 10/1997 | Woo et al. |
| 5,693,508 A | 12/1997 | Chang |
| 5,693,761 A | 12/1997 | Queen et al. |
| 5,693,762 A | 12/1997 | Queen et al. |
| 5,700,470 A | 12/1997 | Saito et al. |
| 5,716,805 A | 2/1998 | Srinivasan et al. |
| 5,719,054 A | 2/1998 | Boursnell et al. |
| 5,721,340 A | 2/1998 | Halazonetis |
| 5,723,286 A | 3/1998 | Dower et al. |
| 5,731,168 A | 3/1998 | Carter et al. |
| 5,731,172 A | 3/1998 | Saito et al. |
| 5,763,733 A | 6/1998 | Whitlow et al. |
| 5,786,340 A | 7/1998 | Henning et al. |
| 5,807,706 A | 9/1998 | Carter et al. |
| 5,821,123 A | 10/1998 | Studnicka |
| 5,821,235 A | 10/1998 | Henning et al. |
| 5,821,333 A | 10/1998 | Carter et al. |
| 5,821,337 A | 10/1998 | Carter et al. |
| 5,837,242 A | 11/1998 | Holliger et al. |
| 5,856,456 A | 1/1999 | Whitlow et al. |
| 5,861,397 A | 1/1999 | Wheeler |
| 5,869,620 A | 2/1999 | Whitlow et al. |
| 5,910,573 A | 6/1999 | Pluckthun et al. |
| 5,928,944 A | 7/1999 | Seth et al. |
| 5,932,448 A | 8/1999 | Tso et al. |
| 5,942,433 A | 8/1999 | Vinson et al. |
| 5,965,712 A | 10/1999 | Conrad |
| 6,013,516 A | 1/2000 | Verma et al. |
| 6,025,165 A | 2/2000 | Whitlow et al. |
| 6,027,725 A | 2/2000 | Whitlow et al. |
| 6,071,515 A | 6/2000 | Mezes et al. |
| 6,096,291 A | 8/2000 | Betbeder et al. |
| 6,110,456 A | 8/2000 | During |
| 6,121,424 A | 9/2000 | Whitlow et al. |
| 6,129,914 A | 10/2000 | Weiner et al. |
| 6,190,886 B1 | 2/2001 | Hoppe |
| 6,218,513 B1 | 4/2001 | Anthony-Cahill et al. |
| 6,307,026 B1 | 10/2001 | King et al. |
| 6,329,507 B1 | 12/2001 | Mezes et al. |
| 6,329,511 B1 | 12/2001 | Vasquez et al. |
| 6,800,735 B2 * | 10/2004 | Whitty et al. ............... 530/351 |
| 7,696,324 B2 | 4/2010 | Fang et al. |
| 2002/0165153 A1 | 11/2002 | Angel et al. |
| 2003/0035798 A1 | 2/2003 | Fang et al. |
| 2003/0138440 A1 | 7/2003 | Fang et al. |
| 2011/0044976 A1 | 2/2011 | Fang |

(Continued)

FOREIGN PATENT DOCUMENTS

| CA | 2407426 | 11/2001 |
|---|---|---|
| DE | 19815331 A1 | 10/1991 |

(Continued)

OTHER PUBLICATIONS

Fang et al., Antiviral Research, 53(3):pA65 Mar. 2002, Conference/Meeting: Fifteenth International Conference on Antiviral Research, Prague, Czech Republic, Mar. 17-21, 2002.*

(Continued)

*Primary Examiner* — Marianne P Allen
(74) *Attorney, Agent, or Firm* — Jones Day

(57) ABSTRACT

The invention provides multimerization polypeptides capable of conferring formation of multimers when the multimerization polypeptide is linked to a molecule, such as a heterologous polypeptide sequence.

29 Claims, 9 Drawing Sheets

FOREIGN PATENT DOCUMENTS

| | | |
|---|---|---|
| DE | 198 15 331 | 10/1999 |
| EP | 0169146 A2 | 1/1986 |
| EP | 0239400 B1 | 9/1987 |
| EP | 0387701 B1 | 9/1990 |
| EP | 0404003 A2 | 12/1990 |
| EP | 0451216 B1 | 10/1991 |
| EP | 0459577 A2 | 12/1991 |
| EP | 0387701 B1 | 8/1992 |
| EP | 0528931 B1 | 3/1993 |
| EP | 0605522 B1 | 7/1994 |
| EP | 0654085 B1 | 5/1995 |
| EP | 0365837 B1 | 8/1995 |
| EP | 0672142 B1 | 9/1995 |
| EP | 0682040 B1 | 11/1995 |
| EP | 0939127 A2 | 9/1999 |
| EP | 0967277 A2 | 12/1999 |
| EP | 1039931 B1 | 4/2005 |
| JP | 10-101699 | 4/1998 |
| JP | 2005100185 A | 4/2005 |
| WO | WO 88/01649 | 3/1988 |
| WO | WO 90/07861 | 7/1990 |
| WO | WO 91/07418 | 5/1991 |
| WO | WO 91/07493 | 5/1991 |
| WO | WO 91/07494 | 5/1991 |
| WO | WO 91/16927 | 11/1991 |
| WO | WO 91/16928 | 11/1991 |
| WO | WO 92/05266 | 4/1992 |
| WO | WO 92/11018 | 7/1992 |
| WO | WO 92/14829 | 9/1992 |
| WO | WO 92/22653 | 12/1992 |
| WO | WO 93/06213 | 4/1993 |
| WO | WO 93/11161 | 6/1993 |
| WO | WO 93/11162 | 6/1993 |
| WO | WO 93/11794 | 6/1993 |
| WO | WO 93/15210 | 8/1993 |
| WO | WO 93/23434 | 11/1993 |
| WO | WO 94/04679 | 3/1994 |
| WO | WO 94/13804 | 6/1994 |
| WO | WO 94/18318 | 8/1994 |
| WO | WO 94/20078 | 9/1994 |
| WO | WO 95/08577 | 3/1995 |
| WO | WO 95/27736 | 10/1995 |
| WO | WO 96/13583 | 5/1996 |
| WO | WO 96/34015 | 10/1996 |
| WO | WO 96/37621 | 11/1996 |
| WO | WO-97/23631 | 7/1997 |
| WO | WO 97/23631 | 7/1997 |
| WO | WO 98/50431 | 11/1998 |
| WO | WO 99/10510 | 3/1999 |
| WO | WO 99/27964 | 6/1999 |
| WO | WO 99/55911 | 11/1999 |
| WO | WO 00/09073 | 2/2000 |
| WO | WO-00/23472 | 4/2000 |
| WO | WO 01/00814 | 1/2001 |
| WO | WO 01/19842 A1 | 3/2001 |
| WO | WO 03/035696 | 5/2003 |
| WO | WO 03/062370 | 7/2003 |

OTHER PUBLICATIONS

Harbury et al., Science, 262:1401-1407, 1993.*
Pescini et al., Journal of Biological Chemistry, 269(2):1159-1166, 1994.*
Kruif and Logtenberg, Leucine zipper dimerized bivalent and bispecific scFv antibodies from a semi-synthetic antibody phage display library. The Journal of Biological Chemistry, 271(13): 7630-7634, 1996.
Crameri and Suter, Display of biologically active proteins on the surface of filamentous phages: a cDNA cloning system for selection of functional gene products linked to the genetic information responsible for their production. Gene, 137: 69-75, 1993
Kerschaumer et al., Single-chain Fv fusion proteins suitable as coating and detecting reagents ina double antibody sandwich enzyme-linked immunosorbent assay. Analytical Biochemistry, 249:219-227, 1997.
Kalandaze et al., Expression of recombinant HLA-DR2 molecules. The Journal of Biological Chemistry, 271(33): 20156-20162, 1996.
Arndt et al., Helix-stabilized Fv (hsFv) antibody fragments: Substituting the constant domains of a Fab fragment for a heterodimeric coiled-coil domain. Journal of Mol. Biology, 312: 221-228, 2001.
Pluckthun and Pack, New protein engineering approaches to multivalent and bispecific antibody fragments. Immunotechnology, 3:83-105, 1997.
Foote and Winter, "Antibody Framework Residues Affecting the Conformation of the Hypervariable Loops," J. Mol. Biol. 224:487-490 (1992).
PCT International Search Report, dated Sep. 8, 2003 for PCT/US 02/23002.
Ohtomo et al., "Humanization of Mouse ONS-M21 Antibody With the Aid of Hybrid Variable Regions," (1995) Molecular Immunology, vol. 1, No. 6, pp. 407-416.
Mateo et al., "Humanization of a mouse monoclonal antibody that blocks the epidermal growth factor receptor; recovery of antagonistic activity," (1997), Immunotechnology, vol. 3, pp. 71-81.
Nagahira et al., "Humanization of a mouse neutralizing monoclonal antibody against tumor necrosis factor-$\alpha$ (TNF-$\alpha$)," (1999), Journal of Immunological Methods, vol. 222, pp. 83-92.
Saldanha et al., "A single blackmutation in the human kIV framework of a previously unsuccessfully humanized antibody restores the binding activity and increases the secretion in cos cells," (1999). Molecular Immunology, vol. 36, pp, 709-719.
Tempest et al., "Identification of framework residues required to restore antigen binding during reshaping of a monoclonal antibody against the glycoprotein gB of human cytomegalovirus," (1995), Int. J. Biol. Macromol., vol. 17, No. 1, pp. 37-42.
Carter et al., "Humanization of an anti-p185(HER2) antibody for human cancer therapy," (1992), Proc. Natl. Acad. Sci., vol. 89, pp. 4285-4289.
Presta et al., "Humanization of an Antibody Directed Against IgE," (1993), Journal of Immunology, vol. 151, No. 5, pp. 2623-2632.
Padlan (1994) Molecular Immunol. 31: 169-217.
Rudikoff et al., Single amino acid substitution altering antigen-binding specificity. Proc. Natl. Acad. Sci. USA, 1982 vol. 79, pp. 1979-1983.
Fox. J., No Winner against AIDS, Bio/Technology, vol. 12 (Feb. 1994), p. 128.
Ockenhouse et al., Plasmodium falciparum-infected erythrocytes bind ICAM-1 at a site distinct from LFA-1, MAC-1, and Human Rhinovirus. Cell 68 (1), 1992, pp. 63-69.
Cruse et al., Illustrated dictionary of immunology, $2^{nd}$ edition. CRC Press, 2003, pp. 341.
Bastiani et al., Host cell-dependent alterations in envelope components of human immunodeficiency virus type 1 virions. Journal of Virology, May 1997, pp. 3444-3450.
Fahey et al., "A Status of immune-based therapies in HIV infection and AIDS", Clinical and Experimental Immunology, vol. 88 (1992), pp. 1-5.
Crowe et al., Vaccine, 2002; 20:S32-S37.
Padlan (1991) Molecular Immunol. 28: 489-498.
Charles et al., Prevention of Human Rhinovirus Infection by Multivalent Fab Molecules Directed Against ICAM-1. Antimicrobial Agents and Chemotherapy, 2003, 1503-1508.
Behera et al., Blocking intercellular adhesion molecule-1 on human epithelial cells decreases respiratory syncytial virus infection. Biochemical and biophysical research communications 280(1):188-195, Jan. 12, 2001.
Terskikh et al., "Peptabody": A new type of high avidity binding protein. Proc. Natl. Acad. Sci. USA 94:1663-1668, 1997.
Hodits et al., (1995) "An Antibody Fragment from a Phage Display Library Competes for Ligand Binding to the Low Density Lipoprotein Receptor Family and Inhibits Rhinovirus Infection", J. Biol. Chem. 270 (41):24078-24085.
Hofer et al. (1994) "Members of the low density lipoprotein receptor family mediate cell entry of a minor group common cold virus", Proc. Natl. Acad. Sci. USA 91:1839-1842.
Welply et al. (1996) A Peptide Isolated by Phage Display Binds to ICAM-1 and Inhibits Binding to LFA-1 Proteins: Structure, Function, and Genetics 26:262-270.
Karush, F. et al., "Multivalence and affinity of antibody", Int. Arch. Allergy Appl. Immunol. 45(1-2):130-132 (1973).

Pack, Peter et al., "Tetravalent miniantibodies with high avidity assembling in *Escherichia coli*", J. Mol. Biol. 246(1):28-34 (1995).

Kipriyanov et al., Affinity enhancement of recombinant antibody: formation of complexes with multiple valency by a single-chain Fv fragment-core streptavidin fusion. Protein Engineering (1996) vol. 9, No. 2, pp. 203-211.

Lou, Guang X. et al., "Humanization of an anti-ICAM-1 antibody with over 50-fold affinity and functional improvement", Journal of Immunological Methods, 275 (2003) 31-40.

Pestov, D.G. et al., "Genetic selection of growth-inhibitory sequences in mammalian cells", Proceedings of the National Academy of Science, vol. 91, No. 26, Dec. 20, 1994.

Kamtekar, S. et al., "Protein design by binary patterning of polar and nonpolar amino acids", Science, Dec. 10, 1993, vol. 262, No. 5140. pp. 1680-1685.

Holsworth, Daniel D. et al., "Antisense-designed peptides: A comparative study focusing on possible complements to angiotensin II", Peptide Research, vol. 7, No. 4, 1994, pp. 185-193.

Arndt et al., Helix-stabilized Fv (hsFv) antibody fragments: Substituting the constant domains of a Fab fragment for a heterodimeric coiled-coil domain, Journal of Molecular Biology, London GB, vol. 312, No. 1, 2001, pp. 221-228.

Staunton, et al, A cell adhesion molecule, ICAM-1, is the major surface receptor for rhinoviruses, Cell, (1989), 56(5):849-853.

Altschul et al., Basic Local Alignment Search Tool, J. Mol. Biol. 215:403-410 (1990).

Bitter et al., Expression and Secretion Vectors for Yeast, Methods in Enzymology, Acad. Press, N.Y., 153:516-544 (1987).

Bitter, Grant A., Heterologous Gene Expression in Yeast, Methods in Enzymology, Acad. Press, N.Y., vol. 152, pp. 673-684 (1987).

Casasnovas, et al, Kinetics and thermodynamics of virus binding to receptor, (1995), J Bio Chem, 270(22):13216-13224.

Chothia et al., Conformations of immunoglobulin hypervariable regions, Nature, 342:877-883 (1989).

Chothia et al., Domain Association in Immunoglobulin Molecules, The Packing of Variable Domains, J. Mol. Biol., 186:651-663 (1985).

Chothia et al., Structural Repertoire of the Human $V_H$ Segments, J. Mol. Biol., 227:799-817 (1992).

Co et al., Chimeric and Humanized Antibodies with Specificity for the CD33 Antigen, J. Immunol., 148:1149-1154(1992).

Co et al., Humanized antibodies for antiviral therapy, Proc. Natl. Acad. Sci. USA 88:2869-2873 (1991).

Colonno, et al, Isolation of a monoclonal antibody that blocks attachment of the major group of human rhinoviruses, J Virol, (1986), 57(1):7-12.

Cone, R.D. And Mulligan, R.C., High-efficiency gene transfer into mammalian cells: Generation of helper-free recombinant retrovirus with broad mammalian host range, Proc. Natl. Acad. Sci. USA, vol. 81, pp. 6349-6353 (1984).

Fabrice Le Gall et al., "-Di-, tri- and tetrameric single chain FV antibody fragments against human CD19: effect of valency on cell binding", FEBS Letters 453 (1999) 164-168.

Fang et al., Viral receptor blockage by multivalent recombinant antibody fusion proteins: inhibiting human Rhinovirus (HRV) infection with CFY196. Journal of Antimicrobial Chemotherapy, 2003, 1-3.

Fitzgerald et al., Total Chemical Synthesis and Catalytic Properties of the Enzyme Enantiomers L- and D-4-Oxalocrotonate Tautomerase, J. Am. Chem. Soc., 117:11075-11080 (1995).

Gram et al., In vitro selection and affinity maturation of antibodies from a naive combinatorial immunoglobulin library, Proc. Natl. Acad. Sci. USA, vol. 89, pp. 3576-3580 (1992).

Harris, Production of humanized monoclonal anitbodies for in vivo imaging and therapy, (1995), Biochemical Society Transactions, 23(4):1035-1038.

Hartman, S. C. and Mulligan, R.C., Two dominant-acting selectable markers for gene transfer studies in mammalian cells, Proc. Natl. Acad. Sci. USA, vol. 85, pp. 8047-8051 (1988).

Hayden et al., "Phase II, Randomized, Double-blind, Placebo-Controlled Studies of Ruprintrivir Nasal Spray 2-Percent Suspension for Prevention and Treatment of Experimentally Induced Rhinovirus Colds in Healthy Volunteers", Antimicrobial Agents and Chemotherapy, Dec. 2003, vol. 47(12), p. 3907-3916.

Hayden, et al, Modification of experimental rhinovirus colds by receptor blockade, (1998), Antiviral Research, 9:233-247.

Hurle, et al, Protein engineering techniques for antibody humanization, (1994), Current Opinion in Biotechnology, 5:428-433.

Inbar et al., Localization of Antibody-Combining Sites within the Variable Portions of Heavy and Light Chains, Proc. Natl. Acad. Sci. USA, vol. 69, No. 9, pp. 2659-2662 (1972).

Jedrzejas, et al, Structure of a monoclonal anti-ICAM-1 antibody R6.5 Fab fragment at 2.8 A resolution, Acta Crystallogr D Biol Crystallogr. May 1995 1:51(Pt 3):380-5.

Jones et al., Replacing the complementarity-determining regions in a human antibody with those from a mouse, Nature, 321:522-525 (1986).

Kaiser et al., "In vitro activity of pleconaril and AG7088 against selected serotypes and clinical isolates of human rhinoviruses", Antiviral Research 47 (2000) 215-220.

Kay et al., Evidence or gene transfer and expression of factor IX in haemophilia B patients treated with an AAV vector, Nature Genetics, 24:257-261 (2000).

Le Calvez et al., Review: Biochemical prevention and treatment of viral infections—A new paradigm in medicine for infectious diseases. Virology Journal, 2004, vol. I, 1-6.

Lineberger, et al, Antibodies that block rhinovirus attachment map to domain 1 of the major group receptor, J Virol, (1990), 64(6):2582-2587.

Lowy et al., Isolation of Transforming DNA: Cloning the Hamster aprt Gene, Cell, 22:817-823 (1980).

Nakai et al., Adeno-Associated Viral Vector-Mediated Gene Transfer of Human Blood Coagulation Factor IX Into Mouse Liver, Blood 91:4600-4607 (1998).

Pack et al., Improved Bivalent Miniantibodies, with Identical Avidity as Whole Antibodies, Produced by High Cell Density Fermentation of *Escherichia coli*, Bio/Technology, 11:1271-1277 (1993).

Queen et al., A humanized antibody that binds to the interleukin 2 receptor, Proc. Natl. Acad. Sci. USA, vol. 86, pp. 10029-10033 (1989).

Reichmann et al., Reshaping human antibodies for therapy, Nature, 332:323-327 (1988).

Rothstein, Rodney, Chapter 3, DNA cloning, vol. II, A Practical Approach, IRL Press, Washington, D.C., pp. 1-66 (1986) Glover, D.M. ed.

Sandhu, Jasbir S., Protein Engineering of Antibodies, Critical Reviews in Biotechnology, 12:5, 437-462 (1992).

Sarver et al., Bovine Papilloma Virus Deoxyribonucleic Acid: a Novel Eucaryotic Cloning Vector, Molecular and Cellular Biology, 16:486-496 (1981).

Schneider, et al, Safety, pharmacokinetics and biological activity of enlimomab (anti-ICAM-1 antibody): an open-label, dose escalation study in patients hospitalized for acute stroke, Eur Neurol,(1998), 40(2):78-83.

Staunton, et al, The arrangement of the immunoglobulin-like domains of ICAM-1 and the binding sited for LFA-1 and rhinovirus, (1990), Cell, 61:243-254.

Szybalska, E.H. and Szybalski, W., Genetics of Human Cell Lines, IV. DNA-Mediated Heritable Transformation of a Biochemical Trait, Proc. Natl. Acad. Sci. USA, vol. 48, pp. 2026-2034 (1962).

Verhoeyen et al., Reshaping Human Antibodies: Grafting an Antilysozyme Activity, Science, 239:1534-1536 (1988).

Vuorte, et al, Anti-ICAM-1 monoclonal antibody R6.5 (Enlimomab) promotes activation of neutrophils in whole blood, J Immunol, (1999), 162(4):2353-7.

Winter, et al., Humanized antibodies, (1993), Immunology Today, 14(6):243-246.

\* cited by examiner

A

B

```
                            SEQUENCE LISTING

<160> NUMBER OF SEQ ID NOS: 164

<210> SEQ ID NO 1
<211> LENGTH: 31
<212> TYPE: PRT
<213> ORGANISM: Artificial Sequence
<220> FEATURE:
<223> OTHER INFORMATION: Synthetic polypeptide

<400> SEQUENCE: 1

Leu Ser Ser Ile Glu Lys Lys Leu Glu Glu Ile Thr Ser Gln Leu Ile
1               5                   10                  15

Gln Ile Ser Asn Glu Leu Thr Leu Ile Arg Asn Glu Leu Ala Gln
            20                  25                  30

<210> SEQ ID NO 2
<211> LENGTH: 31
<212> TYPE: PRT
<213> ORGANISM: Artificial Sequence
<220> FEATURE:
<223> OTHER INFORMATION: Synthetic polypeptide

<400> SEQUENCE: 2

Leu Ser Ser Ile Glu Lys Lys Leu Glu Glu Ile Thr Ser Gln Leu Ile
1               5                   10                  15

Gln Ile Arg Asn Glu Leu Thr Leu Ile Arg Asn Glu Leu Ala Gln
            20                  25                  30

<210> SEQ ID NO 3
<211> LENGTH: 31
<212> TYPE: PRT
<213> ORGANISM: Artificial Sequence
<220> FEATURE:
<223> OTHER INFORMATION: Synthetic polypeptide

<400> SEQUENCE: 3

Leu Ser Ser Ile Glu Lys Lys Leu Glu Glu Ile Thr Ser Gln Leu Gln
1               5                   10                  15

Gln Ile Arg Asn Glu Leu Thr Leu Ile Arg Asn Glu Leu Ala Gln
            20                  25                  30

<210> SEQ ID NO 4
<211> LENGTH: 31
<212> TYPE: PRT
<213> ORGANISM: Artificial Sequence
<220> FEATURE:
<223> OTHER INFORMATION: Synthetic polypeptide

<400> SEQUENCE: 4

Leu Ser Ser Leu Glu Lys Lys Leu Glu Glu Leu Thr Ser Gln Leu Ile
1               5                   10                  15

Gln Leu Arg Asn Glu Leu Thr Leu Leu Arg Asn Glu Leu Ala Gln
            20                  25                  30

<210> SEQ ID NO 5
<211> LENGTH: 31
```

```
<212> TYPE: PRT
<213> ORGANISM: Artificial Sequence
<220> FEATURE:
<223> OTHER INFORMATION: Synthetic polypeptide

<400> SEQUENCE: 5

Ile Ser Ser Leu Glu Lys Lys Ile Glu Glu Leu Thr Ser Gln Ile Gln
1               5                   10                  15

Gln Leu Arg Asn Glu Ile Thr Leu Leu Arg Asn Glu Ile Ala Gln
            20                  25                  30

<210> SEQ ID NO 6
<211> LENGTH: 31
<212> TYPE: PRT
<213> ORGANISM: Artificial Sequence
<220> FEATURE:
<223> OTHER INFORMATION: Synthetic polypeptide

<400> SEQUENCE: 6

Ile Ser Ser Ile Glu Lys Lys Ile Glu Glu Ile Thr Ser Gln Ile Ile
1               5                   10                  15

Gln Ile Arg Asn Glu Ile Thr Leu Ile Arg Asn Glu Ile Ala Gln
            20                  25                  30

<210> SEQ ID NO 7
<211> LENGTH: 31
<212> TYPE: PRT
<213> ORGANISM: Artificial Sequence
<220> FEATURE:
<223> OTHER INFORMATION: Synthetic polypeptide

<400> SEQUENCE: 7

Val Ser Ser Leu Glu Lys Lys Val Glu Glu Leu Thr Ser Gln Val Ile
1               5                   10                  15

Gln Leu Arg Asn Glu Val Thr Leu Leu Arg Asn Glu Val Ala Gln
            20                  25                  30

<210> SEQ ID NO 8
<211> LENGTH: 31
<212> TYPE: PRT
<213> ORGANISM: Artificial Sequence
<220> FEATURE:
<223> OTHER INFORMATION: Synthetic polypeptide

<400> SEQUENCE: 8

Val Ser Ser Leu Glu Lys Lys Ala Glu Glu Leu Thr Ser Gln Asn Ile
1               5                   10                  15

Gln Leu Ser Asn Glu Val Thr Leu Leu Arg Asn Glu Val Ala Gln
            20                  25                  30

<210> SEQ ID NO 9
<211> LENGTH: 31
<212> TYPE: PRT
<213> ORGANISM: Artificial Sequence
<220> FEATURE:
<223> OTHER INFORMATION: Synthetic polypeptide

<400> SEQUENCE: 9

Leu Lys Ser Ile Glu Asn Arg Leu Ala Val Ile Glu Asn Gln Leu Lys
1               5                   10                  15

Thr Ile Ile Glu Glu Leu Lys Thr Ile Lys Asp Leu Leu Ser Asn
            20                  25                  30

<210> SEQ ID NO 10
<211> LENGTH: 31
```

```
<212> TYPE: PRT
<213> ORGANISM: Artificial Sequence
<220> FEATURE:
<223> OTHER INFORMATION: Synthetic polypeptide

<400> SEQUENCE: 10

Leu Lys Ser Leu Glu Asn Arg Leu Ala Val Leu Glu Asn Gln Leu Lys
1               5                   10                  15

Thr Leu Ile Glu Glu Leu Lys Thr Leu Lys Asp Leu Leu Ser Asn
            20                  25                  30

<210> SEQ ID NO 11
<211> LENGTH: 31
<212> TYPE: PRT
<213> ORGANISM: Artificial Sequence
<220> FEATURE:
<223> OTHER INFORMATION: Synthetic polypeptide

<400> SEQUENCE: 11

Ile Lys Ser Leu Glu Asn Arg Ile Ala Val Leu Glu Asn Gln Ile Lys
1               5                   10                  15

Thr Leu Ile Glu Glu Ile Lys Thr Leu Lys Asp Leu Ile Ser Asn
            20                  25                  30

<210> SEQ ID NO 12
<211> LENGTH: 31
<212> TYPE: PRT
<213> ORGANISM: Artificial Sequence
<220> FEATURE:
<223> OTHER INFORMATION: Synthetic polypeptide

<400> SEQUENCE: 12

Ile Lys Ser Ile Glu Asn Arg Ile Ala Val Ile Glu Asn Gln Ile Lys
1               5                   10                  15

Thr Ile Ile Glu Glu Ile Lys Thr Ile Lys Asp Leu Ile Ser Asn
            20                  25                  30

<210> SEQ ID NO 13
<211> LENGTH: 31
<212> TYPE: PRT
<213> ORGANISM: Artificial Sequence
<220> FEATURE:
<223> OTHER INFORMATION: Synthetic polypeptide

<400> SEQUENCE: 13

Val Lys Ser Leu Glu Asn Arg Val Ala Val Leu Glu Asn Gln Val Lys
1               5                   10                  15

Thr Leu Ile Glu Glu Val Lys Thr Leu Lys Asp Leu Val Ser Asn
            20                  25                  30

<210> SEQ ID NO 14
<211> LENGTH: 31
<212> TYPE: PRT
<213> ORGANISM: Artificial Sequence
<220> FEATURE:
<223> OTHER INFORMATION: Synthetic polypeptide

<400> SEQUENCE: 14

Leu Lys Ser Val Glu Asn Arg Leu Ala Val Val Glu Asn Gln Leu Lys
1               5                   10                  15

Thr Val Ile Glu Glu Leu Lys Thr Val Lys Asp Leu Leu Ser Asn
            20                  25                  30

<210> SEQ ID NO 15
<211> LENGTH: 31
```

```
<212> TYPE: PRT
<213> ORGANISM: Artificial Sequence
<220> FEATURE:
<223> OTHER INFORMATION: Synthetic polypeptide

<400> SEQUENCE: 15

Leu Ala Arg Ile Glu Glu Lys Leu Lys Thr Ile Lys Ala Gln Leu Ser
1               5                   10                  15

Glu Ile Ala Ser Thr Leu Asn Met Ile Arg Glu Gln Leu Ala Gln
            20                  25                  30

<210> SEQ ID NO 16
<211> LENGTH: 31
<212> TYPE: PRT
<213> ORGANISM: Artificial Sequence
<220> FEATURE:
<223> OTHER INFORMATION: Synthetic polypeptide

<400> SEQUENCE: 16

Leu Ala Arg Leu Glu Glu Lys Leu Lys Thr Leu Lys Ala Gln Leu Ser
1               5                   10                  15

Glu Leu Ala Ser Thr Leu Asn Met Leu Arg Glu Gln Leu Ala Gln
            20                  25                  30

<210> SEQ ID NO 17
<211> LENGTH: 31
<212> TYPE: PRT
<213> ORGANISM: Artificial Sequence
<220> FEATURE:
<223> OTHER INFORMATION: Synthetic polypeptide

<400> SEQUENCE: 17

Ile Ala Arg Leu Glu Glu Lys Ile Lys Thr Leu Lys Ala Gln Ile Ser
1               5                   10                  15

Glu Leu Ala Ser Thr Ile Asn Met Leu Arg Glu Gln Ile Ala Gln
            20                  25                  30

<210> SEQ ID NO 18
<211> LENGTH: 31
<212> TYPE: PRT
<213> ORGANISM: Artificial Sequence
<220> FEATURE:
<223> OTHER INFORMATION: Synthetic polypeptide

<400> SEQUENCE: 18

Ile Ala Arg Ile Glu Glu Lys Ile Lys Thr Ile Lys Ala Gln Ile Ser
1               5                   10                  15

Glu Ile Ala Ser Thr Ile Asn Met Ile Arg Glu Gln Ile Ala Gln
            20                  25                  30

<210> SEQ ID NO 19
<211> LENGTH: 31
<212> TYPE: PRT
<213> ORGANISM: Artificial Sequence
<220> FEATURE:
<223> OTHER INFORMATION: Synthetic polypeptide

<400> SEQUENCE: 19

Val Ala Arg Leu Glu Glu Lys Val Lys Thr Leu Lys Ala Gln Val Ser
1               5                   10                  15

Glu Leu Ala Ser Thr Val Asn Met Leu Arg Glu Gln Val Ala Gln
            20                  25                  30

<210> SEQ ID NO 20
<211> LENGTH: 31
```

```
<212> TYPE: PRT
<213> ORGANISM: Artificial Sequence
<220> FEATURE:
<223> OTHER INFORMATION: Synthetic polypeptide

<400> SEQUENCE: 20

Leu Ala Arg Val Glu Glu Lys Leu Lys Thr Val Lys Ala Gln Leu Ser
1               5                   10                  15

Glu Val Ala Ser Thr Leu Asn Met Val Arg Glu Gln Leu Ala Gln
            20                  25                  30

<210> SEQ ID NO 21
<211> LENGTH: 31
<212> TYPE: PRT
<213> ORGANISM: Artificial Sequence
<220> FEATURE:
<223> OTHER INFORMATION: Synthetic polypeptide

<400> SEQUENCE: 21

Leu Ser Arg Ile Glu Glu Lys Leu Lys Thr Ile Lys Ser Gln Leu Thr
1               5                   10                  15

Glu Ile Ala Ser Thr Leu Ser Leu Ile Arg Glu Gln Leu Ala Gln
            20                  25                  30

<210> SEQ ID NO 22
<211> LENGTH: 31
<212> TYPE: PRT
<213> ORGANISM: Artificial Sequence
<220> FEATURE:
<223> OTHER INFORMATION: Synthetic polypeptide

<400> SEQUENCE: 22

Leu Ser Arg Leu Glu Glu Lys Leu Lys Thr Leu Lys Ser Gln Leu Thr
1               5                   10                  15

Glu Leu Ala Ser Thr Leu Ser Leu Leu Arg Glu Gln Leu Ala Gln
            20                  25                  30

<210> SEQ ID NO 23
<211> LENGTH: 31
<212> TYPE: PRT
<213> ORGANISM: Artificial Sequence
<220> FEATURE:
<223> OTHER INFORMATION: Synthetic polypeptide

<400> SEQUENCE: 23

Ile Ser Arg Leu Glu Glu Lys Ile Lys Thr Leu Lys Ser Gln Ile Thr
1               5                   10                  15

Glu Leu Ala Ser Thr Ile Ser Leu Leu Arg Glu Gln Ile Ala Gln
            20                  25                  30

<210> SEQ ID NO 24
<211> LENGTH: 31
<212> TYPE: PRT
<213> ORGANISM: Artificial Sequence
<220> FEATURE:
<223> OTHER INFORMATION: Synthetic polypeptide

<400> SEQUENCE: 24

Ile Ser Arg Ile Glu Glu Lys Ile Lys Thr Ile Lys Ser Gln Ile Thr
1               5                   10                  15

Glu Ile Ala Ser Thr Ile Ser Leu Ile Arg Glu Gln Ile Ala Gln
            20                  25                  30

<210> SEQ ID NO 25
<211> LENGTH: 31
```

```
<212> TYPE: PRT
<213> ORGANISM: Artificial Sequence
<220> FEATURE:
<223> OTHER INFORMATION: Synthetic polypeptide

<400> SEQUENCE: 25

Val Ser Arg Leu Glu Glu Lys Val Lys Thr Leu Lys Ser Gln Val Thr
1               5                   10                  15

Glu Leu Ala Ser Thr Val Ser Leu Leu Arg Glu Gln Val Ala Gln
            20                  25                  30

<210> SEQ ID NO 26
<211> LENGTH: 31
<212> TYPE: PRT
<213> ORGANISM: Artificial Sequence
<220> FEATURE:
<223> OTHER INFORMATION: Synthetic polypeptide

<400> SEQUENCE: 26

Leu Ser Arg Val Glu Glu Lys Leu Lys Thr Val Lys Ser Gln Leu Thr
1               5                   10                  15

Glu Val Ala Ser Thr Leu Ser Leu Val Arg Glu Gln Leu Ala Gln
            20                  25                  30

<210> SEQ ID NO 27
<211> LENGTH: 31
<212> TYPE: PRT
<213> ORGANISM: Artificial Sequence
<220> FEATURE:
<223> OTHER INFORMATION: Synthetic polypeptide

<400> SEQUENCE: 27

Leu Met Ser Ile Glu Lys Lys Leu Glu Glu Ile Thr Gln Thr Leu Met
1               5                   10                  15

Gln Ile Gln Asn Glu Leu Ser Met Ile Lys Asn Glu Leu Ala Gln
            20                  25                  30

<210> SEQ ID NO 28
<211> LENGTH: 31
<212> TYPE: PRT
<213> ORGANISM: Artificial Sequence
<220> FEATURE:
<223> OTHER INFORMATION: Synthetic polypeptide

<400> SEQUENCE: 28

Leu Met Ser Leu Glu Lys Lys Leu Glu Glu Leu Thr Gln Thr Leu Met
1               5                   10                  15

Gln Leu Gln Asn Glu Leu Ser Met Leu Lys Asn Glu Leu Ala Gln
            20                  25                  30

<210> SEQ ID NO 29
<211> LENGTH: 31
<212> TYPE: PRT
<213> ORGANISM: Artificial Sequence
<220> FEATURE:
<223> OTHER INFORMATION: Synthetic polypeptide

<400> SEQUENCE: 29

Ile Met Ser Leu Glu Lys Lys Ile Glu Glu Leu Thr Gln Thr Ile Met
1               5                   10                  15

Gln Leu Gln Asn Glu Ile Ser Met Leu Lys Asn Glu Ile Ala Gln
            20                  25                  30

<210> SEQ ID NO 30
<211> LENGTH: 31
```

```
<212> TYPE: PRT
<213> ORGANISM: Artificial Sequence
<220> FEATURE:
<223> OTHER INFORMATION: Synthetic polypeptide

<400> SEQUENCE: 30

Ile Met Ser Ile Glu Lys Lys Ile Glu Glu Ile Thr Gln Thr Ile Met
1               5                   10                  15

Gln Ile Gln Asn Glu Ile Ser Met Ile Lys Asn Glu Ile Ala Gln
            20                  25                  30

<210> SEQ ID NO 31
<211> LENGTH: 31
<212> TYPE: PRT
<213> ORGANISM: Artificial Sequence
<220> FEATURE:
<223> OTHER INFORMATION: Synthetic polypeptide

<400> SEQUENCE: 31

Val Met Ser Leu Glu Lys Lys Val Glu Glu Leu Thr Gln Thr Val Met
1               5                   10                  15

Gln Leu Gln Asn Glu Val Ser Met Leu Lys Asn Glu Val Ala Gln
            20                  25                  30

<210> SEQ ID NO 32
<211> LENGTH: 31
<212> TYPE: PRT
<213> ORGANISM: Artificial Sequence
<220> FEATURE:
<223> OTHER INFORMATION: Synthetic polypeptide

<400> SEQUENCE: 32

Leu Met Ser Val Glu Lys Lys Leu Glu Glu Val Thr Gln Thr Leu Met
1               5                   10                  15

Gln Val Gln Asn Glu Leu Ser Met Val Lys Asn Glu Leu Ala Gln
            20                  25                  30

<210> SEQ ID NO 33
<211> LENGTH: 31
<212> TYPE: PRT
<213> ORGANISM: Artificial Sequence
<220> FEATURE:
<223> OTHER INFORMATION: Synthetic polypeptide

<400> SEQUENCE: 33

Leu Gln Ser Ile Glu Lys Lys Leu Glu Asp Ile Ser Ser Leu Leu Gly
1               5                   10                  15

Gln Ile Gln Ser Glu Leu Thr Leu Ile Arg Asn Glu Leu Ala Gln
            20                  25                  30

<210> SEQ ID NO 34
<211> LENGTH: 31
<212> TYPE: PRT
<213> ORGANISM: Artificial Sequence
<220> FEATURE:
<223> OTHER INFORMATION: Synthetic polypeptide

<400> SEQUENCE: 34

Leu Gln Ser Leu Glu Lys Lys Leu Glu Asp Leu Ser Ser Leu Leu Gly
1               5                   10                  15

Gln Leu Gln Ser Glu Leu Thr Leu Leu Arg Asn Glu Leu Ala Gln
            20                  25                  30

<210> SEQ ID NO 35
<211> LENGTH: 31
```

```
<212> TYPE: PRT
<213> ORGANISM: Artificial Sequence
<220> FEATURE:
<223> OTHER INFORMATION: Synthetic polypeptide

<400> SEQUENCE: 35

Ile Gln Ser Leu Glu Lys Lys Ile Glu Asp Leu Ser Ser Leu Ile Gly
1               5                   10                  15
Gln Leu Gln Ser Glu Ile Thr Leu Leu Arg Asn Glu Ile Ala Gln
            20                  25                  30

<210> SEQ ID NO 36
<211> LENGTH: 31
<212> TYPE: PRT
<213> ORGANISM: Artificial Sequence
<220> FEATURE:
<223> OTHER INFORMATION: Synthetic polypeptide

<400> SEQUENCE: 36

Ile Gln Ser Ile Glu Lys Lys Ile Glu Asp Ile Ser Ser Leu Ile Gly
1               5                   10                  15
Gln Ile Gln Ser Glu Ile Thr Leu Ile Arg Asn Glu Ile Ala Gln
            20                  25                  30

<210> SEQ ID NO 37
<211> LENGTH: 32
<212> TYPE: PRT
<213> ORGANISM: Artificial Sequence
<220> FEATURE:
<223> OTHER INFORMATION: Synthetic polypeptide

<400> SEQUENCE: 37

Leu Ser Ser Ile Glu Lys Lys Gln Glu Glu Gln Thr Ser Gln Leu Ile
1               5                   10                  15
Gln Ile Ser Asn Glu Leu Thr Leu Ile Arg Asn Glu Leu Ala Gln Ser
            20                  25                  30

<210> SEQ ID NO 38
<211> LENGTH: 31
<212> TYPE: PRT
<213> ORGANISM: Artificial Sequence
<220> FEATURE:
<223> OTHER INFORMATION: Synthetic polypeptide

<400> SEQUENCE: 38

Val Met Ser Leu Glu Lys Lys Ala Glu Glu Leu Thr Gln Thr Asn Met
1               5                   10                  15
Gln Leu Gln Asn Glu Val Ser Met Leu Lys Asn Glu Val Ala Gln
            20                  25                  30

<210> SEQ ID NO 39
<211> LENGTH: 31
<212> TYPE: PRT
<213> ORGANISM: Artificial Sequence
<220> FEATURE:
<223> OTHER INFORMATION: Synthetic polypeptide

<400> SEQUENCE: 39

Ile Ser Arg Leu Glu Glu Lys Val Lys Thr Leu Lys Ser Gln Asn Thr
1               5                   10                  15
Glu Leu Ala Ser Thr Ala Ser Leu Leu Arg Glu Gln Val Ala Gln
            20                  25                  30

<210> SEQ ID NO 40
<211> LENGTH: 31
```

```
<212> TYPE: PRT
<213> ORGANISM: Artificial Sequence
<220> FEATURE:
<223> OTHER INFORMATION: Synthetic polypeptide

<400> SEQUENCE: 40

Ile Ala Arg Leu Glu Glu Lys Val Lys Thr Leu Lys Ala Gln Asn Ser
1               5                   10                  15
Glu Leu Ala Ser Thr Ala Asn Met Leu Arg Glu Gln Val Ala Gln
            20                  25                  30

<210> SEQ ID NO 41
<211> LENGTH: 31
<212> TYPE: PRT
<213> ORGANISM: Artificial Sequence
<220> FEATURE:
<223> OTHER INFORMATION: Synthetic polypeptide

<400> SEQUENCE: 41

Val Lys Cys Leu Glu Asn Arg Val Ala Val Leu Glu Asn Gln Asn Lys
1               5                   10                  15
Thr Leu Ile Glu Glu Leu Lys Thr Leu Lys Asp Leu Tyr Ser Asn
            20                  25                  30

<210> SEQ ID NO 42
<211> LENGTH: 31
<212> TYPE: PRT
<213> ORGANISM: Artificial Sequence
<220> FEATURE:
<223> OTHER INFORMATION: Synthetic polypeptide

<400> SEQUENCE: 42

Val Gln Ser Leu Glu Lys Lys Ala Glu Asp Leu Ser Ser Leu Asn Gly
1               5                   10                  15
Gln Leu Gln Ser Glu Val Thr Leu Leu Arg Asn Glu Val Ala Gln
            20                  25                  30

<210> SEQ ID NO 43
<211> LENGTH: 30
<212> TYPE: PRT
<213> ORGANISM: Artificial Sequence
<220> FEATURE:
<223> OTHER INFORMATION: Synthetic polypeptide

<400> SEQUENCE: 43

Lys Ala Gln Ala Ser Ser Val Pro Thr Ala Gln Pro Gln Ala Glu Gly
1               5                   10                  15
Ser Leu Ala Lys Ala Thr Thr Ala Pro Ala Thr Thr Arg Asn
            20                  25                  30

<210> SEQ ID NO 44
<211> LENGTH: 35
<212> TYPE: PRT
<213> ORGANISM: Artificial Sequence
<220> FEATURE:
<223> OTHER INFORMATION: Synthetic polypeptide

<400> SEQUENCE: 44

Lys Ala Gln Ala Ser Ser Val Pro Thr Ala Gln Pro Gln Ala Glu Gly
1               5                   10                  15
Ser Leu Ala Lys Ala Thr Thr Ala Pro Ala Thr Thr Arg Asn Thr Gly
            20                  25                  30
Arg Gly Gly
        35
```

<210> SEQ ID NO 45
<211> LENGTH: 56
<212> TYPE: PRT
<213> ORGANISM: Artificial Sequence
<220> FEATURE:
<223> OTHER INFORMATION: Synthetic polypeptide

<400> SEQUENCE: 45

Lys Ala Gln Ala Ser Ser Val Pro Thr Ala Gln Pro Gln Ala Glu Gly
1               5                   10                  15

Ser Leu Ala Lys Ala Thr Thr Ala Pro Ala Thr Thr Arg Asn Thr Gly
            20                  25                  30

Arg Gly Gly Glu Glu Lys Lys Lys Glu Lys Glu Lys Glu Glu Gln Glu
        35                  40                  45

Glu Arg Glu Thr Lys Thr Pro Glu
    50                  55

<210> SEQ ID NO 46
<211> LENGTH: 57
<212> TYPE: PRT
<213> ORGANISM: Artificial Sequence
<220> FEATURE:
<223> OTHER INFORMATION: Synthetic polypeptide

<400> SEQUENCE: 46

Lys Ala Gln Ala Ser Ser Val Pro Thr Ala Gln Pro Gln Ala Glu Gly
1               5                   10                  15

Ser Leu Ala Lys Ala Thr Thr Ala Pro Ala Thr Thr Arg Asn Thr Gly
            20                  25                  30

Arg Gly Gly Glu Glu Lys Lys Lys Glu Lys Glu Lys Glu Glu Gln Glu
        35                  40                  45

Glu Arg Glu Thr Lys Thr Pro Glu Cys
    50                  55

<210> SEQ ID NO 47
<211> LENGTH: 63
<212> TYPE: PRT
<213> ORGANISM: Artificial Sequence
<220> FEATURE:
<223> OTHER INFORMATION: Synthetic polypeptide

<400> SEQUENCE: 47

Lys Ala Gln Ala Ser Ser Val Pro Thr Ala Gln Pro Gln Ala Glu Gly
1               5                   10                  15

Ser Leu Ala Lys Ala Thr Thr Ala Pro Ala Thr Thr Arg Asn Thr Gly
            20                  25                  30

Arg Gly Gly Glu Glu Lys Lys Lys Glu Lys Glu Lys Glu Glu Gln Glu
        35                  40                  45

Glu Arg Glu Thr Lys Thr Pro Glu Cys Pro Ser His Thr Gln Pro
    50                  55                  60

<210> SEQ ID NO 48
<211> LENGTH: 96
<212> TYPE: DNA
<213> ORGANISM: Artificial Sequence
<220> FEATURE:
<223> OTHER INFORMATION: Synthetic oligonucleotide

<400> SEQUENCE: 48
cttagctcta ttgagaagaa acttgaggag attacctctc aactgattca gatcagcaat      60
gaactgaccc ttatccgcaa tgagctggcc caatga                                96

<210> SEQ ID NO 49
<211> LENGTH: 96
<212> TYPE: DNA
<213> ORGANISM: Artificial Sequence
<220> FEATURE:
<223> OTHER INFORMATION: Synthetic oligonucleotide

<400> SEQUENCE: 49
cttagctcta ttgagaagaa acttgaggag attacctctc aactgattca gatccgcaat      60
gaactgaccc ttatccgcaa tgagctggcc caatga                                96

<210> SEQ ID NO 50
<211> LENGTH: 96
<212> TYPE: DNA
<213> ORGANISM: Artificial Sequence
<220> FEATURE:
<223> OTHER INFORMATION: Synthetic oligonucleotide

<400> SEQUENCE: 50
cttagctcta ttgagaagaa acttgaggag attacctctc aactgcaaca gatccgcaat      60
gaactgaccc ttatccgcaa tgagctggcc caatga                                96

<210> SEQ ID NO 51
<211> LENGTH: 96
<212> TYPE: DNA
<213> ORGANISM: Artificial Sequence
<220> FEATURE:
<223> OTHER INFORMATION: Synthetic oligonucleotide

<400> SEQUENCE: 51
attagctctt tagagaagaa aattgaggag ctgacctctc aaatccagca gctgcgcaat      60
gaaatcaccc ttcttcgtaa tgagattgcc caatga                                96

<210> SEQ ID NO 52
<211> LENGTH: 96
<212> TYPE: DNA
<213> ORGANISM: Artificial Sequence
<220> FEATURE:
<223> OTHER INFORMATION: Synthetic oligonucleotide

<400> SEQUENCE: 52
atcagctcta ttgagaagaa aatcgaggag attacctctc aaatcattca gattcgcaat      60
gaaatcacgc ttatccgtaa tgagattgcc caatga                                96

<210> SEQ ID NO 53
<211> LENGTH: 96
<212> TYPE: DNA
<213> ORGANISM: Artificial Sequence
<220> FEATURE:
<223> OTHER INFORMATION: Synthetic oligonucleotide

<400> SEQUENCE: 53
cttagctctc ttgagaagaa acttgaggag cttacctctc aactgattca gcttcgcaat      60
gaactgaccc ttctgcgtaa tgagctggcc caatga                                96

<210> SEQ ID NO 54
<211> LENGTH: 96
<212> TYPE: DNA
<213> ORGANISM: Artificial Sequence
<220> FEATURE:
<223> OTHER INFORMATION: Synthetic oligonucleotide

<400> SEQUENCE: 54

```
gttagctctc ttgagaagaa agttgaggag cttacctctc aagtgattca gcttcgcaat    60
gaagtgaccc ttctgcgtaa tgaggttgcc caatga                              96
```

<210> SEQ ID NO 55
<211> LENGTH: 96
<212> TYPE: DNA
<213> ORGANISM: Artificial Sequence
<220> FEATURE:
<223> OTHER INFORMATION: Synthetic oligonucleotide

<400> SEQUENCE: 55

```
cttaaatcta ttgagaaccg gcttgccgtt attgagaacc aactgaaaac catcattgaa    60
gagcttaaga ccatcaaaga ccttctgtct aactga                              96
```

<210> SEQ ID NO 56
<211> LENGTH: 96
<212> TYPE: DNA
<213> ORGANISM: Artificial Sequence
<220> FEATURE:
<223> OTHER INFORMATION: Synthetic oligonucleotide

<400> SEQUENCE: 56

```
cttaaatctc ttgagaaccg gcttgccgtt cttgagaacc aactgaaaac cctgattgaa    60
gagcttaaga ccctgaaaga ccttctgtct aactga                              96
```

<210> SEQ ID NO 57
<211> LENGTH: 96
<212> TYPE: DNA
<213> ORGANISM: Artificial Sequence
<220> FEATURE:
<223> OTHER INFORMATION: Synthetic oligonucleotide

<400> SEQUENCE: 57

```
attaaatctc ttgagaaccg gatcgccgtt cttgagaacc aaatcaaaac ccttattgaa    60
gagattaaga ccctgaaaga ccttatctct aactga                              96
```

<210> SEQ ID NO 58
<211> LENGTH: 96
<212> TYPE: DNA
<213> ORGANISM: Artificial Sequence
<220> FEATURE:
<223> OTHER INFORMATION: Synthetic oligonucleotide

<400> SEQUENCE: 58

```
attaaatcta ttgagaaccg gattgccgtt attgagaacc aaatcaaaac catcattgaa    60
gagattaaga ccatcaaaga ccttatctct aactga                              96
```

<210> SEQ ID NO 59
<211> LENGTH: 96
<212> TYPE: DNA
<213> ORGANISM: Artificial Sequence
<220> FEATURE:
<223> OTHER INFORMATION: Synthetic oligonucleotide

<400> SEQUENCE: 59

```
gttaaatctc ttgagaaccg ggttgccgtt cttgagaacc aagttaaaac cctgattgaa    60
gaggttaaga cccttaaaga ccttgtttct aactga                              96
```

<210> SEQ ID NO 60
<211> LENGTH: 96
<212> TYPE: DNA
<213> ORGANISM: Artificial Sequence
<220> FEATURE:

<223> OTHER INFORMATION: Synthetic oligonucleotide

<400> SEQUENCE: 60

```
cttaaatctg ttgagaaccg gcttgccgtt gttgagaacc aactgaaaac cgttattgaa    60
gagcttaaga ccgttaaaga ccttctgtct aactga                              96
```

<210> SEQ ID NO 61
<211> LENGTH: 96
<212> TYPE: DNA
<213> ORGANISM: Artificial Sequence
<220> FEATURE:
<223> OTHER INFORMATION: Synthetic oligonucleotide

<400> SEQUENCE: 61

```
cttgctcgga ttgaagagaa acttaaaacc attaaagcgc aactgtctga gatcgcgtct    60
accctgaaca tgatccgtga acaactggcc caatga                              96
```

<210> SEQ ID NO 62
<211> LENGTH: 96
<212> TYPE: DNA
<213> ORGANISM: Artificial Sequence
<220> FEATURE:
<223> OTHER INFORMATION: Synthetic oligonucleotide

<400> SEQUENCE: 62

```
cttgctcggc ttgaagagaa acttaaaacc cttaaagcgc aactgtctga gctggcgtct    60
accctgaaca tgctccgtga acaactggcc caatga                              96
```

<210> SEQ ID NO 63
<211> LENGTH: 96
<212> TYPE: DNA
<213> ORGANISM: Artificial Sequence
<220> FEATURE:
<223> OTHER INFORMATION: Synthetic oligonucleotide

<400> SEQUENCE: 63

```
attgctcggc ttgaagagaa aattaaaacc ctgaaagcgc aaatttctga gcttgcgtct    60
accattaaca tgcttcgtga acaaatcgcc caatga                              96
```

<210> SEQ ID NO 64
<211> LENGTH: 93
<212> TYPE: DNA
<213> ORGANISM: Artificial Sequence
<220> FEATURE:
<223> OTHER INFORMATION: Synthetic oligonucleotide

<400> SEQUENCE: 64

```
attgctcgga ttgaagagaa aatcaaaacc attaaagcgc aaatctctga gatcgcgtct    60
accatcaaca tgatccgtga acaagcccaa tga                                 93
```

<210> SEQ ID NO 65
<211> LENGTH: 96
<212> TYPE: DNA
<213> ORGANISM: Artificial Sequence
<220> FEATURE:
<223> OTHER INFORMATION: Synthetic oligonucleotide

<400> SEQUENCE: 65

```
gttgctcggc ttgaagagaa agttaaaacc cttaaagcgc aagtttctga gcttgcgtct    60
accgttaaca tgcttcgtga acaagtcgcc caatga                              96
```

<210> SEQ ID NO 66

```
<211> LENGTH: 96
<212> TYPE: DNA
<213> ORGANISM: Artificial Sequence
<220> FEATURE:
<223> OTHER INFORMATION: Synthetic oligonucleotide

<400> SEQUENCE: 66
cttgctcggg tcgaagagaa acttaaaacc gttaaagcgc aactgtctga ggtcgcgtct    60
accctgaaca tggttcgtga acaactggcc caatga                             96

<210> SEQ ID NO 67
<211> LENGTH: 96
<212> TYPE: PRT
<213> ORGANISM: Artificial Sequence
<220> FEATURE:
<223> OTHER INFORMATION: Synthetic polypeptide

<400> SEQUENCE: 67

Cys Thr Thr Ala Gly Cys Cys Gly Gly Ala Thr Thr Gly Ala Ala Gly
1               5                   10                  15

Ala Gly Ala Ala Ala Cys Thr Thr Ala Ala Ala Cys Cys Ala Thr
            20                  25                  30

Thr Ala Ala Ala Thr Cys Thr Cys Ala Ala Cys Thr Gly Ala Cys Thr
        35                  40                  45

Gly Ala Gly Ala Thr Cys Gly Cys Gly Thr Cys Thr Ala Cys Cys Cys
    50                  55                  60

Thr Gly Thr Cys Thr Cys Thr Thr Ala Thr Cys Cys Gly Thr Gly Ala
65                  70                  75                  80

Ala Cys Ala Ala Cys Thr Gly Gly Cys Cys Cys Ala Ala Thr Gly Ala
                85                  90                  95

<210> SEQ ID NO 68
<211> LENGTH: 96
<212> TYPE: DNA
<213> ORGANISM: Artificial Sequence
<220> FEATURE:
<223> OTHER INFORMATION: Synthetic oligonucleotide

<400> SEQUENCE: 68
cttagccggc ttgaagagaa acttaagacc ctgaaatctc aactgactga gcttgcgtct    60
acccttcttt gctgcgtga acaacttgcc caatga                              96

<210> SEQ ID NO 69
<211> LENGTH: 96
<212> TYPE: DNA
<213> ORGANISM: Artificial Sequence
<220> FEATURE:
<223> OTHER INFORMATION: Synthetic oligonucleotide

<400> SEQUENCE: 69
atcagccggc ttgaagagaa gattaagacc ctgaaatctc aaatcactga gcttgcgtct    60
accatttctc ttctgcgtga acaaattgcc caatga                             96

<210> SEQ ID NO 70
<211> LENGTH: 96
<212> TYPE: DNA
<213> ORGANISM: Artificial Sequence
<220> FEATURE:
<223> OTHER INFORMATION: Synthetic oligonucleotide

<400> SEQUENCE: 70
atcagccgga ttgaagagaa gattaagacc atcaaatctc aaatcactga gattgcgtct    60
```

```
accatttctc ttattcgtga acaaattgcc caatga                                    96
```

<210> SEQ ID NO 71
<211> LENGTH: 96
<212> TYPE: DNA
<213> ORGANISM: Artificial Sequence
<220> FEATURE:
<223> OTHER INFORMATION: Synthetic oligonucleotide

<400> SEQUENCE: 71

```
gttagccggc ttgaagagaa ggttaagacc ctgaaatctc aagttactga gcttgcgtct         60
accgtctctc ttctgcgtga acaagttgcc caatga                                    96
```

<210> SEQ ID NO 72
<211> LENGTH: 96
<212> TYPE: DNA
<213> ORGANISM: Artificial Sequence
<220> FEATURE:
<223> OTHER INFORMATION: Synthetic oligonucleotide

<400> SEQUENCE: 72

```
cttagccggg ttgaagagaa gctgaagacc gtcaaatctc aacttactga ggttgcgtct         60 acccttt ctc ttgtccgtga acaacttgcc caatga                                   96
```

<210> SEQ ID NO 73
<211> LENGTH: 96
<212> TYPE: DNA
<213> ORGANISM: Artificial Sequence
<220> FEATURE:
<223> OTHER INFORMATION: Synthetic oligonucleotide

<400> SEQUENCE: 73

```
cttatgtcta ttgagaagaa acttgaggag attacccaga ctctgatgca gatccagaat         60
gaactgtcta tgatcaagaa tgagctggcc caatga                                    96
```

<210> SEQ ID NO 74
<211> LENGTH: 96
<212> TYPE: DNA
<213> ORGANISM: Artificial Sequence
<220> FEATURE:
<223> OTHER INFORMATION: Synthetic oligonucleotide

<400> SEQUENCE: 74

```
cttatgtctc tggagaagaa acttgaggag cttacccaga ctctgatgca gcttcagaat         60
gaactgtcta tgctgaagaa tgagctggcc caatga                                    96
```

<210> SEQ ID NO 75
<211> LENGTH: 96
<212> TYPE: DNA
<213> ORGANISM: Artificial Sequence
<220> FEATURE:
<223> OTHER INFORMATION: Synthetic oligonucleotide

<400> SEQUENCE: 75

```
atcatgtctc tggagaagaa gatcgaggag cttacccaga ctatcatgca gcttcagaat         60
gaaatttcta tgctgaagaa tgagattgcc caatga                                    96
```

<210> SEQ ID NO 76
<211> LENGTH: 96
<212> TYPE: DNA
<213> ORGANISM: Artificial Sequence
<220> FEATURE:
<223> OTHER INFORMATION: Synthetic oligonucleotide -continued

<400> SEQUENCE: 76
atcatgtcta ttgagaagaa gatcgaggag atcacccaga ctatcatgca gattcagaat    60
gaaatttcta tgatcaagaa tgagattgcc caatga    96

<210> SEQ ID NO 77
<211> LENGTH: 96
<212> TYPE: DNA
<213> ORGANISM: Artificial Sequence
<220> FEATURE:
<223> OTHER INFORMATION: Synthetic oligonucleotide

<400> SEQUENCE: 77
gttatgtctc ttgagaagaa ggttgaggag cttacccaga ctgtcatgca gcttcagaat    60
gaagtttcta tgcttaagaa tgaggttgcc caatga    96

<210> SEQ ID NO 78
<211> LENGTH: 96
<212> TYPE: DNA
<213> ORGANISM: Artificial Sequence
<220> FEATURE:
<223> OTHER INFORMATION: Synthetic oligonucleotide

<400> SEQUENCE: 78
ctgatgtctg tcgagaagaa gcttgaggag gttacccaga ctctcatgca ggttcagaat    60
gaactttcta tggttaagaa tgagcttgcc caatga    96

<210> SEQ ID NO 79
<211> LENGTH: 96
<212> TYPE: DNA
<213> ORGANISM: Artificial Sequence
<220> FEATURE:
<223> OTHER INFORMATION: Synthetic oligonucleotide

<400> SEQUENCE: 79
cttcagtcta ttgagaagaa acttgaggac attagctctc ttctgggtca gatccaatct    60
gaactgaccc ttatccgcaa tgagctggcc caatga    96

<210> SEQ ID NO 80
<211> LENGTH: 96
<212> TYPE: DNA
<213> ORGANISM: Artificial Sequence
<220> FEATURE:
<223> OTHER INFORMATION: Synthetic oligonucleotide

<400> SEQUENCE: 80
cttcagtctc ttgagaagaa acttgaggac cttagctctc ttctgggtca gctgcaatct    60
gagctgaccc ttctgcgcaa tgagctggca caatga    96

<210> SEQ ID NO 81
<211> LENGTH: 96
<212> TYPE: DNA
<213> ORGANISM: Artificial Sequence
<220> FEATURE:
<223> OTHER INFORMATION: Synthetic oligonucleotide

<400> SEQUENCE: 81
attcagtctc tggagaagaa aatcgaggac cttagctctc ttattggtca gcttcaatct    60
gaaatcaccc ttcttcgcaa tgagattgcc caatga    96

<210> SEQ ID NO 82
<211> LENGTH: 96
<212> TYPE: DNA

<213> ORGANISM: Artificial Sequence
<220> FEATURE:
<223> OTHER INFORMATION: Synthetic oligonucleotide

<400> SEQUENCE: 82

```
attcagtcta ttgagaagaa aatcgaggac attagctctc ttattggtca gattcaatct    60
gaaatcaccc ttatccgcaa tgagattgcc caatga                              96
```

<210> SEQ ID NO 83
<211> LENGTH: 80
<212> TYPE: DNA
<213> ORGANISM: Artificial Sequence
<220> FEATURE:
<223> OTHER INFORMATION: Synthetic oligonucleotide

<400> SEQUENCE: 83

```
acaaacgcgt acgctgatat ccagatgacc caatctccgt cagcctgagc gccagtgttg    60
gtgatcgagt taccattact                                                80
```

<210> SEQ ID NO 84
<211> LENGTH: 85
<212> TYPE: DNA
<213> ORGANISM: Artificial Sequence
<220> FEATURE:
<223> OTHER INFORMATION: Synthetic oligonucleotide

<400> SEQUENCE: 84

```
ggttttgtt gataccagtg aagattatta ctgatagatt ggctggcgcg gcaagtaatg     60
gtaactcgat caccaacact ggcgc                                          85
```

<210> SEQ ID NO 85
<211> LENGTH: 81
<212> TYPE: DNA
<213> ORGANISM: Artificial Sequence
<220> FEATURE:
<223> OTHER INFORMATION: Synthetic oligonucleotide

<400> SEQUENCE: 85

```
cttcactggt atcaacaaaa accgggtaaa gctccgaaac ttcttatcta tcacgcctct    60
cagagcatta gcggcgttcc g                                              81
```

<210> SEQ ID NO 86
<211> LENGTH: 80
<212> TYPE: DNA
<213> ORGANISM: Artificial Sequence
<220> FEATURE:
<223> OTHER INFORMATION: Synthetic oligonucleotide

<400> SEQUENCE: 86

```
gagagctgat ggtaagggta aagtccgtgc ccgagccaga gccagagaag cggctcggaa    60
cgccgctaat gctctgagag                                                80
```

<210> SEQ ID NO 87
<211> LENGTH: 65
<212> TYPE: DNA
<213> ORGANISM: Artificial Sequence
<220> FEATURE:
<223> OTHER INFORMATION: Synthetic oligonucleotide

<400> SEQUENCE: 87

```
ctttaccctt accatcagct ctcttcagcc ggaagacttt gccacctatt attgtcagca    60
gtcta                                                                65
```

<210> SEQ ID NO 88
<211> LENGTH: 85
<212> TYPE: DNA
<213> ORGANISM: Artificial Sequence
<220> FEATURE:
<223> OTHER INFORMATION: Synthetic oligonucleotide

<400> SEQUENCE: 88
ggtgcagcca cagtgcgctt aatctcgacc ttggtacctt gaccgaaggt atacggccag    60
ctattagact gctgacaata atagg                                         85

<210> SEQ ID NO 89
<211> LENGTH: 89
<212> TYPE: DNA
<213> ORGANISM: Artificial Sequence
<220> FEATURE:
<223> OTHER INFORMATION: Synthetic oligonucleotide

<400> SEQUENCE: 89
acaaacgcgt acgctgaagt tcaacttgtt gagtctggtg gcggtctggt tcagcccggg    60
ggctctctgc gcctgtcttg cgcagcaag                                     89

<210> SEQ ID NO 90
<211> LENGTH: 75
<212> TYPE: DNA
<213> ORGANISM: Artificial Sequence
<220> FEATURE:
<223> OTHER INFORMATION: Synthetic oligonucleotide

<400> SEQUENCE: 90
cttacccgga gcttgcctca cccaatggat gtaggtgtcc ttaatgttga aaccgcttgc    60
tgcgcaagac aggcg                                                    75

<210> SEQ ID NO 91
<211> LENGTH: 88
<212> TYPE: DNA
<213> ORGANISM: Artificial Sequence
<220> FEATURE:
<223> OTHER INFORMATION: Synthetic oligonucleotide

<400> SEQUENCE: 91
ggcaagctcc gggtaagggt ctggagtggg tggcacgtat cgacccggca aacgacaaca    60
ccatttacgc tgacagcgtg aagggccg                                      88

<210> SEQ ID NO 92
<211> LENGTH: 87
<212> TYPE: DNA
<213> ORGANISM: Artificial Sequence
<220> FEATURE:
<223> OTHER INFORMATION: Synthetic oligonucleotide

<400> SEQUENCE: 92
ggtacgcggt gttcttagag tcgtcgctag aaatagtaaa acggcccttc acgctgtcag    60
cgtaaatggt gttgtcgttt gccgggt                                       87

<210> SEQ ID NO 93
<211> LENGTH: 102
<212> TYPE: DNA
<213> ORGANISM: Artificial Sequence
<220> FEATURE:
<223> OTHER INFORMATION: Synthetic oligonucleotide

<400> SEQUENCE: 93

```
gactctaaga acaccgcgta ccttcagatg aactctctgc gtgccgagga caccgccgtc    60
tactactgca cggcctctgg ctactggttt gcctactggg gc                      102
```

<210> SEQ ID NO 94
<211> LENGTH: 65
<212> TYPE: DNA
<213> ORGANISM: Artificial Sequence
<220> FEATURE:
<223> OTHER INFORMATION: Synthetic oligonucleotide

<400> SEQUENCE: 94

```
ggtggaggcg ctcgagacgg tgacaagcgt gccctggccc cagtaggcaa accagtagcc    60
agagg                                                                65
```

<210> SEQ ID NO 95
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 95

```
cccggcaaac gacaacacca tttacgctg                                       29
```

<210> SEQ ID NO 96
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 96

```
acaaacgcgt acgctgatat cc                                              22
```

<210> SEQ ID NO 97
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 97

```
gatggtgcag ccacagtgcg c                                               21
```

<210> SEQ ID NO 98
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 98

```
gcgatattct ttttcatata ctgtttcctg                                      30
```

<210> SEQ ID NO 99
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 99

```
ggtggaggcg ctcgagacgg                                                 20
```

<210> SEQ ID NO 100

```
<211> LENGTH: 69
<212> TYPE: DNA
<213> ORGANISM: Artificial Sequence
<220> FEATURE:
<223> OTHER INFORMATION: Synthetic oligonucleotide

<400> SEQUENCE: 100
atgaaaaaga atatcgcatt tcttcttgca tctatgttcg tttttttctat tgctacaaac      60 gcgtacgct                                                               69

<210> SEQ ID NO 101
<211> LENGTH: 66
<212> TYPE: DNA
<213> ORGANISM: Artificial Sequence
<220> FEATURE:
<223> OTHER INFORMATION: Synthetic oligonucleotide

<400> SEQUENCE: 101
actgtggctg caccatctgt cttcatcttc ccgccatctg atgagcagtt gaaatctgga      60
actgcc                                                                  66

<210> SEQ ID NO 102
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 102
ggcctctctg ggatagaagt tattcagcag gcacacaaca gaggcagttc cagatttcaa      60

<210> SEQ ID NO 103
<211> LENGTH: 57
<212> TYPE: DNA
<213> ORGANISM: Artificial Sequence
<220> FEATURE:
<223> OTHER INFORMATION: Synthetic oligonucleotide

<400> SEQUENCE: 103
cttctatccc agagaggcca aagtacagtg gaaggtggat aacgccctcc aatcggg        57

<210> SEQ ID NO 104
<211> LENGTH: 68
<212> TYPE: DNA
<213> ORGANISM: Artificial Sequence
<220> FEATURE:
<223> OTHER INFORMATION: Synthetic oligonucleotide

<400> SEQUENCE: 104
ggctgtaggt gctgtccttg ctgtcctgct ctgtgacact ctcctgagag ttacccgatt      60
ggagggcg                                                                68

<210> SEQ ID NO 105
<211> LENGTH: 84
<212> TYPE: DNA
<213> ORGANISM: Artificial Sequence
<220> FEATURE:
<223> OTHER INFORMATION: Synthetic oligonucleotide

<400> SEQUENCE: 105
gcaaggacag cacctacagc ctcagcagca ccctgacgct gacgctgagc aaggcagact      60
acgagaaaca caaagtctac gcct                                              84

<210> SEQ ID NO 106
```

```
<211> LENGTH: 66
<212> TYPE: DNA
<213> ORGANISM: Artificial Sequence
<220> FEATURE:
<223> OTHER INFORMATION: Synthetic oligonucleotide

<400> SEQUENCE: 106
aagctctttg tgacggggct cgacaggccc tgatgggtga cttcgcaggc gtagactttg    60
tgtttc                                                              66

<210> SEQ ID NO 107
<211> LENGTH: 66
<212> TYPE: DNA
<213> ORGANISM: Artificial Sequence
<220> FEATURE:
<223> OTHER INFORMATION: Synthetic oligonucleotide

<400> SEQUENCE: 107
agccccgtca caaagagctt caacagggga gagtgttaag ctgatcctct acgccggacg    60
catcgt                                                              66

<210> SEQ ID NO 108
<211> LENGTH: 61
<212> TYPE: DNA
<213> ORGANISM: Artificial Sequence
<220> FEATURE:
<223> OTHER INFORMATION: Synthetic oligonucleotide

<400> SEQUENCE: 108
ctctagatac ccttttacg tgaacttgcg tactagggcc acgatgcgtc cggcgtagag    60
g                                                                   61

<210> SEQ ID NO 109
<211> LENGTH: 48
<212> TYPE: DNA
<213> ORGANISM: Artificial Sequence
<220> FEATURE:
<223> OTHER INFORMATION: Synthetic oligonucleotide

<400> SEQUENCE: 109
gaaatgcgat attcttttc ataaaatcac ctcaacctct agataccc                 48

<210> SEQ ID NO 110
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 110
aaaaagggta tctagaggtt gagg                                          24

<210> SEQ ID NO 111
<211> LENGTH: 40
<212> TYPE: DNA
<213> ORGANISM: Artificial Sequence
<220> FEATURE:
<223> OTHER INFORMATION: Synthetic oligonucleotide

<400> SEQUENCE: 111
gactcaacaa gttgaacttc agcgtacgcg tttgtagcaa                         40

<210> SEQ ID NO 112
<211> LENGTH: 21
<212> TYPE: DNA
```

```
<213> ORGANISM: Artificial Sequence
<220> FEATURE:
<223> OTHER INFORMATION: Synthetic oligonucleotide

<400> SEQUENCE: 112
gaagttcaac ttgttgagtc t                                              21

<210> SEQ ID NO 113
<211> LENGTH: 41
<212> TYPE: DNA
<213> ORGANISM: Artificial Sequence
<220> FEATURE:
<223> OTHER INFORMATION: Synthetic oligonucleotide

<400> SEQUENCE: 113
cacgcttgtc accgtctcga gcgcctccac caagggccca t                        41

<210> SEQ ID NO 114
<211> LENGTH: 65
<212> TYPE: DNA
<213> ORGANISM: Artificial Sequence
<220> FEATURE:
<223> OTHER INFORMATION: Synthetic oligonucleotide

<400> SEQUENCE: 114
gtgcccccag aggtgctctt ggatgagggt gccaggggga agaccgatgg gcccttggtg    60
gagcg                                                                65

<210> SEQ ID NO 115
<211> LENGTH: 64
<212> TYPE: DNA
<213> ORGANISM: Artificial Sequence
<220> FEATURE:
<223> OTHER INFORMATION: Synthetic oligonucleotide

<400> SEQUENCE: 115
cacctctggg ggcacagcgg ccctgggctg cctggtcaag gactacttcc ccgaaccggt    60
gacg                                                                 64

<210> SEQ ID NO 116
<211> LENGTH: 71
<212> TYPE: DNA
<213> ORGANISM: Artificial Sequence
<220> FEATURE:
<223> OTHER INFORMATION: Synthetic oligonucleotide

<400> SEQUENCE: 116
ggacagccgg gaaggtgtgc acgccgctgg tcagggcgcc tgagttccac gacaccgtca    60
ccggttcggg g                                                         71

<210> SEQ ID NO 117
<211> LENGTH: 114
<212> TYPE: DNA
<213> ORGANISM: Artificial Sequence
<220> FEATURE:
<223> OTHER INFORMATION: Synthetic polynucleotide

<400> SEQUENCE: 117
gacctacatc tgcaacgtga atcacaagcc cagcaacacc aaggtggaca agaaagttga    60
gcccaaatct tgtgacaaaa ctcacacaga gctctgagaa ttccgcggca tcgc         114

<210> SEQ ID NO 118
<211> LENGTH: 63
<212> TYPE: DNA
```

<213> ORGANISM: Artificial Sequence
<220> FEATURE:
<223> OTHER INFORMATION: Synthetic oligonucleotide

<400> SEQUENCE: 118
gattcacgtt gcagatgtag gtctgggtgc ccaagctgct ggagggcacg gtcaccacgc    60
tgc    63

<210> SEQ ID NO 119
<211> LENGTH: 83
<212> TYPE: DNA
<213> ORGANISM: Artificial Sequence
<220> FEATURE:
<223> OTHER INFORMATION: Synthetic oligonucleotide

<400> SEQUENCE: 119
ggccctagag tccctaacgc tcggttgccg ccgggcgttt tttattgtta actcatgttt    60
gacagcttat catcgataag ctt    83

<210> SEQ ID NO 120
<211> LENGTH: 92
<212> TYPE: DNA
<213> ORGANISM: Artificial Sequence
<220> FEATURE:
<223> OTHER INFORMATION: Synthetic oligonucleotide

<400> SEQUENCE: 120
gcgttaggga ctctagggcc gtcgcatgcc gcggaattct cagagctctg tgtgagtttt    60
gtcacaagat ttgggctcaa ctttcttgtc ac    92

<210> SEQ ID NO 121
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 121
aagcttatcg atgataagc    19

<210> SEQ ID NO 122
<211> LENGTH: 71
<212> TYPE: DNA
<213> ORGANISM: Artificial Sequence
<220> FEATURE:
<223> OTHER INFORMATION: Synthetic oligonucleotide

<400> SEQUENCE: 122
gcggcgtgca caccttcccg gctgtcctac agtcctcagg actctactcc ctcagcagcg    60
tggtgaccgt g    71

<210> SEQ ID NO 123
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 123
aacaatacta gtcaggaaac agtata    26

<210> SEQ ID NO 124
<211> LENGTH: 20
<212> TYPE: DNA

```
<213> ORGANISM: Artificial Sequence
<220> FEATURE:
<223> OTHER INFORMATION: Synthetic oligonucleotide

<400> SEQUENCE: 124
actagtattg ttatccgctc                                                    20

<210> SEQ ID NO 125
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 125
catagatgca agaagaaatg c                                                  21

<210> SEQ ID NO 126
<211> LENGTH: 54
<212> TYPE: DNA
<213> ORGANISM: Artificial Sequence
<220> FEATURE:
<223> OTHER INFORMATION: Synthetic oligonucleotide

<400> SEQUENCE: 126
cttagctcta ttgagaagaa acttgaggag attacctctc aactgattca gatc              54

<210> SEQ ID NO 127
<211> LENGTH: 56
<212> TYPE: DNA
<213> ORGANISM: Artificial Sequence
<220> FEATURE:
<223> OTHER INFORMATION: Synthetic oligonucleotide

<400> SEQUENCE: 127
ttgggccagc tcattgcgga taagggtcag ttcattgctg atctgaatca gttgag            56

<210> SEQ ID NO 128
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 128
cttagctcta ttgagaag                                                      18

<210> SEQ ID NO 129
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 129
cgaattcatt gggccagctc attgc                                              25

<210> SEQ ID NO 130
<211> LENGTH: 54
<212> TYPE: DNA
<213> ORGANISM: Artificial Sequence
<220> FEATURE:
<223> OTHER INFORMATION: Synthetic oligonucleotide

<400> SEQUENCE: 130
cttagctcta ttgagaagaa acttgaggag attacctctc aactgattca gatc              54
```

<210> SEQ ID NO 131
<211> LENGTH: 56
<212> TYPE: DNA
<213> ORGANISM: Artificial Sequence
<220> FEATURE:
<223> OTHER INFORMATION: Synthetic oligonucleotide

<400> SEQUENCE: 131
ttgggccagc tcattgcgga taagggtcag ttcattgcgg atctgaatca gttgag    56

<210> SEQ ID NO 132
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 132
cttagctcta ttgagaag    18

<210> SEQ ID NO 133
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 133
cgaattcatt gggccagctc attgc    25

<210> SEQ ID NO 134
<211> LENGTH: 54
<212> TYPE: DNA
<213> ORGANISM: Artificial Sequence
<220> FEATURE:
<223> OTHER INFORMATION: Synthetic oligonucleotide

<400> SEQUENCE: 134
cttagctcta ttgagaagaa acttgaggag attacctctc aactgcaaca gatc    54

<210> SEQ ID NO 135
<211> LENGTH: 56
<212> TYPE: DNA
<213> ORGANISM: Artificial Sequence
<220> FEATURE:
<223> OTHER INFORMATION: Synthetic oligonucleotide

<400> SEQUENCE: 135
ttgggccagc tcattgcgga taagggtcag ttcattgctg atctgttgca gttgag    56

<210> SEQ ID NO 136
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 136
cttagctcta ttgagaag    18

<210> SEQ ID NO 137
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 137
cgaattcatt gggccagctc attgc    25

<210> SEQ ID NO 138
<211> LENGTH: 57
<212> TYPE: DNA
<213> ORGANISM: Artificial Sequence
<220> FEATURE:
<223> OTHER INFORMATION: Synthetic oligonucleotide

<400> SEQUENCE: 138
cttagctctc ttgagaagaa acttgaggag cttacctctc aactgattca gcttcgg    57

<210> SEQ ID NO 139
<211> LENGTH: 55
<212> TYPE: DNA
<213> ORGANISM: Artificial Sequence
<220> FEATURE:
<223> OTHER INFORMATION: Synthetic oligonucleotide

<400> SEQUENCE: 139
attgggccag ctcattacgc agaagggtca gttcattccg aagctgaatc agttg    55

<210> SEQ ID NO 140
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 140
cttagctctc ttgagaagaa ac    22

<210> SEQ ID NO 141
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 141
cgaattcatt gggccagctc atta    24

<210> SEQ ID NO 142
<211> LENGTH: 57
<212> TYPE: DNA
<213> ORGANISM: Artificial Sequence
<220> FEATURE:
<223> OTHER INFORMATION: Synthetic oligonucleotide

<400> SEQUENCE: 142
attagctctt tagagaagaa aattgaggag ctgacctctc aaatccagca gctgcgt    57

<210> SEQ ID NO 143
<211> LENGTH: 57
<212> TYPE: DNA
<213> ORGANISM: Artificial Sequence
<220> FEATURE:
<223> OTHER INFORMATION: Synthetic oligonucleotide

<400> SEQUENCE: 143
ttgggcaatc tcattacgaa gaagggtgat tcattacgc agctgctgga tttgaga    57

<210> SEQ ID NO 144
<211> LENGTH: 22
<212> TYPE: DNA

<213> ORGANISM: Artificial Sequence
<220> FEATURE:
<223> OTHER INFORMATION: Synthetic oligonucleotide

<400> SEQUENCE: 144
attagctctt tagagaagaa aa        22

<210> SEQ ID NO 145
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 145
cgaattcatt gggcaatctc attacg        26

<210> SEQ ID NO 146
<211> LENGTH: 49
<212> TYPE: DNA
<213> ORGANISM: Artificial Sequence
<220> FEATURE:
<223> OTHER INFORMATION: Synthetic oligonucleotide

<400> SEQUENCE: 146
atcagctcta ttgagaagaa aatcgaggag attacctctc aaatcattc        49

<210> SEQ ID NO 147
<211> LENGTH: 66
<212> TYPE: DNA
<213> ORGANISM: Artificial Sequence
<220> FEATURE:
<223> OTHER INFORMATION: Synthetic oligonucleotide

<400> SEQUENCE: 147
cattgggcaa tctcattacg gataagcgtg atttcattcc gaatctgaat gatttgagag        60
gtaatc        66

<210> SEQ ID NO 148
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 148
atcagctcta ttgagaag        18

<210> SEQ ID NO 149
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 149
cgaattcatt gggcaatctc attacg        26

<210> SEQ ID NO 150
<211> LENGTH: 57
<212> TYPE: DNA
<213> ORGANISM: Artificial Sequence
<220> FEATURE:
<223> OTHER INFORMATION: Synthetic oligonucleotide

<400> SEQUENCE: 150

-continued gttagctctc ttgagaagaa agttgaggag cttacctctc aagtgattca gcttcgg    57

<210> SEQ ID NO 151
<211> LENGTH: 58
<212> TYPE: DNA
<213> ORGANISM: Artificial Sequence
<220> FEATURE:
<223> OTHER INFORMATION: Synthetic oligonucleotide

<400> SEQUENCE: 151
ttgggcaacc tcattacgca agggtcac ttcattccga agctgaatca cttgagag    58

<210> SEQ ID NO 152
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 152
gttagctctc ttgagaagaa ag    22

<210> SEQ ID NO 153
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 153
cgaattcatt gggcaacctc attacg    26

<210> SEQ ID NO 154
<211> LENGTH: 32
<212> TYPE: PRT
<213> ORGANISM: Artificial Sequence
<220> FEATURE:
<223> OTHER INFORMATION: Synthetic polypeptide

<400> SEQUENCE: 154

Leu Ser Ser Ile Glu Lys Lys Leu Glu Glu Ile Thr Ser Gln Leu Ile
1               5                   10                  15

Gln Ile Ser Asn Glu Leu Thr Leu Ile Arg Asn Glu Leu Ala Gln Ser
            20                  25                  30

<210> SEQ ID NO 155
<211> LENGTH: 31
<212> TYPE: PRT
<213> ORGANISM: Artificial Sequence
<220> FEATURE:
<223> OTHER INFORMATION: Synthetic polypeptide

<400> SEQUENCE: 155

Ile Ser Ser Ile Glu Lys Leu Ile Glu Glu Ile Leu Ser Gln Ile Ile
1               5                   10                  15

Gln Ile Arg Asn Leu Ile Thr Leu Ile Leu Asn Glu Ile Ala Gln
            20                  25                  30

<210> SEQ ID NO 156
<211> LENGTH: 31
<212> TYPE: PRT
<213> ORGANISM: Artificial Sequence
<220> FEATURE:
<223> OTHER INFORMATION: Synthetic polypeptide

<400> SEQUENCE: 156

Ile Ser Ser Ile Glu Lys Lys Ile Glu Ile Leu Ser Gln Ile Gln
1               5                   10                  15

Gln Ile Arg Asn Leu Ile Thr Ser Ile Leu Asn Glu Ile Ala Gln
                20                  25                  30

<210> SEQ ID NO 157
<211> LENGTH: 31
<212> TYPE: PRT
<213> ORGANISM: Artificial Sequence
<220> FEATURE:
<223> OTHER INFORMATION: Synthetic polypeptide

<400> SEQUENCE: 157

Ile Ser Ser Ile Glu Lys Leu Ile Glu Glu Ile Leu Ser Gln Ile Gln
1               5                   10                  15

Gln Ile Arg Asn Leu Ile Thr Leu Ile Arg Asn Glu Ile Ala Gln
                20                  25                  30

<210> SEQ ID NO 158
<211> LENGTH: 31
<212> TYPE: PRT
<213> ORGANISM: Artificial Sequence
<220> FEATURE:
<223> OTHER INFORMATION: Synthetic polypeptide

<400> SEQUENCE: 158

Ile Ser Ser Ile Glu Lys Leu Ile Glu Glu Ile Leu Ser Gln Ile Gln
1               5                   10                  15

Gln Ile Arg Asn Leu Ile Thr Ser Ile Arg Asn Glu Ile Ala Gln
                20                  25                  30

<210> SEQ ID NO 159
<211> LENGTH: 31
<212> TYPE: PRT
<213> ORGANISM: Artificial Sequence
<220> FEATURE:
<223> OTHER INFORMATION: Synthetic polypeptide

<400> SEQUENCE: 159

Ile Ser Ser Ile Glu Lys Leu Ile Glu Glu Ile Leu Ser Gln Ile Gln
1               5                   10                  15

Gln Ile Arg Asn Leu Ile Thr Ser Ile Leu Asn Glu Ile Ala Gln
                20                  25                  30

<210> SEQ ID NO 160
<211> LENGTH: 31
<212> TYPE: PRT
<213> ORGANISM: Artificial Sequence
<220> FEATURE:
<223> OTHER INFORMATION: Synthetic polypeptide

<400> SEQUENCE: 160

Ile Lys Ser Ile Glu Asn Leu Ile Ala Gln Ile Leu Asn Gln Ile Lys
1               5                   10                  15

Thr Ile Ile Glu Leu Ile Lys Thr Ile Leu Asp Leu Ile Ser Asn
                20                  25                  30

<210> SEQ ID NO 161
<211> LENGTH: 34
<212> TYPE: PRT
<213> ORGANISM: Artificial Sequence
<220> FEATURE:
<223> OTHER INFORMATION: Synthetic polypeptide

<400> SEQUENCE: 161

```
Leu Ser Ser Ile Glu Lys Lys Leu Glu Ile Thr Ser Gln Leu Ile
1               5                   10                  15

Gln Ile Ser Asn Glu Leu Thr Leu Ile Arg Asn Glu Leu Ala Gln Thr
            20                  25                  30

Gly Cys

<210> SEQ ID NO 162
<211> LENGTH: 31
<212> TYPE: PRT
<213> ORGANISM: Artificial Sequence
<220> FEATURE:
<223> OTHER INFORMATION: Synthetic polypeptide

<400> SEQUENCE: 162

Ile Ser Ser Leu Glu Lys Lys Ile Glu Glu Leu Thr Ser Gln Ile Ile
1               5                   10                  15

Gln Leu Ser Asn Glu Ile Thr Leu Leu Arg Asn Glu Ile Ala Gln
            20                  25                  30

<210> SEQ ID NO 163
<211> LENGTH: 31
<212> TYPE: PRT
<213> ORGANISM: Artificial Sequence
<220> FEATURE:
<223> OTHER INFORMATION: Synthetic polypeptide

<400> SEQUENCE: 163

Ile Ser Ser Leu Glu Lys Lys Ile Glu Glu Leu Thr Ser Gln Ile Ile
1               5                   10                  15

Gln Leu Arg Asn Glu Ile Thr Leu Leu Arg Asn Glu Ile Ala Gln
            20                  25                  30

<210> SEQ ID NO 164
<211> LENGTH: 4
<212> TYPE: PRT
<213> ORGANISM: Artificial Sequence
<220> FEATURE:
<223> OTHER INFORMATION: Synthetic peptide

<400> SEQUENCE: 164

Gly Arg Gly Gly
1
```

MULTIMERIC PROTEINS AND METHODS OF MAKING AND USING SAME

RELATED APPLICATIONS

This application claims priority to application Ser. No. 60/306,746, filed Jul. 19, 2001, and application Ser. No. 60/335,425, filed Nov. 30, 2001.

FIELD OF THE INVENTION

The invention relates to engineered polypeptide sequences that mediate formation of oligomers (e.g., dimers, trimers, tetramers, hexamers, pentamers, and higher order olgomeric forms) between molecules attached thereto.

BACKGROUND

Several ways of making multimeric recombinant antibodies have been reported, which include the mini-antibody (Pack et al., *Biotechnology* 11:1271 (1993); Pack et al., *Biochemistry* 31:1579 (1992); Pack et al. *J. Mol. Biol.* 246:28 (1995); Rheinnecker et al., *J. Immunol.* 157:2989 (1996); and Pluckthun and Pack, *Immunotechnology* 3:83 (1997)), diabody-triabody-tetrabody (Hudson P J, *Curr. Opin. Biotech.* 9:395 (1998); Hiades et al., *FEBS Lett.* 409:437 (1997); Kortt et al., *Protein Engineering* 10:423 (1997); and Gall et al., *FEBS Lett.* 453:164 (1999)), protein A-fusion protein (Ito and Kurosawa, J. Biol. Chem. 268:20668 (1993)), streptavidin-fusion protein (Kipriyanov et al., *Protein Engineering* 9:203 (1996)), disulfide-linked fragments (Carter et al., *Biotechnology* 10:163 (1992)), fragments joined with chemically attached spacers (Cook and Wood, *J. Immunol. Methods* 171: 227 (1994)), or post purification assembly of scFv multimers by denaturation and renaturation (Whitlow et al., *Protein Engineering* 7:1017 (1994) and U.S. Pat. No. 5,869,620).

Multimeric antibodies made by fusion with protein A or streptavidin may not be suitable for human use since protein A and streptavidin are highly immunogenic in humans. Linking antibody fragments by a disulfide bond can lead to a dimeric recombinant antibody. It has been reported that single chain antibody scFv-based molecules can sometimes be made in multimeric finals by changing the length of linker between the VH and VL domains in scFv. When the linker is longer than 3 but shorter than 12 amino acid residues, scFv can form dimers, called "diabodies;" when the linker is less than 2 residues, or when no linker residue is used, scFv can form either trimers or tetramers, called "triabodies" and "tetrabodies." Since these multimeric scFv molecules are structurally constrained, little affinity improvement resulted from higher valency. Triabodies have identical or lower affinities than the diabodies, and tetrabodies have less than one fold higher affinity than the diabodies (Kortt et al., *Protein Engineering* 10:423 (1997); and Gall et al., *FEBS Lett.* 453:164 (1999)).

SUMMARY

The invention includes polypeptide sequences capable of conferring multimer formation. In one embodiment, a multimerization polypeptide is selected from the amino acid sequences set forth in SEQ ID NOs: 1 to 7; SEQ ID NOs:9 to 37; and SEQ ID NOs:154 to 163. Multimerization polypeptides also include sequences having various amounts of sequence identity to the sequences disclosed herein, so long as the polypeptide is capable of multimerization. In various embodiments, a polypeptide has 70% or greater, 75% or greater, 80% or greater, 85% or greater, 90% or greater, 95% or greater identity to a multimerization polypeptide, for example, as set forth in any of SEQ ID NOs:1 to 7; SEQ ID NOs:9 to 37; and SEQ ID NOs:154 to 163.

Subsequences, modified forms, e.g., sequences having amino acid substitutions, additions or deletions of the multimerization polypeptides capable of multimerization are also included. In one embodiment, a modified form has one or more amino acid substitutions, provided that all of positions a or d of a seven residue repeat sequence (a.b.c.d.e.f.g), are either leucine, isoleucine or valine, said substituted polypeptide capable of conferring multimerization. In another embodiment, a modified form has one or more amino acid substitutions, provided that one or more positions a or d of a seven residue repeat sequence (a.b.c.d.e.f.g), are either leucine, isoleucine or valine, said substituted polypeptide capable of conferring multimerization. In one aspect, at least one of positions a or d of a seven residue repeat sequence (a.b.c.d.e.f.g), are an amino acid other than leucine, isoleucine or valine. In another aspect, the polypeptide has 1 to 5 amino acid substitutions.

In still another embodiment, a modified form has one or more amino acid substitutions in positions b, c, e, f or g, provided that said substituted polypeptide is capable of conferring multimerization. In one aspect, the polypeptide has 1 to 5 amino acid substitutions.

Multimerization polypeptides are of various lengths. In various embodiments, the polypeptide has a sequence at least 11 amino acids in length, at least 15 amino acids in length, at least 18 amino acids in length, at least 22 amino acids in length, at least 27 amino acids in length, at least 31 amino acids in length. In additional embodiments, the polypeptide has a sequence less than about 125 amino acids in length, less than about 100 amino acids in length, less than about 75 amino acids in length, less than about 50 amino acids in length.

Multimerization polypeptides including subsequences and modified forms thereof may be fused to any molecule thereby conferring multimer formation. In one embodiment, the molecule comprises a polypeptide sequence, e.g., a heterologous polypeptide. In various aspects, the multimerization polypeptide is fused to the amino or carboxy terminus of the heterologous polypeptide, to form a chimeric polypeptide. Chimeric polypeptides have a sequence length typically from about 18-30, 30-50, 50-75, 75-100, 100-150, 150-200, 200-250, 250-500 or 500-1000 amino acids, but may be less or greater. Particular heterologous polypeptides are selected, for example, from: a binding protein (e.g., an antigen binding polypeptide), enzyme, receptor, ligand, nucleic acid binding protein, growth regulatory factor, differentiative factor, and chemotactic factor. In various aspects, the antigen binding polypeptide comprises at least one antibody variable domain, such as a human or humanized variable domain. In additional aspects, the antigen binding polypeptide includes a single chain antibody, Fab, Fab', (Fab')$_2$, or Fv antibody subsequence. In additional aspects, the antigen binding polypeptide comprises a multispecific or multifunctional antibody. In one particular aspect, the antigen binding polypeptide binds to ICAM-1 or an epitope thereof, e.g., the antigen binding polypeptide inhibits human rhinovirus infection of a cell that expresses ICAM-1.

Multimers form hetero- or homo-dimer, -trimer, -tetramer, -pentamer or higher order oligomer. Binding between the monomeric substituents of the multimer may be measured by dissociation, or $K_D$ of the monomers. Various exemplary $K_D$ are $1\times10^{-7}$ or less, $1\times10^{-8}$ or less, or $1\times10^{-9}$.

In additional embodiments, linkers are included between the multimeric polypeptides and the molecule to which it is attached. In one embodiment, a linker comprises a polypeptide sequence, such as a human or humanized amino acid sequence. Linkers can be of any size. For example, a polypeptide linker can be an amino acid sequence from about 5 to 20 amino acids, from about 10 to 30 amino acids, from about 25 to 50 amino acids, from about 30 to 60 amino acids, from about 50 to 75 amino acids, or greater or less in length. In particular aspects, a linker includes an amino acid sequence set forth in any of SEQ ID NO:43 (D30), SEQ ID NO:44 (D35), SEQ ID NO:45 (ED), SEQ ID NO:46 (EDC) or SEQ ID NO:47 (D63), or a subsequence thereof.

The invention also provides pharmaceutical formulations that include the multimers. In one embodiment, a pharmaceutical formulation includes a multimer fused to a molecule. In one aspect, the molecule comprises a heterologus polypeptide sequence.

The invention further provides nucleic acids encoding the multimeric polypeptides alone, and in combination with heterologous polypeptides, as well as linked sequences. Expression cassettes, vectors and cells (e.g., bacterial, fungal, animal, plant, and insect), including the nucleic acids are included.

The invention additionally provides methods of producing a multimerization polypeptide having one or more seven residue repeat sequence, (a.b.c.d.e.f.g), that confers formation of a multimer. In one embodiment, a method includes modifying a polypeptide comprising a seven residue repeat sequence, (a.b.c.d.e.f.g), wherein one or more of positions a or d are replaced with either leucine or isoleucine, thereby producing a multimerization polypeptide that confers multimer formation. In another embodiment, a method includes modifying a seven residue repeat sequence, (a.b.c.d.e.f.g), wherein positions a or d are replaced with valine and either of leucine or isoleucine, thereby producing a multimerization polypeptide that confers dimer formation.

In various aspects, the modified polypeptide forms a trimer, tetramer or pentamer, whereas the unmodified polypeptide forms a dimer; the modified polypeptide forms a tetramer or pentamer, whereas the unmodified polypeptide forms a dimer or trimer; the unmodified polypeptide forms a trimer or tetramer or pentamer. In another aspect, the modified polypeptide has increased or decreased multimer stability in comparison to unmodified polypeptide.

The invention further provides methods of producing a chimeric polypeptide that forms a multimer. In one embodiment, a method includes producing a chimeric polypeptide comprising a multimerization polypeptide comprising a seven residue repeat sequence, (a.b.c.d.e.f.g), wherein one or more of positions a and d are either leucine or isoleucine, fused to a heterologous polypeptide thereby producing chimeric polypeptide that forms a trimer; a tetramer; or a pentamer.

The invention moreover provides methods of producing a molecule that forms a multimer. In one embodiment, a method includes producing a molecule including a multimerization polypeptide comprising a seven residue repeat sequence, (a.b.c.d.e.f.g), wherein positions a or d are valine and either of leucine or isoleucine, fused to the molecule thereby producing a molecule that forms a multimer; e.g., a trimer or tetramer or pentamer.

Further provided are methods of identifying a multimerization polypeptide including a seven residue repeat sequence, (a.b.c.d.e.f.g). In one embodiment, a method includes: incubating a polypeptide comprising a seven residue repeat sequence, (a.b.c.d.e.f.g), wherein one or more of positions a and d are either leucine, isoleucine or valine, under conditions allowing formation of homo- or hetero-multimers; and assaying for the presence of homo- or hetero-multimers of the polypeptide, wherein formation of a homo- or heteromultimer identifies a multimerization polypeptide comprising a seven residue repeat sequence, (a.b.c.d.e.f.g).

Also provided are methods of inhibiting RSV infection of a cell (e.g., in a subject). In one embodiment, a method includes contacting RSV or a cell susceptible to RSV infection with an amount of a hetero- or homo-dimer, -trimer, -tetramer, -pentamer or higher order oligomer with a multimer effective to inhibit RSV infection of the cell. Additionally provided are methods of inhibiting RSV infection, inhibiting RSV progression or treating RSV infection of a subject. In another embodiment, a method includes administering to a subject having or at risk of having RSV infection an amount of a multimer antibody, such as a hetero- or homo-dimer, -trimer, -tetramer or higher order oligomer of an antibody, effective to inhibit, inhibit progression or treat RSV infection of the subject. In various aspects, the subject has or is at risk of having asthma; s a new born or between the ages of 1 to 5, 5 to 10 or 10 to 18; the cell is an epithelial cell; the multimer comprises a chimeric polypeptide, for example, an antibody such as a humanized antibody. In additional aspects, the antibody is administered locally; via inhalation or intranasaly.

Further provided are methods of treating the common cold. In one embodiment, a method includes administering to a subject having or at risk of having a common cold an amount of an antibody, or a hetero- or homo-dimer, -trimer, -tetramer or higher order oligomer of the antibody, effective to treat the common cold in the subject. In various aspects, the treatment comprises inhibiting infection by HRV, progression of HRV infection or a symptom of HRV infection; the antibody is humanized; the antibody is administered locally; the antibody is administered via inhalation or intranasaly; the subject has or is at risk of having asthma; and the subject is a new born or between the ages of 1 to 5, 5 to 10 or 10 to 18.

DETAILED DESCRIPTION

Figure 1:
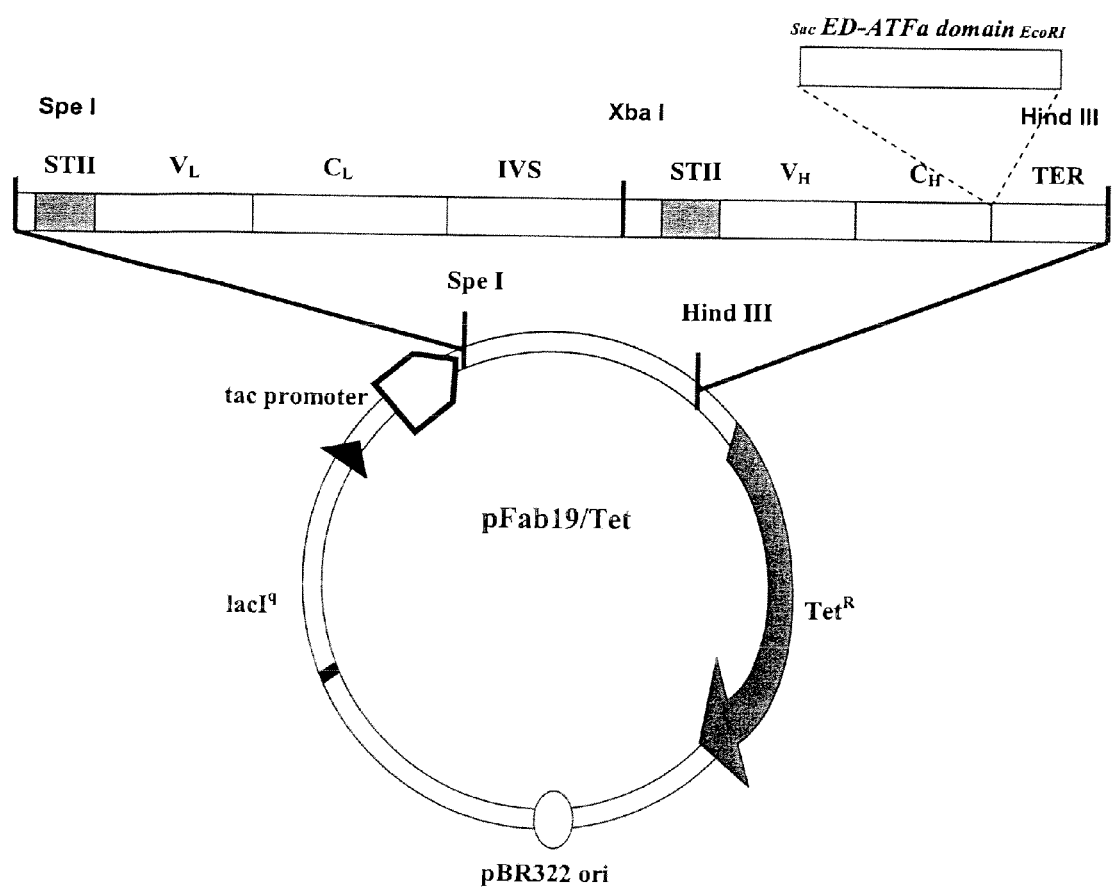
FIG. 1 shows an expression vector ("Fab vector") for expressing exemplary chimeric polypeptide comprising a multimerization domain (ATFα), a linker (ED) and an antibody sequence ($V_L$, $V_H$, $C_L$ and $C_H$), as described in Examples 1-3.

The invention is based, at least in part, on the identification of peptide sequences that confer multimerization, referred to herein as "multimerization polypeptides," "multimerization domains" or "multimerization devices." Invention multimerization polypeptides confer oligomer formation. For example, a multimerization polypeptide, when fused to a second molecule, such as a heterologous polypeptide sequence, facilitates the formation of dimers, trimers, tetramers, pentamers or higher order oligomers or mixtures thereof among the polypeptides. Such invention multimerization polypeptides are useful in a variety of diagnostic or therapeutic applications. For example, fusing a multimerization polypeptide to a binding protein, such as an antigen binding polypeptide (e.g., antibody) can be used to increase the number of antigen binding sites via oligomer formation. Increasing the number of antigen binding sites can in turn increase antibody avidity for the antigen, which is useful in any therapeutic or diagnostic antibody application, particularly where it is desirable or advantageous to increase antibody avidity. A fully human or humanized multimerized antibody has decreased or absent immunogenicity in humans in comparison to non-humanized antibody.

Multimerization polypeptides attached to molecules allow multimers to form between any molecule. In other words, the oligomer may comprise, for example, two or more molecules of the same protein (e.g., a homo-dimer, -trimer, -tetramer or higher oligomer) or a mixture of two or more different (i.e., non-identical) proteins (e.g. a hetero-dimer, -trimer, -tetramer or higher oligomer). For example, oligomeric antibodies may comprise the same antibody or two or more different antibodies, each of which have two or more functions or activities (e.g., hired to two or more epitopes). Such hetero-oligomers, also referred to as multifunctional oligomers (e.g., bifunctional, trifunctional, tetrafunctional, etc., as appropriate) due to the multiple functions of the proteins that comprise the oligomer, are useful in a variety of diagnostic and therapeutic applications. For example, a multifunctional oligomer comprising two or more different antibodies is useful in applications in which it is desired to utilize a multifunctional antibody. In particular, a multifunctional antibody may include an antibody that binds to a cell surface receptor and an antibody that mediates the complement cascade so that cells bearing the receptor are targeted for killing. The specific functionality of the oligomer can be determined by the skilled artisan depending upon the application.

Thus, in accordance with the invention, there are provided multimerization polypeptides that confer multimer formation. In one embodiment, a multimerization polypeptide is selected from any of the amino acid sequences set forth in SEQ ID NOs:1 to 7; SEQ ID NOs:9 to 37; and SEQ ID NOs:154 to 163. In other embodiments, a multimerization polypeptide has 30%, 35%, 40%, 45%, 50%, 55%, 60%, 65%, 70%, 75%, 80%, 85%, 90%, 95%, 96%, 97%, 98%, 99% or greater identity to the amino acid sequences set forth in SEQ ID NOs:1 to 7; SEQ ID NOs:9 to 37; and SEQ ID NOs:154 to 163, provided that the multimerization polypeptide is capable of conferring multimerization. In additional embodiments, a multimerization polypeptide confers formation of hetero- or homo-dimers, trimers, tetramers, pentamers, hexamers, higher order oligomers and mixtures thereof. In yet additional embodiments, a multimerization polypeptide is a sequence that is made fully human or humanized based on the sequence of a human peptide that can form homo- or hetero-dimers, trimers, tetramers, or higher order oligomers.

Multimerization polypeptides and nucleic acids encoding multimerization polypeptides when not fused to heterologous polypeptides are distinct from known wild type leucine zipper sequences. Thus, the multimerization polypeptides of the invention do not include wild type leucine zipper domain sequences known in the art, such as those present in naturally occurring GCN4, ATFα, ATF-7 (100% identical to the coiled-coil domain in ATFα), ATF-2, cyclic AMP response element binding protein Pa (CREB-Pa), JUN-D and C-JUN. The multimerization polypeptides of the invention are also distinct from the multimerization device described in WO 96/37621, wild type sequences derived from human p53, PF4, TSP-4, COMP, thrombospondin, dTAF$_{II}$42, dTAF$_{II}$31, dTAF$_{II}$62, dTAF$_{II}$80, histone 3 and histone 4.

Invention multimerization polypeptides may be of any length provided that they are capable of conferring multimerization. In specific embodiments, a multimerization polypeptide has a sequence at least 11 amino acids in length, at least 15 amino acids in length, at least 18 amino acids in length; at least 22 amino acids in length; at least 25 amino acids in length; at least 29 amino acids in length; and at least 31 amino acids in length. In additional specific embodiments, a multimerization polypeptide has a sequence less than about 100 amino acids in length; less than about 75 amino acids in length; and less than about 50 amino acids in length.

The invention also provides chimeric polypeptides that include a multimerization polypeptide fused to a heterologous polypeptide. Such chimeric polypeptides form oligomers (multimers) via the multimerization polypeptide. In one embodiment, a chimeric polypeptide includes a multimerization polypeptide selected from any of the amino acid sequences set forth in SEQ ID NOs:1 to 7; SEQ ID NOs:9 to 37; and SEQ ID NOs:154 to 163. In other embodiments, a chimeric polypeptide includes a multimerization polypeptide having 30%, 35%, 40%, 45%, 50%, 55%, 60%, 65%, 70%, 75%, 80%, 85%, 90%, 95%, 96%, 97%, 98%, 99% or greater identity to an amino acid sequence set forth in SEQ ID NOs:1 to 7; SEQ ID NOs:9 to 37; and SEQ ID NOs:154 to 163, provided that the chimeric polypeptide forms multimers. In additional embodiments, a chimeric polypeptide fauns hetero- or homo-dimers, trimers, tetramers, pentamers, hexamers, higher order oligomers and mixtures thereof.

As used herein, the term "multimer" and grammatical variations thereof refers to formation of an oligomeric complex between two or more distinct molecules. When used in reference to a polypeptide, e.g., "polypeptide multimer," this means that the polypeptide forms a higher order oligomer with itself (homo-multimer) or with other molecules (hetero-multimer). A polypeptide that confers multimerization means an amino acid sequence that can confer the formation of a dimer, trimer, tetramer, pentamer, hexamers or any higher order oligomer with itself (homo-oligomer) or with one or more different proteins (hetero-oligomer) under appropriate conditions. For example, a chimeric polypeptide comprising a multimerization polypeptide fused to a heterologous polypeptide is able to form dimers, trimers, tetramers, pentamers, hexamers, or higher order oligomers with itself or with different proteins having domains capable of interacting with the multimerization polypeptide portion. Multimers therefore additionally include monovalent or oligomeric (e.g., dimer, trimer, tetramer, etc.) chimeric polypeptides either joined directly or indirectly through covalent or non-covalent binding.

The multimerization polypeptide may be directly linked to the heterologous polypeptide via a covalent bond, such as a chemical cross linking agent. Alternatively, multimerization polypeptide can be connected to the heterologous polypeptide via a linker sequence (e.g., a peptide sequence such as the antibody hinge sequence). Although optional, inclusion of a linker ensures that the multimerization polypeptide does not block function of the heterologous polypeptide and that the heterologous polypeptide does not block multimerization function. A linker thus allows each antigen-binding domain in the multimer enough flexibility to bind antigen.

One specific example of a linker is an immunoglobulin hinge sequence (e.g., IgG or IgD). As with the multimerization domains, linker amino acid sequences may be fully human, humanized or non-human amino acid sequences, unmodified or modified as set forth herein. A fully human or humanized linker sequence may be particularly useful for therapeutic purposes.

Invention compositions comprising a chimeric polypeptide that include a multimerization polypeptide fused to a heterologous polypeptide are distinct from the known native naturally occurring) and recombinant proteins that contain a multimerization polypeptide sequence. For example, scFv fused to yeast based protein GCN4-LI domain, which forms tetravalent scFv (Pack et al., *J. Mol. Biol.* 246:28 (1995)) and scFv fused to wild type leucine zipper domains from jun and fos (U.S. Pat. No. 5,910,573) are distinct from chimeric polypeptide that includes a multimerization polypeptide fused to a heterologous polypeptide. Invention chimeric polypeptides may include multimerization sequences as known in the art, provided that the chimeric polypeptides form multimers and are distinct from known proteins that contain the multimerization sequences known in the art.

As used herein, the term "heterologous," when used in reference to a polypeptide, means that the polypeptide is not normally contiguous with the other polypeptide in its natural environment. Thus, an invention chimeric polypeptide including a multimerization polypeptide fused to a heterologous polypeptide means that the multimerization polypeptide does not exist fused with the heterologous polypeptide in normal cells. In other words, a chimeric polypeptide including a multimerization polypeptide fused to a heterologous polypeptide is a molecule that does not normally exist in nature, i.e., such a molecule is produced by the hand of man, e.g., artificially produced through recombinant DNA technology.

The term "fusion," when used in reference to two or more molecules (e.g., polypeptides) means that the molecules are covalently attached or linked. Any method of attachment of the molecules is contemplated. Thus, the chemical nature of the linkage between the multimer and the molecule to which it is attached is not limited. A particular example for the linkage of two protein sequences is an amide bond or equivalent.

The term "chimera," and grammatical variations thereof, when used in reference to a protein, means that the protein is comprised of one or more amino acid residues from two or more different proteins (i.e., non-identical proteins). A particular example of a chimera containing amino acid residues from two or more different proteins is a polypeptide comprising a multimerization polypeptide and a heterologous polypeptide. A particular example of a chimera containing amino acid residues from three or more different proteins is a polypeptide comprising a multimerization polypeptide, a linker (e.g. hinge) and a heterologous polypeptide.

Although not wishing to be bound by theory, amino acid sequences that confer multimerization mediate protein-protein binding via Van der Waals' forces, hydrophobic interactions, hydrogen bonding or charge-charge bonds. Molecules may also form an oligomer if they are covalently linked to each other. For example, two distinct proteins, chemically synthesized, in vitro translated or isolated or purified from a cell or a sample, may be chemically cross-linked together via a non-amide bond to form an oligomer. Thus, two molecules that exist as separate entities and that do not form oligomers through non-covalent interaction but are joined together via covalent bonds are also considered to be a multimer. Accordingly, an oligomer or a multimer of the invention (e.g., hetero- or homo-dimer, trimer, tetramer, pentamer, hexamers, etc.) may be formed through covalent bonding, non-covalent bonding or mixtures thereof.

The coiled-coil domain is composed of interacting, amphipathic α helices characterized by a seven-residue repeat sequence (a heptad repeat), a.b.c.d.e.f.g, with hydrophobic residues predominant at positions a and d (positions one and four), and polar residues generally elsewhere (Harbury et al., *Science* 262:1401 (1993)). The leucine zipper domains are coiled-coil domains that typically have leucine at the d position of the heptad repeats. Naturally occurring, coiled-coils are typically made up of multiple heptad repeats, for example, three or more sequences, $(a.b.c.d.e.f.g)_1$-$(a.b.c.d.e.f.g)_2$-$(a.b.c.d.e.f.g)_3$, etc. The designation "$(a.b.c.d.e.f.g)_n$," merely refers to two or more additional half (3-4 amino acids) or full length (7 amino acids) heptad repeat sequences, where each half or full (a.b.c.d.e.f.g.) repeat need not have the identical amino acid sequence (see, e.g., Tables 3A and 3B).

Generally the nature of the hydrophobic residues at the a and d positions of the repeat sequence determines its particular multimeric status. Furthermore, with a given pair of a and d residues, the multimerization status may vary and can be affected by the sequence at b, c, e, f and g positions. These rules even apply to the coiled-coil sequences having only 29% to 50% identity with the coiled-coil domain in yeast protein GCN4.

When leucine or isoleucine are at positions a and d as disclosed herein, dimer, trimer or tetramer or pentamer form. Specifically, tetramers are likely to form from coiled-coil sequences that have leucine at position a and isoleucine at position d, as shown by ATFα-LI, ATF1-LI, ATF2-LI, CJUN-LI, JUND-LI and CREB-LI domains. Coiled-coil sequences with isoleucine at position a and leucine at position d may form dimers, such as CREB-IL, CJUN-IL and ATF2-IL, tetramers such as ATFα-IL, or dimers such as ATF1-IL. With leucine at both positions a and d either trimers or tetramers form. For example, ATFα-LL, ATF1-LL, CJUN-LL form trimer, and ATF2-LL and CREB-LL both form tetramers. Coiled-coils with isoleucine at both positions a and d have a tendency to form trimers; for example, ATFα-II and ATF1-II form trimer. These multiple forms exist because amino acids outside the hydrophobic core, positions b, c, e, f, and g, can modulate the multimerization state of the coiled coil by creating a network of inter- and intra-helical hydrogen bonds and salt bridges. This network of hydrophilic bonds changes the relative orientation of the helices as it tends toward optimal geometry, resulting in the observed effect on multimerization state. Accordingly, it is possible in a context dependent manner to change one or a few residues at individual b, c, e, f and g positions to modulate the multimerization state.

When valine is paired with either isoleucine or leucine at a and d position, the resulting multimerization polypeptides tend to be unstable, but can confer mixtures of dimer and tetramer formation. For example, the coiled-coil domain of JUN-D, amino acids 249-280, which has 48% identity to ATFα domain (Table 3B) was modified in accordance with the invention. JUND-LI forms trimer and JUND-LL forms a dimer (Table 8). Similarly, the coiled-coil domain of amino acids 277-308, has 39% identity to ATFα domain. C-JUN-LI forms tetramer, C-JUN-LL forms trimer and C-JUN-IL forms dimer (Table 8).

Generally, multimerization domains with two or more (a.b. c.d.e.f.g.) heptad repeat sequences will tolerate amino acids other than leucine, isoleucine or valine at the a and d positions. For example, in a four heptad repeat sequence, one or more of the a and d positions may be amino acids other than leucine, isoleucine or valine. For example, a single hydrophilic residue may be inserted at an a or d position in a sequence including at least three heptad repeats to modulate the multimerization state. Thus, the invention includes multimerization polypeptides in which the a and d positions in a given heptad repeat sequence may be amino acids other than leucine, isoleucine or valine. Furthermore, the strength of the binding between the monomers that comprise the multimer, also referred to herein as stability or tightness, may be altered by modifying (a.b.c.d.e.f.g.) heptad repeat sequences. For example, replacing an entire interacting layer of a and d residues with residues that can interact through hydrogen bonds, for example, a and d can be replaced by glutamine: CFY196Q: L S S I E K K Q E E Q T S Q L I Q I S N E L T L I R N E L A Q S (SEQ ID NO:37). Thus, the invention includes multimerization polypeptides in which the a, b, c, d, e, f and g positions may be modified to alter the multimerization state as well as increase or decrease the strength of binding between the multimers.

Each of the multimeric domains derived from coiled-coil sequences may exist as mixtures of monomer, dimer, trimer, tetramer or higher oligomer. The major multimeric form, which constitutes over 50% of the mass, is the designated multimer form. For example, if a multimer is designated a tetramer, at least 50% of the mass is in the tetrameric form.

Specific examples of multimerization polypeptides of the invention include, for example, SEQ ID NOs: 1 to 7; SEQ ID NOs:9 to 37; and SEQ ID NOs:154 to 163. Additional multimerization polypeptides may be identified by assaying putative coiled-coil sequences, composed of one or more heptad repeats (a.b.c.d.e.f.g) for oligomer formation using routine detection assays as set forth herein or known in the art (see, e.g., Example 6). A sequence including a heptad repeat, (a.b. c.d.e.f.g), wherein one or more positions a and d are either leucine, isoleucine or valine can be incubated under conditions allowing formation of a hetero- or homo-oligomer.

For example, the leucine zipper domain of cAMP response element binding protein-Pa (CREB-Pa, amino acids 393-424) is 74% identical to ATFα leucine zipper domain sequence (Table 3C). Variants of CREB-Pa leucine zipper domain, CREB-LL and CREB-LI, formed tetramers and CREB-IL formed dimer (Table 8). ATF-1 leucine zipper domain (amino acids 238-269) is 29% identical to ATFα leucine zipper domain sequence. Variants of ATF-1 leucine zipper domain, ATF1-LI form tetramers; ATF1-IL, ATF1-LL and ATF1-II all form trimers (Table 8).

Additional multimerization domains can be produced by first identifying a wild type coiled-coil domain. For example, five leucine zipper domains were identified by searching the public database (Table 3B). These domains show 32% to 77% identity to the ATFα leucine zipper domain, and less than 50% identity to GCN4 leucine zipper domain (Table 3C). The wild type residues at positions a and d were replaced with leucine or isoleucine (Table 3D). Additional coiled-coil domains that may be modified in accordance with the invention, include, for example, three and four helix bundles such as lung surfactant D protein, tetranectin, and mannose binding protein; and ROP, cytochrome B562, and tetrabrachion stalk, respectively.

Other multimerization domains can therefore be identified by comparison to sequence databases, and mutating the sequence as set forth herein. For example, one or more coiled-coil forming sequences may be selected from the protein database (e.g., GEN-BANK, SWISS-PROT) and isoleucine, leucine or valine may be introduced into one or more a or d positions of the heptad repeats to alter the multimerization status of the sequence. The multimerization state may be determined using the assays described herein (Example 6). Optionally, the heptad repeat may be substituted with one or more point mutations, additions, or deletions at positions b, c, e, f and g where the additional mutations are selected to modulate or stabilize the multimeric state that is formed, that is, to alter the type of multimer formed, e.g., trimer vs. tetramer, or to modulate the binding strength between the monomers that form the multimer. Thus, one or more positions b, c, e, f and g may be modified alone or in combination with modifications at one or more a or d positions.

Specific examples of such mutations include those that make additional interhelical hydrogen bonds or salt bridges, for example, between e and g positions of a four helix bundle. The mutations can also be selected by considering the effect of change on the network of hydrophilic bonds on the surface of the domain. Inspection of the hydrophilic bonding network is generally predictive but multimer status can be confirmed using the multimerization assays described herein (Example 6).

If the multimerization state has been increased by the modification, for example, the modified sequence forms a trimer or tetramer or higher order oligomer instead of a dimer, it may be desired to substitute one or more hydrophobic residues at positions b, c, e, f and g to hydrophilic residues to facilitate proper hydrophobic interface formation (Example 12) to increases tightness or stability of the multimer. Because helix formation is at least in part dependent on the residues immediately preceeding and following the helix, one or more residues may be added at the helix's N or C terminus, or at the N or C terminus of the series of heptad repeat sequences to improve stability or tightness of the multimer. The phrase to increase or improve "tightness" or "stability" means that the multimer formed is less likely to dissociate into its constituent monomers. A general approximation of multimer tightness or stability can be assessed by the narrowness or broadness of the peak formed in sedimentation velocity studies. Tightness or stability can also be assayed, for example, by denaturing the multimer formed while simultaneously monitoring circular dichroism. A specific example of such a modification is the addition of a terminal serine (Example 11).

Thus, the invention provides methods of producing a multimerization polypeptide comprising one or more seven residue coiled-coil, or leucine zipper repeat sequence, (a.b.c. d.e.f.g). In one embodiment a method includes producing a polypeptide comprising a coiled-coil sequence, (a.b.c. d.e.f.g), wherein positions a and d are replaced with either leucine or isoleucine, thereby producing a multimerization polypeptide that confers dimer, trimer, tetramer or pentamer formation. In another embodiment, a method includes producing a coiled-coil sequence, (a.b.c.d.e.f.g), wherein positions a or d are replaced with valine and either of leucine or isoleucine or valine, thereby producing a multimerization polypeptide that confers dimer and tetramer formation. In yet another embodiment, a method includes synthesizing a coiled-coil sequence, (a.b.c.d.e.f.g), wherein positions a and d are either leucine or isoleucine or valine to produce a multimerization polypeptide that confers dimer, trimer or tetramer formation. In still another embodiment, a method includes synthesizing a coiled-coil sequence, (a.b.c.d.e.f.g), wherein positions a or d are valine and either of leucine or isoleucine to produce a multimerization polypeptide that confers dimer and tetramer formation. In additional embodiments, where there are multiple (a.b.c.d.e.f.g), repeats, positions a or d are replaced such that they are predominantly (e.g., greater than 50%) either leucine, isoleucine or valine. In further embodiments, one or more positions b, c, e, f and g are replaced, e.g., one or more hydrophobic residues are substituted with hydrophilic residues. In yet further embodiments, one or more amino acids are added to the N- or C-terminus of the multimerization domain or flanking a heptad repeat within the domain.

The invention also provides methods of identifying multimerization polypeptides comprising a coiled-coil sequence, (a.b.c.d.e.f.g), wherein positions a or d are either leucine, isoleucine or valine. In one embodiment, a method includes, incubating a polypeptide comprising a coiled-coil sequence, (a.b.c.d.e.f.g), wherein positions a or d are either leucine, isoleucine or valine, under conditions allowing formation of homo- or hetero-multimers, and assaying for the presence of homo- or hetero-multimers of the polypeptide. Formation of a homo- or hetero-multimer identifies the polypeptide as a multimerization polypeptide. In various aspects, where there are multiple (a.b.c.d.e.f.g), repeats, positions a or d are predominantly either leucine, isoleucine or valine. In another aspect, the polypeptide comprises a heterologous polypeptide fused to a polypeptide comprising the coiled-coil sequence, (a.b.c.d.e.f.g). In another aspect, the polypeptide contains a linker between the heterologous polypeptide and the polypeptide comprising the coiled-coil sequence, (a.b.c. d.e.f.g). In yet another aspect, the homo- or hetero-multimer that is detected is a dimer, trimer, tetramer, pentamer, hexamer, or higher order oligomer.

The terms "protein," "polypeptide" and "peptide" are used interchangeably herein to refer to two or more contiguous amino acids, also referred to as "residues," covalently linked through an amide bond or equivalent. Proteins are of unlimited length and may be comprised of L- or D-amino acids as well as mixtures thereof. Amino acids may be linked by non-natural and non-amide chemical bonds including, for example, those formed with glutaraldehyde, N-hydroxysuccinimide esters, bifunctional maleimides, or N,N'-dicyclohexylcarbodiimide (DCC). Non-amide bonds include, for example, ketomethylene, aminomethylene, olefin, ether, thioether and the like (see, e.g., Spatola (1983) in *Chemistry and Biochemistry of Amino Acids, Peptides and Proteins*, Vol. 7, pp 267-357, "Peptide and Backbone Modifications," Marcel Decker, N.Y.).

Polypeptides may have one or more cyclic structures such as an end-to-end amide bond between the amino and carboxy-terminus of the molecule or intra- or inter-molecular disulfide bond. Polypeptides may be modified in vitro or in vivo, e.g., post-translationally modified to include, for example, sugar residues, phosphate groups, ubiquitin, fatty acids or lipids. Polypeptides further include amino acid structural and functional analogues, for example, peptidomimetics having synthetic or non-natural amino acids or amino acid analogues.

The term "antibody" refers to a protein that binds to other molecules (antigens) via heavy and light chain variable domains, $V_H$ and $V_L$, respectively. Antibodies include IgG, IgD, IgA, IgM and IgE. The antibodies may be intact immunoglobulin molecules, two full length heavy chains linked by disulfide bonds to two full length light chains, as well as subsequences (i.e. fragments) of immunoglobulin molecules, with our without constant region, that bind to an epitope of an antigen, or subsequences thereof (i.e. fragments) of immunoglobulin molecules, with or without constant region, that bind to an epitope of an antigen. Antibodies may comprise full length heavy and light chain variable domains, $V_H$ and $V_L$, individually or in any combination.

Polypeptide sequences can be made using recombinant DNA technology of polypeptide-encoding nucleic acids via cell expression or in vitro translation, or chemical synthesis of polypeptide chains using methods known in the art. Antibodies and subsequences can be expressed from recombinantly produced antibody-encoding nucleic acid, such as a polynucleotide isolated from hybridoma cells or selected from a library of naturally occurring or synthetic antibody genes (see, e.g., Harlow and Lane, *Antibodies: A Laboratory Manual*, Cold Spring Harbor Laboratory, 1989; Harlow and Lane, *Using Antibodies: A Laboratory Manual*, Cold Spring Harbor Laboratory, 1999; Fitzgerald et al., *J.A.C.S.* 117:11075 (1995); Gram et al., *Proc. Natl. Acad. Sci. USA* 89:3576 (1992)). Polypeptide sequences can also be produced by a chemical synthesizer (see, e.g., Applied Biosystems, Foster City, Calif.).

The term "multifunctional" means that the composition referred to has two or more activities or functions (e.g., bifunctional, trifunctional, tetrafunctional, etc.). For example, a multifunctional polypeptide has two or more of antigen binding, enzyme activity, ligand or receptor binding, toxin, etc.). Similarly, a multifunctional oligomer comprises a mixture of two or more polypeptides each having at least one function or activity, such as antigen binding and enzyme activity, ligand or receptor binding, toxin, etc.

An antibody that binds to a particular antigen, and which also has an attached polypeptide with enzyme activity (e.g., luciferase, acetyltransferase, galactosidase, peroxidase, etc.) is one particular example of a bifunctional antibody, Candidate functions for multifunctional oligomers other than antigen binding and in addition to enzyme activity include, for example, detectable domains such as immunoglobulin, T7 and polyhistidine amino acid sequences, toxins (e.g., ricin, cholera, pertussis), cell surface proteins such as receptors, ligands (substrates, agonists and antagonists), adhesion proteins (e.g., streptavidin, avidin, lectins), growth factors, differentiative factors, chemotactic factors and proenzymes.

Multifunctional multimers further include multispecific (e.g., bispecific, trispecific, tetraspecific, etc.) compositions. The term "multispecific" means an antigen binding polypeptide (e.g., an antibody) that binds to different antigenic epitopes. The different epitopes may be present on the same antigen or on different antigens. For example, a multispecific antibody oligomer comprises a mixture of two or more antibodies each having different epitope binding specificity. Multispecific oligomers may be comprised of individual antigen binding polypeptides each of which have distinct variable domains. For example, one of the antigen binding polypeptides of the oligomer may have two variable domains each of which recognize a different epitope.

Multifunctional polypeptides can be produced through chemical crosslinking of the selected molecules (which have been produced by synthetic means or by expression of nucleic acid that encodes the polypeptides) or through recombinant DNA technology combined with in vitro, or cellular expression of the polypeptide, and subsequent oligomerization. Multispecific antibodies can be similarly produced through recombinant technology and expression, fusion of hybridomas that produce antibodies with different epitopic specificities, or expression of multiple nucleic acid encoding antibody variable chains with different epitopic specificities in a single cell.

A specific example of a bispecific antibody is illustrated in FIGS. 6A and 6B. The CREB-IL multimerization polypeptide is positioned at the center of a molecule linking Fab from two different antibodies producing a tetravalent binding antibody. Use of multimeric polypeptides conferring trimer or tetramer formation would produce hexavalent and octavalent molecules, respectively. The Fab moieties in the bispecific protein can have different specificities. A flexible linker (e.g., hinge) sequence can be used to join the Fab portion of each protein. The exemplary bispecific antibody polypeptide may be produced from one tricistronic RNA molecule (FIG. 6B).

As used herein, the term "subsequence" or "fragment" means a portion of the full length molecule. For example, a subsequence of a multimerization polypeptide is one or more amino acids less in length than full length polypeptide (e.g. one or more internal or terminal amino acid deletions from either amino or carboxy-termini). Subsequences therefore can be any length up to the full length molecule.

Specific examples of antibody subsequences include, for example, chimeric polypeptides in which a heterologous domain comprises an Fab, Fab', (Fab')$_2$, Fv, or single chain antibody (SCA) fragment (e.g., scFv). Subsequences include portions, which retain at least part of the function or activity of full length sequence. For example, an antibody subsequence will retain the ability to selectively bind to an antigen even though the binding affinity of the antibody subsequence may be greater or less than the binding affinity of the full length antibody.

For antibody subsequences, pepsin or papain digestion of whole antibodies can be used to generate antibody fragments. In particular, an Fab fragment consists of a monovalent antigen-binding fragment of an antibody molecule, and can be produced by digestion of a whole antibody molecule with the enzyme papain, to yield a fragment consisting of an intact light chain and a portion of a heavy chain. An (Fab')$_2$ fragment of an antibody can be obtained by treating a whole antibody molecule with the enzyme pepsin, without subsequent reduction. An Fab' fragment of an antibody molecule can be obtained from (Fab')$_2$ by reduction with a thiol reducing agent, which yields a molecule consisting of an intact light chain and a portion of a heavy chain. Two Fab' fragments are obtained per antibody molecule treated in this manner.

An Fv fragment is a fragment containing the variable region of a light chain $V_L$ and the variable region of a heavy chain $V_H$ expressed as two chains. The association may be non-covalent or may be covalent, such as a chemical crosslinking agent or an intermolecular disulfide bond (Inbar et al., Proc. Natl. Acad Sci. USA 69:2659 (1972); Sandhu, Crit. Rev. Biotech. 12:437 (1992)).

A single chain antibody ("SCA") is a genetically engineered or enzymatically digested antibody containing the variable region of a light chain $V_L$ and the variable region of a heavy chain, linked by a flexible linker, such as a polypeptide sequence, in either $V_L$-linker-$V_H$ orientation or in $V_H$-linker-$V_L$ orientation. Alternatively, a single chain Fv fragment can be produced by linking two variable domains via a disulfide linkage between two cysteine residues. Methods for producing scFv antibodies are described, for example, by Whitlow et al., In: Methods: A Companion to Methods in Enzymology 2:97 (1991); U.S. Pat. No. 4,946,778; and Pack et al., Bio/Technology 11:1271 (1993). Other methods of producing antibody subsequences, such as separation of heavy chains to form monovalent light-heavy chain fragments, further cleavage of fragments, or other enzymatic, chemical, or genetic techniques may also be used, provided that the subsequences bind to the antigen to which the intact antibody binds.

As used herein, the term "bind" or "binding" means that the compositions referred to have affinity for each other. "Specific binding" is where the binding is selective between two molecules. A particular example of specific binding is that which occurs between an antibody and an antigen. Typically, specific binding can be distinguished from non-specific when the dissociation constant ($K_D$) is less than about $1 \times 10^{-5}$ M or less than about $1 \times 10^{-6}$ M or $1 \times 10^{-7}$ M. Specific binding can be detected, for example, by ELISA, immunoprecipitation, coprecipitation, with or without chemical crosslinking, two-hybrid assays and the like. Appropriate controls can be used to distinguish between "specific" and "non-specific" binding.

Full length antibodies, subsequences (e.g., single chain forms) or modified forms, fully human, humanized or non-human may be present as heteromeric or homomeric dimers, trimers, tetramers, pentamers, hexamers or any higher order oligomer that retains at least a part of the antigen binding activity of the monomer. Antibody multimers include oligomeric (e.g., dimer, trimer, tetramer, etc.) combinations of different antibodies that are multispecific (e.g., bispecific, trispecific, tetraspecific, etc.) or multifunctional (e.g., bifunctional, trifunctional, tetrafunctional, etc.).

The invention further provides linker polypeptide sequences. The invention linker sequences can be fused to a heterologous polypeptide to form a chimeric polypeptide. In one embodiment, a linker comprises a portion of a hinge region from an immunoglobulin. In one aspect, a linker is derived from or modeled after a human or humanized immunoglobulin. In particular aspects, a linker sequence comprises a portion of an immunoglobulin hinge region selected from an amino acid sequence set forth in any of (SEQ ID NO:43 (D30), SEQ ID NO:44 (D35), SEQ ID NO:45 (ED), SEQ ID NO:46 (EDC) or SEQ ID NO:47 (D63)). In additional particular aspects, a linker sequence comprises an amino acid sequence from about 2 to 20 amino acids, from about 5 to 10 amino acids, from about 10 to 30 amino acids, from about 25 to 50 amino acids, from about 30 to 60 amino acids, from about 50 to 75 amino acids. In further particular aspects, a linker sequence comprises an amino acid sequence from about 2 to 20 amino acids, from about 5 to 10 amino acids, from about 10 to 30 amino acids, from about 25 to 50 amino acids, from about 30 to 60 amino acids, from about 50 to 75 amino acids, from about 75 to 100 amino acids and which includes an amino acid sequence set forth in any of (SEQ ID NO:43 (D30), SEQ ID NO:44 (D35), SEQ ID NO:45 (ED), SEQ ID NO:46 (EDC) or SEQ ID NO:47 (D63)).

As used herein, "linker" or "spacer" refers to a molecule or group of molecules that connects two or more molecules to each other. A flexible linker between two molecules joined to each other allows enough free rotation of one or more of the molecules so that the molecules do not block each others' function. For example, a linker such as an amino acid sequence located between a multimerization polypeptide and a heterologous polypeptide of a chimeric polypeptide, e.g., a humanized antibody, allows the antibody to bind to antigen without significant steric interference from other multimers within the oligomer.

Thus, the invention also provides chimeric polypeptides including a multimerization polypeptide fused to a heterologous polypeptide that further include a linker polypeptide between the multimerization polypeptide and heterologous polypeptide. Also provided are chimeric polypeptides comprising linker sequences fused to a heterologous sequence.

Polypeptides of the invention, including multimerization polypeptides, chimeric polypeptides oligomers, and linkers, include modified forms such as sequences having one or more amino acid substitutions, additions or deletions (i.e., subsequences), provided the modification does not destroy function. The term "modification" therefore denotes an alteration of the molecule that does not destroy an activity or function of the modified molecule. A modified multimerization polypeptide will therefore retain, for example, at least in part, the ability to form oligomers, even if the oligomers formed are less stable due to decreased affinity, e.g., form dimers instead of trimers, form trimers instead of tetramers, etc. A modified heterologous polypeptide will retain at least a part of one or more functions or activities associated with the polypeptide (e.g., protein binding activity, enzyme activity, ligand activity, nucleic acid binding activity, growth regulatory activity, cell differentiative activity, or chemotactic activity). For example, a chimeric polypeptide that includes a modified antibody sequence, such as an antibody subsequence or antibody having one or more amino acid additions or insertions will retain, at least in part, antigen binding capability.

Modifications therefore include amino acid additions, insertions, deletions and substitutions, for example. An example of an addition is where one or more amino acids are added to the N- or C-terminal end multimerization polypeptide. An example of an insertion is where an amino acid is inserted into the sequence. An example of a deletion is where one or more amino acids are deleted from the N- or C-terminal end, or internally within the sequence.

Modifications may improve an activity or function of the modified molecule or provide a distinct functionality. For example, affinity of a multimerization polypeptide may be increased by addition of all or a portion of a heptad repeat sequence (e.g., a half turn). Addition of a heptad repeat sequence, or a portion of a heptad repeat sequence may also change the oligomer from forming dimer to trimer or tetramer formation.

Exemplary multimerization polypeptides are set forth, for example, in SEQ ID NOs:1 to 7; SEQ ID NOs:9 to 37; and SEQ ID NOs:154 to 163, each contain 4 and one-half heptad repeat sequences (see Table 3A). These and other heptad containing sequences may therefore be modified. For example, full length (7 amino acids) or half (3 to 4 amino acids of the motif) heptad repeat sequences may be added.

Alternatively, it may be desirable to shorten the multimerization polypeptide, in which case one or more amino acid residues may be deleted from a multimerization polypeptide without destroying multimerization function. Thus, multimerization polypeptides of the invention, including exemplary multimerization polypeptides set forth in SEQ ID NOs:1 to 7; SEQ ID NOs:9 to 37; and SEQ ID NOs:154 to 163, may be modified to delete half (3 to 4 amino acids) or full (7 amino acids) length heptad repeat, for example.

Exemplary amino acid substitutions include conservative amino acid substitutions. The term "conservative substitution" means the replacement of one amino acid by a biologically or chemically similar residue. Biologically similar means that the substitution is compatible with biological activity, for a multimerization polypeptide, oligomer formation. Particular examples of conservative substitutions include the substitution of one hydrophobic residue, such as isoleucine, valine, leucine or methionine for another, or the substitution of one polar residue for another, such as the substitution of arginine for lysine, glutamic for aspartic acids, or glutamine for asparagine, serine for threonine, and the like.

In one embodiment, a multimerization polypeptide has 1-3, 3-5 or 5-10 amino acid substitutions, provided that positions a (one) or d (four) of a coiled-coil heptad repeat sequence, (a.b.c.d.e.f.g), are either leucine, isoleucine or valine, and that the substituted polypeptide be capable of multimerization. In one aspect, where there are multiple heptad repeat sequences, positions a and d are predominantly either leucine, isoleucine or valine. In another aspect, a multimerization polypeptide has 1-3, 3-5 or 5-10 amino acid substitutions at positions b, c, e, f or g, e.g., to modulate the type of multimer that forms or to modulate the stability or tightness of the multimer formed. In yet another aspect, one or more of the amino acid substitutions are conservative amino acid substitutions. In still another aspect, the substitution is with a human amino acid.

Modifications also include derivatized sequences, for example, amino acids in which free amino groups form amine hydrochlorides, p-toluene sulfonyl groups, carbobenzoxy groups; the free carboxy groups from salts, methyl and ethyl esters; free hydroxyl groups that form O-acyl or O-alkyl derivatives, as well as naturally occurring amino acid derivatives, for example, 4-hydroxyproline, for proline, 5-hydroxylysine for lysine, homoserine for serine, ornithine for lysine, etc. Also included are modifications that confer covalent bonding, for example, a disulfide linkage between two cysteine residues thereby producing a cyclic polypeptide. Modifications can be produced using any of a variety of methods well known in the art (e.g., PCR based sited-directed, deletion and insertion mutagenesis, chemical modification and mutagenesis, chemical cross-linking, etc.).

Modifications also include addition of functional entities such as tags (e.g., polyhistidine, T7, immunoglobulin, etc.), gold particles, covalently or non-covalently attached to the multimerization polypeptide, chimeric polypeptide or oligomers. Thus, the invention provides modified polypeptides having one or more activities (e.g., retain at least part of multimer activity, antigen binding activity, etc.) of unmodified polypeptide. Modifications include radioactive and non-radioactive detectable labels attached to or incorporated into the molecule.

The term "identical" or "identity" means that two or more referenced entities are the same. Thus, where two polypeptide sequences are identical, they have the same amino acid sequence. "Areas of identity" means that a portion of two or more referenced entities are the same. Thus, where two polypeptide sequences are identical over one or more parts of their sequence, they share identity in these areas. The term "substantial identity" means that the identity is structurally or functionally significant. That is, the identity is such that the molecules are structurally identical or perform the same function (e.g., biological function) even though the molecules differ. Due to variation in the amount of sequence conservation between structurally and functionally related proteins, the amount of sequence identity for molecules having substantial identity will depend upon the type of region/domain and its function. For nucleic acid sequences, 50% sequence homology and above may constitute substantial identity. Substantial homology for proteins can be significantly less, for example, as little as 30% sequence identity, but typically is more, e.g., 50%, 60%, 75%, 85% or more.

The extent of identity between two sequences can be ascertained using various computer programs and mathematical algorithms known in the art. Such algorithms that calculate percent sequence identity (homology) generally account for sequence gaps and mismatches over the comparison region. For example, a BLAST (e.g., BLAST 2.0) search algorithm (see, e.g., Altschul et al., *J. Mol. Biol.* 215:403 (1990), publicly available through NCBI at http://www.ncbi.nlm.nih.gov) has exemplary search parameters as follows: Mismatch −2; gap open 5; gap extension 2. For polypeptide sequence comparisons, a BLASTP algorithm is typically used in combination with a scoring matrix, such as PAM100, PAM 250, BLOSUM 62 and the like.

As used herein, the term "isolated," when used as a modifier of invention compositions (e.g., multimerization polypeptides, chimeras, linkers, antibodies, subsequences, modified forms, nucleic acids encoding same, cells, vectors, etc.), means that the compositions are made by the hand of man and are separated from their naturally occurring in vivo environment. Generally, compositions so separated are substantially free of one or more materials with which they normally associate with in nature, for example, one or more protein, nucleic acid, lipid, carbohydrate, cell membrane. An "isolated" polypeptide can also be "substantially pure" when free of most or all of the materials with which it normally is associated in nature. Thus, an isolated polypeptide that also is substantially pure does not include polypeptides or polynucleotides present among millions of other sequences, such as antibodies of an antibody library or nucleic acids in a genomic or cDNA library, for example. Purity can be at least about 60% or more by mass. The purity can also be about 70% or 80% or more, and can be greater, for example, 90% or more. Purity can be determined by any appropriate method, including, for example, UV spectroscopy, mass spectroscopy, chromatography (e.g., HPLC, gas phase), gel electrophoresis (e.g., silver or coomassie staining) and sequence analysis (nucleic acid and peptide).

The invention also provides nucleic acids encoding invention polypeptides, including multimerization polypeptides, chimeras, linkers, subsequences, modified forms and multimers thereof. In various embodiments, a nucleic acid encodes a polypeptide set forth in SEQ ID NOs:1 to 7; SEQ ID NOs:9 to 37; or SEQ ID NOs:154 to 163. In additional embodiments, a nucleic acid encodes a chimeric polypeptide comprising a sequence set forth in any of (SEQ ID NOs:1 to 36 and SEQ ID NOs:154 to 163), fused to a heterologous domain. In another embodiment, a nucleic acid sequence encodes (SEQ ID NO:43 (D30), SEQ ID NO:44 (D35), SEQ ID NO:45 (ED), SEQ ID NO:46 (EDC) or SEQ ID NO:47 (D63)).

As used herein, a "nucleic acid" refers to at least two or more ribo- or deoxy-ribonucleic acid base pairs that are linked through a phosphodiester bond or equivalent. Nucleic acids include polynucleotides and polynucleosides. Nucleic acids include single, double or triple, circular or linear molecules. A nucleic acid molecule may belong exclusively or in a mixture to any group of nucleotide-containing molecules, as exemplified by, but not limited to, the following groups of nucleic acid molecules: RNA, DNA, cDNA, genomic nucleic acids, non-genomic nucleic acids, naturally occurring and non naturally occurring nucleic acids and synthetic nucleic acids. This includes, by way of example, nucleic acids associated with any organelle, such as the mitochondria, ribosomal RNA, and nucleic acid molecules comprised chimerically of one or more components that are not naturally occurring along with naturally occurring components.

Additionally, a "nucleic acid molecule" may contain in part one or more non-nucleotide-based components as exemplified by, but not limited to, amino acids and sugars. Thus, by way of example, but not limitation, a ribozyme that is in part nucleotide-based and in part protein-based is considered a "nucleic acid molecule."

Nucleic acids can be of any length. Nucleic acid lengths typically range from about 20 to 10 Kb, 10 to 5 Kb, 1 to 5 Kb or less, 1000 to about 500 base pairs or less in length. Nucleic acids can also be shorter, for example, 100 to about 500 base pairs, or from about 12 to 25, 25 to 50, 50 to 100, 100 to 250, or about 250 to 500 base pairs in length.

As a result of the degeneracy of the genetic code, nucleic acids include sequences and subsequences degenerate with respect to nucleic acids that encode (SEQ ID NO:1 to 7, SEQ ID NOs:9 to 37, SEQ ID NOs:154 to 163, SEQ ID NO:43 (D30), SEQ ID NO:44 (D35), SEQ ID NO:45 (ED), SEQ ID NO:46 (EDC) or SEQ ID NO:47 (D63)). Nucleic acids also include sequences set forth in Tables 1, 2 and 4, sequences complementary thereto and subsequences thereof. Such nucleic acids are useful for hybridization to detect the presence or an amount of chimeric polypeptide in a sample (in vitro, cell, culture medium, tissue or organ, serum, in a subject, etc.).

Nucleic acids of the invention can be produced using various standard cloning and chemical synthesis techniques. Such techniques include, but are not limited to: 1) nucleic acid amplification, e.g., polymerase chain reaction (PCR), with genomic DNA or cDNA targets, using primers (e.g., a degenerate primer mixture) capable of annealing to antibody sequence; 2) chemical synthesis of nucleic acid sequences which can then be cloned into a plasmid, propagated amplified and purified and; 3) computer searches of databases for related sequences. Purity of nucleic acids can be determined through sequencing, gel electrophoresis and the like.

The invention further provides expression cassettes comprising a nucleic acid encoding a chimeric polypeptide operably linked to an expression control element. As used herein, the term "operably linked" refers to a physical or a functional relationship between the elements referred to that permit them to operate in their intended fashion. Thus, an expression control element "operably linked" to a nucleic acid means that the control element modulates transcription and as appropriate, translation of the transcript.

There need not be physical linkage to nucleic acid in order to control expression. Thus, physical linkage is not required for the elements to be operably linked. For example, a minimal element can be linked to a nucleic acid encoding a chimeric polypeptide. A second element that controls expression of an operably linked nucleic acid encoding a protein that functions "in trans" to bind to the minimal element can influence expression of the chimeric polypeptide. Because the second element regulates expression of chimeric polypeptide, the second element is operably linked to the nucleic acid encoding the chimeric polypeptide.

The term "expression control element" refers to nucleic acid that influences expression of an operably linked nucleic acid. Promoters and enhancers are particular non-limiting examples of expression control elements. A "promotor sequence" is a DNA regulatory region capable of initiating transcription of a downstream (3' direction) coding sequence. The promoter sequence includes a minimum number of bases necessary to initiate transcription. Enhancers also regulate gene expression but can function a distance from the transcription start site of the gene to which it is operably linked. Enhancers also function at either 5' or 3' ends of the gene, as well as within the gene (e.g., in introns or coding sequences).

An expression control element can confer expression in a manner that is "constitutive," such that transcription of the operably linked nucleic acid occurs without the presence of a signal or stimuli. Expression control elements can confer expression in a manner that is "regulatable," that is, a signal or stimuli increases or decreases expression of the operably linked nucleic acid. A regulatable element that increases expression of the operably linked nucleic acid in response to a signal or stimuli is also referred to as an "inducible element." A regulatable element that decreases expression of the operably linked nucleic acid in response to a signal or stimuli is referred to as a "repressible element" (i.e., the signal decreases expression such that when the signal, is removed or absent, expression is increased).

Expression control elements include elements active in a particular tissue or cell type, referred to herein as a "tissue-specific expression control element." Tissue-specific expression control elements are typically active in specific cell or tissue because they are recognized by transcriptional activator proteins, or other regulators of transcription, that are unique to a specific cell or tissue type.

Expression control elements additionally include elements that confer expression at a particular stage of the cell cycle or differentiation. Accordingly, the invention further includes expression control elements that confer constitutive, regulatable, tissue-specific, cell cycle specific, and differentiation stage specific expression.

Expression control elements include full-length nucleic acid sequences, such as native promoter and enhancer elements, as well as subsequences or nucleotide variants thereof (e.g., substituted/mutated or other forms that differ from native sequences) which retain all or part of full-length or non-variant control element function (confer regulation, e.g., retain some amount of inducibility in response to a signal or stimuli).

For bacterial systems, constitutive promoters such as T7 and the like, as well as inducible promoters such as pL of bacteriophage λ, plac, ptrp, ptac (ptrp-lac hybrid promoter) may be used. In insect cell systems, constitutive or inducible promoters (e.g., ecdysone) may be used. In yeast, constitutive or inducible promoters may be used (see, e.g., Ausubel et al., In: *Current Protocols in Molecular Biology*, Vol. 2, Ch. 13, ed., Greene Publish. Assoc. & Wiley Interscience (1988); Grant et al., In: *Methods in Enzymology*, 153, 516-544 (1987), eds. Wu & Grossman, 31987, Acad. Press, N.Y.; Glover, *DNA Cloning*, Vol. II, Ch. 3, IRL Press, Wash., D.C. (1986); Bitter In: *Methods in Enzymology*, 152, 673-684 (1987), eds. Berger & Kimmel, Acad. Press, N.Y.; and, Strathern et al., *The Molecular Biology of the Yeast Saccharomyces* Cold Spring Harbor Press, Vols. I and II (1982)). A constitutive yeast promoter such as ADH or LEU2 or an inducible promoter such as GAL may be used (R. Rothstein In: *DNA Cloning, A Practical Approach*, Vol. 11, Ch. 3, ed. D. M. Glover, IRL Press, Wash., D.C. (1986)).

For mammalian cells, constitutive promoters of viral or other origins may be used. For example, SV40, or viral long terminal repeats (LTRs) and the like, or inducible promoters derived from the genome of mammalian cells (e.g., metallothionein IIA promoter; heat shock promoter, steroid/thyroid hormone/retinoic acid response elements) or from mammalian viruses (e.g., the adenovirus late promoter; the inducible mouse mammary tumor virus LTR) can be used for expression.

The invention also provides transformed cells and progeny thereof into which nucleic acids encoding invention polypeptides have been introduced by means of recombinant DNA techniques in vitro, ex vivo or in vivo. The transformed cells and progeny thereof can be propagated and the introduced nucleic acid transcribed, or encoded protein expressed. It is understood that a progeny cell may not be identical to the parental cell, since there may be mutations that occur during replication. Transformed cells include but are not limited to prokaryotic and eukaryotic cells such as bacteria, fungi, plant, insect, and animal (e.g., mammalian, including human) cells. The cells may be present in culture, in a cell, tissue or organ ex vivo or present in a subject.

The term "transformed" means a genetic change in a cell following incorporation of nucleic acid (e.g., a transgene) exogenous to the cell. Thus, a "transformed cell" is a cell into which, or a progeny of which a nucleic acid molecule has been introduced by means of recombinant DNA techniques. Cell transformation may be carried out as described herein or using techniques known in the art. Accordingly, methods of producing cells containing the nucleic acids and cells expressing the chimeric polypeptides of the invention are also provided.

Typically cell transformation employs a vector. The term "vector," refers to, e.g., a plasmid, virus, such as a viral vector, or other vehicle known in the art that can be manipulated by insertion or incorporation of a nucleic acid, for genetic manipulation (i.e., "cloning vectors"), or can be used to transcribe or translate the inserted nucleic acid (i.e., "expression vectors"). Such vectors are useful for introducing nucleic acids, including a nucleic acid that encodes a chimeric polypeptide operably linked with an expression control element, and expressing the encoded protein in vitro (e.g., in solution or in solid phase), in cells or in vivo.

A vector generally contains at least an origin of replication for propagation in a cell. Control elements, including expression control elements as set forth herein, present within a vector, are included to facilitate transcription and translation. The term "expression control element" is intended to include, at a minimum, one or more components whose presence can influence expression, and can include components other than or in addition to promoters or enhancers, for example, leader sequences and fusion partner sequences, internal ribosome binding sites (GRES) elements for the creation of multigene, or polycistronic, messages, splicing signal for introns, maintenance of the correct reading frame of the gene to permit in-frame translation of mRNA, polyadenylation signal to provide proper polyadenylation of the transcript of a gene of interest, stop codons, etc.

Vectors can include a selection marker. As is known in the art, "selection marker" means a gene that allows for the selection of cells containing the gene. "Positive election" refers to a process whereby only cells that contain the selection marker will survive upon exposure to the positive selection. Drug resistance is one example of a positive selection marker; cells containing the marker will survive in culture medium containing the selection drug whereas cells which do not contain the marker will die. Such markers include drug resistance genes such as neo, which confers resistance to G418, hygr, which confers resistance to hygromycin, or puro which confers resistance to puromycin, among others. Other positive selection marker genes include genes that allow identification or screening of cells containing the marker. These genes include genes for fluorescent proteins (GFP), the lacZ gene, the alkaline phosphatase gene, and surface markers such as CD8, among others.

Vectors can contain negative selection markers. "Negative selection" refers to a process whereby cells containing a negative selection marker are killed upon exposure to an appropriate negative selection agent. For example, cells which contain the herpes simplex virus-thymidine kinase (HSV-tk) gene (Wigler et al., *Cell* 11:223 (1977)) are sensitive to the drug gancyclovir (GANC). Similarly, the gpt gene renders cells sensitive to 6-thioxanthine.

Additional selection systems may be used, including, but not limited to the hypoxanthine-guanine phosphoribosyltransferase gene (Szybalska et al., *Proc. Natl. Acad. Sci. USA* 48:2026 (1962)), and the adenine phosphoribosyltransferase (Lowy et al., *Cell* 22:817 (1980)) genes. Additional selectable genes have been described, namely trpB, which allows cells to utilize indole in place of tryptophan; hisD, which allows cells to utilize histinol in place of histidine (Hartman et al., *Proc. Natl. Acad. Sci. USA* 85:8047 (1988)); and ODC (ornithine decarboxylase), which confers resistance to the ornithine decarboxylase inhibitor, 2-(difluoromethyl)-DL-ornithine, DFMO (McConlogue (1987) In: *Current Communications in Molecular Biology*, Cold Spring Harbor Laboratory, ed.).

Vectors included are those based on viral vectors, such as retroviral, adeno-associated virus, adenovirus, reovirus, lentivirus, rotavirus genomes, simian virus 40 (SV40) or bovine papilloma virus, etc., modified for introducing and expressing a nucleic acid in a cell (Cone et al., *Proc. Natl. Acad. Sci. USA* 31:6349 (1384); *Eukaryotic Viral Vectors*, Cold Spring Harbor Laboratory, Gluzman ed., 1982; Sarver et al., *Mol. Cell. Biol.* 1:486 (1981)). Additional viral vectors useful for expression include parvovirus, rotavirus, Norwalk virus, coronaviruses, paramyxo and rhabdoviruses, togavirus (e.g., sindbis virus and semliki forest virus) and vesicular stomatitis virus.

Mammalian expression systems further include vectors specifically designed for in vivo and ex vivo expression. Such systems include adeno-associated virus (AAV) vectors (U.S. Pat. No. 5,604,090) which have been shown to provide expression of Factor IX in humans and in mice at levels sufficient for therapeutic benefit (Kay et al., *Nat. Genet.* 24:257 (2000); Nakai et al., *Blood* 91:4600 (1998)). Adenoviral vectors (U.S. Pat. Nos. 5,700,470, 5,731,172 and 5,928,944), herpes simplex virus vectors (U.S. Pat. No. 5,501,979) and retroviral lentivirus vectors are useful for infecting dividing as well as non-dividing cells and foamy viruses) vectors (U.S. Pat. Nos. 5,624,820, 5,693,508, 5,665, 577, 6,013,516 and 5,674,703 and WIPO publications WO92/05266 and WO92/14829) and papilloma virus vectors (e.g., human and bovine papilloma virus) have all been employed in gene therapy (U.S. Pat. No. 5,719,054). Vectors also include cytomegalovirus (CMV) based vectors (U.S. Pat. No. 5,561,063). Vectors that efficiently deliver genes to cells of the intestinal tract have been developed and also may be used (see, e.g., U.S. Pat. Nos. 5,821,235, 5,786,340 and 6,110,456).

In yeast, vectors that facilitate integration of foreign nucleic acid sequences into a chromosome, via homologous recombination, for example, are known in the art and can be used. Yeast artificial chromosomes (YAC) are typically used when the inserted nucleic acids are too large for more conventional vectors (e.g., greater than about 12 kb).

Introduction of nucleic acid encoding humanized antibody and humanized antibody into target cells can also be carried out by conventional methods known in the art such as osmotic shock (e.g., calcium phosphate), electroporation, microinjection, cell fusion, etc. Introduction of nucleic acid and polypeptide in vitro, ex vivo and in vivo can also be accomplished using other techniques. For example, a polymeric substance, such as polyesters, polyamine acids, hydrogel, polyvinyl pyrrolidone, ethylene-vinylacetate, methylcellulose, carboxymethylcellulose, protamine sulfate, or lactide/glycolide copolymers, polylactide/glycolide copolymers, or ethylenevinylacetate copolymers. A nucleic acid can be entrapped in microcapsules prepared by coacervation techniques or by interfacial polymerization, for example, by the use of hydroxymethylcellulose or gelatin-microcapsules, or poly (methylmethacrolate) microcapsules, respectively, or in a colloid drug delivery system. Colloidal dispersion systems include macromolecule complexes, nano-capsules, microspheres, beads, and lipid-based systems, including oil-in-water emulsions, micelles, mixed micelles, and liposomes.

The use of liposomes for introducing various compositions into cells, including nucleic acids, is known to those skilled in the art (see, e.g., U.S. Pat. Nos. 4,844,904, 5,000,959, 4,863, 740, and 4,975,282). A carrier comprising a natural polymer, or a derivative or a hydrolysate of a natural polymer, described in WO 94/20078 and U.S. Pat. No. 6,096,291, is suitable for mucosal delivery of molecules, such as polypeptides and polynucleotides. Piperazine based amphilic cationic lipids useful for gene therapy also are known (see, e.g., U.S. Pat. No. 5,861,397). Cationic lipid systems also are known (see, e.g., U.S. Pat. No. 5,459,127). Accordingly, viral and non-viral vector means of delivery into cells or tissue, in vitro, in vivo and ex vivo are included.

The invention further provides kits comprising one or more compositions of the invention, including pharmaceutical formulations, packaged into suitable packaging material. In one embodiment, a kit includes a chimeric polypeptide or hetero- or homo-oligomer thereof. In another embodiment, a kit includes a nucleic acid encoding a chimeric polypeptide. In additional embodiments, the nucleic acids further include an expression control element conferring expression in a cell; an expression vector; a viral expression vector; an adeno-associated virus expression vector; an adenoviral expression vector; and a retroviral expression vector.

In additional embodiments, a kit includes a label or packaging insert including instructions for expressing a chimeric polypeptide (e.g., humanized antibody) or a nucleic acid encoding a chimeric polypeptide in cells in vitro, in vivo, or ex vivo. In yet additional embodiments, a kit includes a label or packaging insert including instructions for treating a subject (e.g., a subject having or at risk of having asthma) with a chimeric polypeptide (e.g., humanized antibody) or a nucleic acid encoding a chimeric polypeptide in vivo, or ex vivo.

As used herein, the term "packaging material" refers to a physical structure housing the components of the kit. The packaging material can maintain the components sterilely, and can be made of material commonly used for such purposes (e.g., paper, corrugated fiber, glass, plastic, foil, ampules, etc.). The label or packaging insert can include appropriate written instructions, for example, practicing a method of the invention, e.g., treating HRV or RSV infection or the common cold. Kits of the invention therefore can additionally include instructions for using the kit components in a method of the invention.

Instructions can include instructions for practicing any of the methods of the invention described herein. Thus, invention pharmaceutical compositions can be included in a container, pack, or dispenser together with instructions for administration to a subject. Instructions may additionally include indications of a satisfactory clinical endpoint or any adverse symptoms that may occur, or additional information required by the Food and Drug Administration for use on a human subject.

The instructions may be on "printed matter," e.g., on paper or cardboard within the kit, on a label affixed to the kit or packaging material, or attached to a vial or tube containing a component of the kit. Instructions may comprise voice recording or video tape and additionally be included on a computer readable medium, such as a disk (floppy diskette or hard disk), optical CD such as CD- or DVD-ROM/RAM, magnetic tape, electrical storage media such as RAM and ROM and hybrids of these such as magnetic/optical storage media.

Invention kits can additionally include a buffering agent, a preservative, or a protein/nucleic acid stabilizing agent. The kit can also include control components for assaying for activity, e.g., a control sample or a standard. Each component of the kit can be enclosed within an individual container or in a mixture and all of the various containers can be within single or multiple packages. For example, an invention composition can be packaged into a hand pump container or pressurized (e.g., aerosol) container for spraying the composition into the throat or nasal or sinus passages of a subject.

The molecules of the invention, including multimerization polypeptides, chimeras, multimeric forms, modified forms, and nucleic acids encoding the polypeptides, can be incorporated into pharmaceutical compositions. Such pharmaceutical compositions are useful for administration to a subject in vivo or ex vivo, and for providing therapy for a physiological disorder or condition treatable with a polypeptide of the invention.

Pharmaceutical compositions include "pharmaceutically acceptable" and "physiologically acceptable" carriers, diluents or excipients. As used herein the terms "pharmaceutically acceptable" and "physiologically acceptable" include solvents (aqueous or non-aqueous), solutions, emulsions, dispersion media, coatings, isotonic and absorption promoting or delaying agents, compatible with pharmaceutical administration. Such formulations can be contained in a liquid; emulsion, suspension, syrup or elixir, or solid form; tablet (coated or uncoated), capsule (hard or soft), powder, granule, crystal, or microbead. Supplementary active compounds (e.g., preservatives, antibacterial, antiviral and antifungal agents) can also be incorporated into the compositions.

Pharmaceutical compositions can be formulated to be compatible with a particular local or systemic route of administration. Thus, pharmaceutical compositions include carriers, diluents, or excipients suitable for administration by particular routes.

Specific non-limiting examples of routes of administration for compositions of the invention are inhalation or intranasal delivery. Additional routes include parenteral, e.g., intravenous, intradermal, subcutaneous, oral, transdermal (topical), transmucosal, and rectal administration.

Solutions or suspensions used for parenteral, intradermal, or subcutaneous application can include: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide.

Pharmaceutical compositions for injection include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). The carrier can be a solvent or dispersion medium containing, for example, water, ethanol, polyol (for example, glycerol, propylene glycol, and liquid polyetheylene glycol, and the like), and suitable mixtures thereof. Fluidity can be maintained, for example, by the use of a coating such as lecithin, by the maintenance of the required particle size in the case of dispersion and by the use of surfactants. Antibacterial and antifungal agents include, for example, parabens, chlorobutanol, phenol, ascorbic acid and thimerosal. Isotonic agents, for example, sugars, polyalcohols such as manitol, sorbitol, sodium chloride can be included in the composition. Including an agent which delays absorption, for example, aluminum monostearate and gelatin can prolong absorption of injectable compositions.

Sterile injectable solutions can be prepared by incorporating the active compound in the required amount in an appropriate solvent with one or a combination of above ingredients followed by filtered sterilization. Generally, dispersions are prepared incorporating the active compound into a sterile vehicle containing a basic dispersion medium and other ingredients as above. In the case of sterile powders for the preparation of sterile injectable solutions, methods of preparation include, for example, vacuum drying and freeze-drying which yields a powder of the active ingredient plus any additional desired ingredient from a previously sterile-filtered solution thereof.

For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays, inhalation devices (e.g., aspirators) or suppositories. For transdermal administration, the active compounds are formulated into ointments, salves, gels, or creams as generally known in the art.

Invention polypeptides and nucleic acids encoding them can be prepared with carriers that protect against rapid elimination from the body, such as a controlled release formulation or a time delay material such as glyceryl monostearate or glyceryl stearate. The compositions can also be locally or systemically delivered using implants and microencapsulated delivery systems to achieve sustained delivery or for controlled release.

Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to cells or tissues using antibodies or viral coat proteins) can also be used as pharmaceutically acceptable carriers. These can be prepared according to methods known to those skilled in the art, for example, as described in U.S. Pat. No. 4,522,811.

Additional pharmaceutical formulations appropriate for the compositions for administration in the methods of the invention are known in the art (see, e.g., *Remington's Pharmaceutical Sciences* (1990) 18th ed., Mack Publishing Co., Easton, Pa.; *The Merck Index* (1996) 12th ed., Merck Publishing Group, Whitehouse, N.J.; and *Pharmaceutical Principles of Solid Dosage Forms*, Technonic Publishing Co., Inc., Lancaster, Pa., (1993)).

The pharmaceutical formulations can be packaged in dosage unit form for ease of administration and uniformity of dosage. "Dosage unit form" as used herein refers to physically discrete units suited as unitary dosages for the subject to be treated; each unit containing a predetermined quantity of active compound calculated to produce the desired therapeutic effect in association with the pharmaceutical carrier or excipient.

Figure 6:
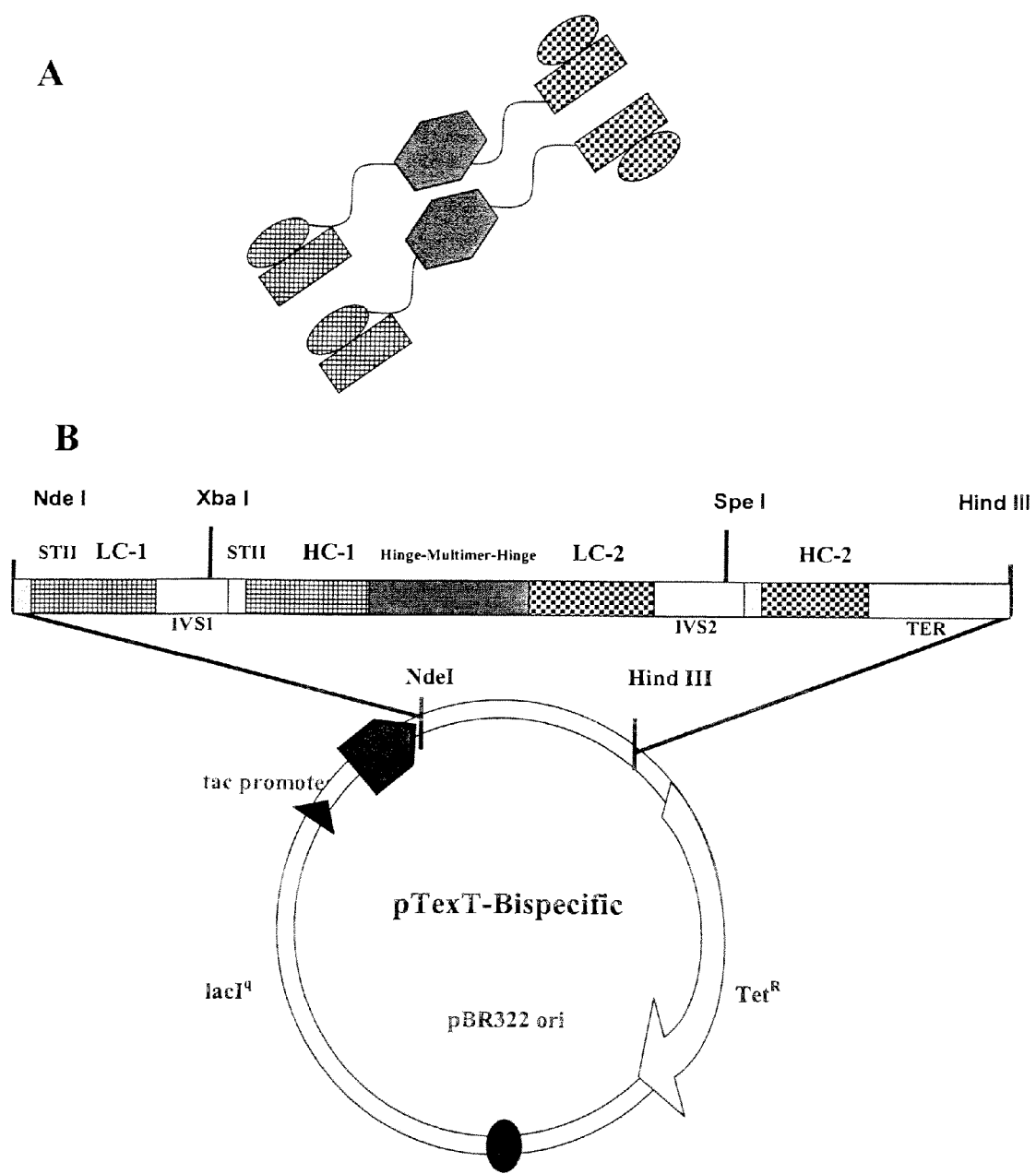
FIGS. 6A-6B show a bispecific multimeric protein. A) Fab moities illustrated with different hatching have different specificities or functions. A linker sequence is illustrated as a hexagon. B) This polypeptide is produced from one tricistronic RNA molecule. The coding sequence for the first polypeptide chain translated from this message is illustrated by the hatched box, representing the anti-CD-3 light chain (LC-1). The second DNA fragment encodes the central chimeric polypeptide consisting of the anti-CD-3 heavy chain (HC-1) linked to a hinge derived from IgD, followed by a dimerization domain, a second hinge, and the anti-CD19 light chain (LC-2). The third RNA (empty box) would encode the anti-CD19 heavy chain (HC-2). The restriction sites are as indicated.
Figure 7:
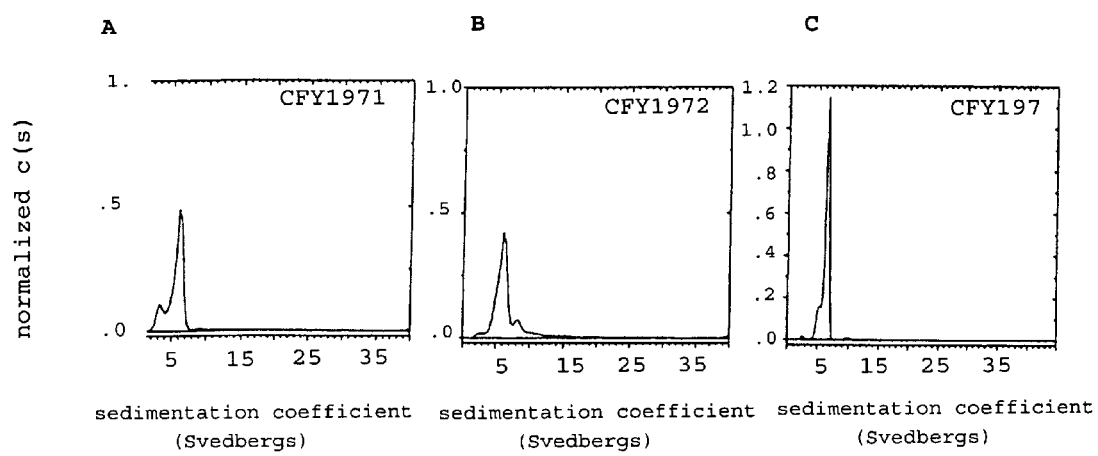
FIG. 7A-C show improvement in tetramerization of ATFαIL by substituting amino acids at solvent exposed positions: A) CFY1971; B) CFY1972: and C) CFY197.

Multimeric antibodies of the invention include antibodies that protect against virus infection of cells. For example, antibodies that bind ICAM-1 that have been fused with a multimerization polypeptide form multimers that can protect cells from HRV infection (FIGS. 6 and 7). In particular, CFY196 (Fab-ATFα(1)LI+S), CFY197 (Fab-ATFα(3)IL) and CFY193B (Fab-ATFα(2)LL) demonstrated the greatest protective efficacy against HRV infection.

As respiratory syncytial virus (RSV) also utilizes ICAM-1 as a co-receptor for cell infection, antibody or ligand that binds ICAM-1 and that have been fused with a multimerization polypeptide to form multimers can also protect cells from RSV infection. Thus, in another embodiment, the invention provides antibody and ligand multimers that protect against RSV infection of cells.

As used herein, the term "protective efficacy" is the amount of an antibody which can protect 50% of susceptible cells from infection (i.e. $EC_{50}$) under experimental conditions (see, e.g., Example 6). For example, for RSV, protective efficacy in $EC_{50}$ is the amount of antibody that protects 50% of cells from RSV infection. Thus, an antibody having a protective efficacy 5 times greater than another antibody (e.g., non-humanized) can be used in an amount 5 fold less than the other antibody while still providing the same degree of protection from infection.

Multimeric antibodies typically exhibit greater protective efficacy than a monomeric counterpart. In one embodiment, an antibody multimer has a protective efficacy at least 2 to 5 times greater than the antibody monomer. In another embodiment, an antibody multimer has a protective efficacy at least 5 to 10 times greater than antibody monomer. In yet another embodiment, an antibody multimer has a protective efficacy at least 10 to 20 times greater than the antibody monomer. In still another embodiment, an antibody has a protective efficacy at least 20 to 30 times greater or more than the antibody monomer, for example, 30 to 50 times, 50 to 100 times, or 100 to 1000 times or more.

Chimeric polypeptides of the invention include multimerization polypeptide fused to antibody that binds to ICAM-1. Although not wishing to be bound by theory, it is believed that antibody binding to ICAM-1 inhibits viral binding or the ability to infect or penetrate the cell thereby inhibiting viral infection or proliferation. Such antibodies are therefore useful for inhibiting pathogens such as respiratory syncytial and other viruses (e.g., HRV and coxackie A virus), bacteria, fungi and protozoa (e.g., malaria) that bind to ICAM-1. Thus, the multimerized antibodies are useful for inhibiting HRV and RSV infection as well as for inhibiting any microorganism or other pathogen in which ICAM-1 receptor participates. Accordingly, the invention provides multimerized antibodies (including fully or partially humanized forms) that inhibit pathogen infection of cells where infection is mediated, at least in part, by binding to ICAM-1, and methods for inhibiting pathogen infection of cells where infection is mediated, at least in part, by binding to ICAM-1.

In one embodiment, a method includes contacting a virus or cell with an amount of multimerized antibody that binds to ICAM-1 sufficient to inhibit viral infection of the cell. In one aspect, the multimerized antibody is humanized. In another embodiment, a method includes administering to a subject an amount of multimerized antibody that binds to ICAM-1 sufficient to inhibit viral infection of the subject. In various aspects, the virus is RSV, coxackie A virus and HRV. In yet another embodiment, a method includes administering to a subject an amount of multimerized antibody that binds to ICAM-1 sufficient to inhibit infection of the subject by a pathogen. In still another embodiment, a method includes administering to a subject an amount of multimerized antibody that binds to ICAM-1 sufficient to ameliorate a symptom of the infection, e.g., a symptom of the common cold.

As used herein, the term "ameliorate," when used in reference to a condition such as a symptom of a disease means to reduce one or more symptoms of the condition. For example, symptoms associated with the common cold include fever, headache, chills, sneezing, coughing, congestion, sore throat, runny nose, sore muscles, general malaise, etc. Thus, to ameliorate the common cold or a pathogen associated with the common cold (e.g., HRV) means to reduce one or more of fever, headache, chills, sneezing, coughing, congestion, sore throat, runny nose, sore muscles, general malaise, etc.

In addition to inhibiting a symptom, replication or progression of pathogens that function directly or indirectly through ICAM-1, invention multimerized antibodies can be used to treat undesirable conditions, such as diseases or disorders in which ICAM-1 plays a role. For example, LFA-1 interaction with ICAM-1 participates in inflammation. An invention antibody may be used to inhibit this interaction thereby modulating (e.g., decrease) local or systemic inflammation. Thus, in another embodiment, a method includes administering to a subject enough multimerized antibody to reduce or prevent inflammation.

Furthermore, ICAM-1 plays a role in other immune response pathways, cancer and metastasis. Thus, an invention antibody may be used to modulate immune response in order to reduce or prevent organ transplant rejection or autoimmune diseases or cancer or metastasis. Accordingly, the invention provides multimerized antibodies that modulate immune responsiveness (e.g., inflammation) and other cellular processes in which ICAM-1 participates, as well as methods for modulating immune response pathways and other cellular processes in which ICAM-1 participates.

The invention also provides methods for inhibiting infection (e.g., prophylaxis), inhibiting progression or treating a pathogenic infection of a subject. For example, blocking RSV from the upper respiratory tract will prevent the entry of RSV, and therefore prevent RSV from invading the lower respiratory tract. ICAM-1 binding molecules may be delivered intranasally or intra-orally as sprays or drops to a subject.

Thus, in one embodiment, a method includes administering to a subject having or at risk of having an RSV infection an amount of multimerized antibody sufficient to inhibit infection, inhibit progression or to treat RSV infection of the subject. In another embodiment, a method includes administering to a subject having or at risk of having an coxackie A virus or HRV infection an amount of multimerized antibody sufficient to inhibit infection, inhibit progression or to treat coxackie A virus or HRV infection of the subject. In still another embodiment, a method includes administering to a subject having or at risk of having malaria an amount of multimerized antibody sufficient to inhibit infection, inhibit progression or to treat malaria of the subject.

The invention further provides methods of decreasing or inhibiting (i.e., ameliorating) one or more symptoms of a pathogen infection (e.g., caused by RSV, coxackie A virus, HRV or malaria). In one embodiment, a method includes administering to a subject having one or more symptoms associated with RSV, coxackie A virus, HRV or malaria an amount of a multimerized antibody sufficient to decrease or inhibit one or more symptoms associated with, RSV, coxackie A virus, HRV or malaria in the subject. Symptoms decreased or inhibited include, for example, for RSV, one or more of pneumonia, fever, bronchitis, and upper respiratory tract infection; for coxackie A virus, one or more of fever, headache, chills, sneezing, coughing, congestion, sore throat, etc; for malaria, one or more of fever, chill, enlarged liver, anemia.

In another embodiment, a method includes administering to a subject having pneumonia, fever, bronchitis, or upper respiratory tract infection an amount of a multimerized antibody sufficient to decrease or inhibit one or more symptoms of pneumonia, fever, bronchitis, or upper respiratory tract infection in the subject. In one aspect, the humanized antibody is administered locally. In another aspect, the multimerized antibody is administered via inhalation or intranasaly. In yet another aspect, the subject has or is at risk of having asthma.

The methods of the invention may be practiced prior to infection (i.e. prophylaxis) or after infection, before or after acute or chronic symptoms of the infection or physiological condition or disorder develops (e.g., before organ transplantation). Administering a composition prior to or immediately following development of symptoms may lessen the severity of the symptoms in the subject. Administering a composition prior to development of symptoms in the subject may decrease contagiousness of the subject thereby decreasing the likelihood of other subjects becoming infected from the infected subject.

The term "subject" refers to animals, typically mammalian animals, such as a non-human primate (apes, gibbons, chimpanzees, orangutans, macaques), a domestic animal (dogs and cats), a farm animal (horses, cows, goats, sheep, pigs), experimental animal (mouse, rat, rabbit, guinea pig) and humans. Human subjects include adults, and children, for example, newborns and older children, for example, between the ages of 1 and 5, 5 and 10 and 10 and 18. Human subjects may include those having or at risk of having a viral infection, such as HRV or RSV, and which develops one or more symptoms of the infection. Human subjects include those having or at risk of having asthma, including asthmatics suffering from chronic asthma prior to or following suffering an acute asthma attack. Subjects include disease model animals (e.g., such as mice and non-human primates) for testing in vivo efficacy of humanized antibodies of the invention (e.g., an HRV or RSV animal model, an asthma animal model, an organ transplant model, an autoimmune disorder model, cancer model, etc.).

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described herein.

All publications, patents and other references cited herein are incorporated by reference in their entirety. In case of conflict, the present specification, including definitions, will control.

As used herein, the singular forms "a", "and," and "the" include plural referents unless the context clearly indicates otherwise. Thus, for example, reference to "a polypeptide" includes a plurality of polypeptides (e.g., multimerization, chimeric, heterologous polypeptides) and reference to "a cell" can include reference to one or more such cells, and so forth.

A number of embodiments of the invention have been described. Nevertheless, it will be understood that various modifications may be made without departing from the spirit and scope of the invention. Accordingly, the following examples are intended to illustrate but not limit the scope of invention described in the claims.

EXAMPLES

Example 1

This example describes the design of multimerization domains, linker sequences and chimeric polypeptides.

ATFα amino acids 181-211 constitute four and one-half heptad-repeats (31 amino acids). Since all the residues at the d position (position four) of each repeat are leucines, this heptad-repeat sequence is also referred to as a leucine zipper domain. ATFα amino acids 181-211 has 45% identity to the GCN4 leucine zipper domain.

Variants of ATFα amino acids 181-211 were produced by replacing position a and d (positions one and four in each of the heptad repeats) with each of the three hydrophobic, apolar residues: leucine, isoleucine and valine. (Table 3A). ATFα variants that have leucine and isoleucine at either a or d position form trimers or tetramers; tetramer forming sequences include ATFα-LI and ATFα-IL, trimer forming sequences include ATFα-LL and ATFα-II. ATFα-VL forms a mixture of dimer and tetramer; all variants with valine at as or d gave a high proportion of dimer.

The ATFα-LI domain forms tetramer when fused with either an antibody Fab fragment or with a reporter protein, thioredoxin.

Exemplary linker sequences were based on the human immunoglobulin D hinge sequence, which is the longest known flexible hinge among human immunoglobulins. The human IgD hinge has a total of 63 amino acid residues, and the 57$^{th}$ residue is a cysteine (Padlan, *Mol. Immunol.* 31:169 (1994)).

Five versions of the IgD hinge are listed in Table 5: D30, D35, ED, EDC and D63. D30 contains the first 30 residues of the IgD hinge, D35 contains the first 35 residues, ED contains all of the 56 amino acid residues before the cysteine, EDC contains all of the 56 amino acid residues in ED plus the cysteine, and D63 contains the complete hinge of 63 amino acids.

When purified tetramers prepared using ATFα-LI were compared, proteins with D35 were less stable than tetramers formed by D30 and ED, which remained in the tetrameric state over time. The C terminus of D35 ends in two glycines (GROG). When it is fused with the N terminus of the multimerization domain, the two glycines may destabilize the α helixes of the multimerization domain explaining why D35 tetramers were less stable.

Example 2

This example describes the cloning of an anti-ICAM humanized Fab fragment with antigen binding sites derived from Mab 1A6.

An expression vector was assembled to produce Fab 19 and multimeric Fab 19 from a dicistronic operon (FIG. 1). Dicistron operons are described in Carter et al., *Biotechnology* 10:163 (1992).

In brief, the $V_H$ and $V_L$ domains are precisely fused on their 5' ends to a gene segment encoding the enterotoxin II (stII) signal sequence. The intervening sequence (IVS) in the dicistronic gene contains a ribosome entry site, while the 3' end of the gene contains the bacteriophage λ $t_0$ transcriptional terminator (TER). A unique SacI site was inserted just before the stop codon in the $C_H1$ domain and a unique EcoRI site just after the stop codon to facilitate the addition of sequences encoding hinge and polymerization domains. The isopropyl-1-thioβ-D-galactopyranoside (IPTG)-inducible ptac promoter was used to drive expression of this dicistronic message.

The gene segment for the light chain fragment (from SpeI to XbaI) was synthesized using PCR. The PCR product was a fusion of two templates, the $V_L$ fragment encoding the variable domain of an humanized anti-ICAM antibody, and the $C_L$ template, whose sequence was derived from human $κ_1$ light chain constant region (Palm and Hilschmann, *Z. Physiol. Chem.* 356:167 (1975)).

The $V_L$ template was synthesized using a series of overlapping oligonucleotides (Table 1). Oligonucleotides were first annealed in two groups consisting of: oligonucleotides 1, 2 and 3; and oligonucleotides 4, 5 and 6. Each annealed group was extended with Klenow fragment of DNA polymerase. Annealed and extended products were pooled as overlapping templates that were fused via PCR with P1 and P2 oligonucleotides (Table 2). The PCR product was directly cloned into the pCR2.1 vector (Invitrogen) and sequenced. The $C_L$ template was derived from oligonucleotides that had been annealed in four groups (Table 1: Fab 4, 5 and 6; Fab 7 and 8; Fab 9 and 10; Fab 11 and 28) and extended with the Klenow fragment of DNA polymerase (Stratagene, Lot#0800176). The pool of DNA was then amplified using a high-fidelity polymerase mixture (Roche Expand High Fidelity, Lot #85610228), and the flanking DNA primers, Fab 29 and Fab 3S. The PCR product was cloned into the PCR 2.1 TOPO cloning vector. The $V_L$ and $C_L$ domains were fused using oligonucleotides Fab1 and Fab 11 and a 5' SpeI site was added with oligonucleotides Fab26 and P3. The final light chain clones were sequenced in their entirety.

A similar approach was used to clone the gene segment containing the heavy chain and the terminator as an Xba I/Hind III fragment. A $C_H$ template based on the sequence of the $C_H1$ domain of human IgG1 (Ellison, et al. *Nucl. Acids Res.* 10:4071 (1982)) was made by annealing and extending four groups of oligonucleotides (Table 1, Fab 16 and 17, Fab 18 and 19, Fab 25 and 21 and Fab 20, 22 and 23) with the $C_L$. The $V_H$ domain encoding the heavy chain variable region of a humanized anti ICAM antibody, was made by first annealing oligonucleotide 7, 8 and 9; oligonucleotide 10, 11 and 12; and oligonucleotide 13 and p4. Each annealed group was extended with the Klenow fragment of DNA polymerase. The annealed and extended products were pooled as overlapping templates that were fused N-terminally to the Fab 1 oligonucleotide with oligonucleotides Fab13, 12A and 12S, and C terminally to the $C_{H1}$ domain using PCR with oligonucleotides Fab 12s and Fab 24 as primers. This fragment was also completely sequenced. The expression plasmid for the humanized, anti ICAM Fab protein, termed Fab 19, was made by ligating the SpeI/Xba light chain fragment and the XbaI/Hind III heavy chain fragment into SpeI/HindIII-digested ptac/Tet to generate pFab19/Tet (FIG. 1).

TABLE 1

Oligonucleotide Sequences

| Oligo | Sequence |
| --- | --- |
| Oligo 1 | ACAAACGCGTACGCTGATATCCAGATGACCCAATCTCCGTC AGCCTGAGCGCCAGTGTTGGTGATCGAGTTACCATTACT (SEQ ID NO: 83) |
| Oligo 2 | GGTTTTTGTTGATACCAGTGAAGATTATTACTGATAGATTGGCTGGCG CGGCAAGTAATGGTAACTCGATCACCAACACTGGCGC (SEQ ID NO: 84) |
| Oligo 3 | CTTCACTGGTATCAACAAAAACCGGGTAAAGCTCCGAAACTTCTTAT CTATCACGCCTCTCAGAGCATTAGCGGCGTTCCG (SEQ ID NO: 85) |
| Oligo 4 | GAGAGCTGATGGTAAGGGTAAAGTCCGTGCCCGAGCCAGAGCCAGA GAAGCGGCTCGGAACGCCGCTAATGCTCTGAGAG (SEQ ID NO: 86) |
| Oligo 5 | CTTTACCCTTACCATCAGCTCTCTTCAGCCGGAAGACTTTGCCACCTATT ATTGTCAGCAGTCTA (SEQ ID NO: 87) |
| Oligo 6 | GGTGCAGCCACAGTGCGCTTAATCTCGACCTTGGTACCTTGACCGA AGGTATACGGCCAGCTATTAGACTGCTGACAATAATAGG (SEQ ID NO: 88) |
| Oligo 7 | ACAAACGCGTACGCTGAAGTTCAACTTGTTGAGTCTGGTGGCGGTCTGG TTCAGCCCGGGGGCTCTCTGCGCCTGTCTTGCGCAGCAAG (SEQ ID NO: 89) |
| Oligo 8 | CTTACCCGGAGCTTGCCTCACCCAATGGATGTAGGTGTCCTTAATGTTG AAACCGCTTGCTGCGCAAGACAGGCG (SEQ ID NO: 90) |
| Oligo 9 | GGCAAGCTCCGGGTAAGGGTCTGGAGTGGGTGGCACGTATCGACCCGGCA AACGACAACACCATTTACGCTGACAGCGTGAAGGGCCG (SEQ ID NO: 91) |
| Oligo 10 | GGTACGCGGTGTTCTTAGAGTCGTCGCTAGAAATAGTAAAACGGCCCTTCA CGCTGTCAGCGTAAATGGTGTTGTCGTTTGCCGGGT (SEQ ID NO: 92) |
| Oligo 11 | GACTCTAAGAACACCGCGTACCTTCAGATGAACTCTCTGCGTGCCGAGGACA CCGCCGTCTACTACTGCACGGCCTCTGGCTACTGGTTTGCCTACTGGGGC (SEQ ID NO: 93) |
| Oligo 12 | GGTGGAGGCGCTCGAGACGGTGACAAGCGTGCCCTGGCCCCA GTAGGCAAACCAGTAGCCAGAGG (SEQ ID NO: 94) |
| Oligo 13 | CCCGGCAAACGACAACACCATTTACGCTG (SEQ ID NO: 95) |
| P1 | ACAAACGCGTACGCTGATATCC (SEQ ID NO: 96) |

TABLE 1-continued

Oligonucleotide Sequences

| Oligo | Sequence |
|---|---|
| P2 | GATGGTGCAGCCACAGTGCGC (SEQ ID NO: 97) |
| P3 | GCGATATTCTTTTTCATATACTGTTTCCTG (SEQ ID NO: 98) |
| P4 | GGTGGAGGCGCTCGAGACGG (SEQ ID NO: 99) |
| Fab 1 | ATG AAA AAG AAT ATC GCA TTT CTT CTT GCA TCT ATG TTC GTT TTT TCT ATT GCT ACA AAC GCG TAC GCT (SEQ ID NO: 100) |
| Fab 4 | ACT GTG GCT GCA CCA TCT GTC TTC ATC TTC CCG CCA TCT GAT GAG CAG TTG AAA TCT GGA ACT GCC (SEQ ID NO: 101) |
| Fab 5 | GGC CTC TCT GGG ATA GAA GTT ATT CAG CAG GCA CAC AAC AGA GGC AGT TCC AGA TTT CAA (SEQ ID NO: 102) |
| Fab 6 | CTT CTA TCC CAG AGA GGC CAA AGT ACA GTG GAA GGT GGA TAA CGC CCT CCA ATC GGG (SEQ ID NO: 103) |
| Fab 7 | GGC TGT AGG TGC TGT CCT TGC TGT CCT GCT CTG TGA CAC TCT CCT GAG AGT TAC CCG ATT GGA GGG CG (SEQ ID NO: 104) |
| Fab 8 | GCA AGG ACA GCA CCT ACA GCC TCA GCA GCA CCC TGA CGC TGA CGC TGA GCA AGG CAG ACT ACG AGA AAC ACA AAG TCT ACG CCT (SEQ ID NO: 105) |
| Fab 9 | AAG CTC TTT GTG ACG GGC TCG ACA GGC CCT GAT GGT GAC TCG CAG GCG TAG ACT TTG TGT TTC (SEQ ID NO: 106) |
| Fab 10 | AGC CCC GTC ACA AAG AGC TTC AAC AGG GGA GAG TGT TAA GCT GAT CCT CTA CGC CGG ACG CAT CGT (SEQ ID NO: 107) |
| Fab 11 | CTC TAG ATA CCC TTT TTA CGT GAA CTT GCG TAC TAG GGC CAC GAT GCG TCC GGC GTA GAG G (SEQ ID NO: 108) |
| Fab 12a | GAA ATG CGA TAT TCT TTT TCA TAA AAT CAC CTC AAC CTC TAG ATA CCC (SEQ ID NO: 109) |
| Fab 12s | AAA AAG GGT ATC TAG AGG TTG AGG (SEQ ID NO: 110) |
| Fab 13 | GAC TCA ACA AGT TGA ACT TCA GCG TAC GCG TTT GTA GCA A (SEQ ID NO: 111) |
| Fab 14 | GAA GTT CAA CTT GTT GAG TCT (SEQ ID NO: 112) |
| Fab 16 | CAC GCT TGT CAC CGT CTC GAG CGC CTC CAC CAA GGG CCC AT (SEQ ID NO: 113) |
| Fab 17 | GTG CCC CCA GAG GTG CTC TTG GAT GAG GGT GCC AGG GGG AAG ACC GAT GGG CCC TTG GTG GAG CG (SEQ ID NO: 114) |
| Fab 18 | CAC CTC TGG GGG CAC AGC GGC CCT GGG CTG CCT GGT CAA GGA CTA CTT CCC CGA ACC GGT GAC G (SEQ ID NO: 115) |
| Fab 19 | GGA CAG CCG GGA AGG TGT GCA CGC CGC TGG TCA GGG CGC CTG AGT TCC ACG ACA CCG TCA CCG GTT CGG GG (SEQ ID NO: 116) |
| Fab 20 | GAC CTA CAT CTG CAA CGT GAA TCA CAA GCC CAG CAA CAC CAA GGT GGA CAA GAA AGT TGA GCC CAA ATC TTG TGACAA AAC TCA CAC AGA GCT CTG AGA ATT CCG CGG CAT CGC (SEQ ID NO: 117) |
| Fab 21 | GAT TCA CGT TGC AGA TGT AGG TCT GGG TGC CCA AGC TGC TGG AGG GCA CGG TCA CCA CGC TGC (SEQ ID NO: 118) |
| Fab 22 | GGC CCT AGA GTC CTA ACG CTC GGT TGC CGC CGG CGT TTT TAT TGT TAA CTC ATG TTT GAC AGC TTA TCA TCG ATA AGC TT (SEQ ID NO: 119) |
| Fab 23 | GCG TTA GGG ACT CTA GGG CCG TCG CAT GCC GCG GAA TTC TCA GAG CTC TGT GTG AGT TTT GTC ACA AGA TTT GGG CTC AAC TTT CTT GTC AC (SEQ ID NO: 120) |
| Fab 24 | AAG CTT ATC GAT GAT AAG C (SEQ ID NO: 121) |
| Fab 25 | GCG GCG TGC ACA CCT TCC CGG CTG TCC TAC AGT CCT CAG GAC TCT ACT CCC TCA GCA GCG TGG TGA CCG TG (SEQ ID NO: 122) |
| Fab 26 | AAC AAT ACT AGT CAG GAA ACA GTA TA (SEQ ID NO: 123) |

TABLE 1-continued

Oligonucleotide Sequences

| Oligo | Sequence |
|---|---|
| Fab 27 | ACT AGT ATT GTT ATC CGC TC (SEQ ID NO: 124) |
| Fab 29 | CAT AGA TGC AAG AAG AAA TGC (SEQ ID NO: 125) |

Example 3

This example describes cloning of human ATFα leucine zipper domain variants. This example also describes cloning of the human ATFα leucine zipper domain variants with attached linker (hinge) sequences.

The ATFα leucine zipper domain variants (Table 3A) were made by PCR amplification using two DNA oligonucleotides "A" and "B" that are complementary at the 3' ends as the template (Table 2). The oligonucleotide pairs were annealed, extended with the Klenow fragment of DNA polymerase, and amplified by PCR using oligonucleotides P1 and P2 as primers. The resulting PCR products were purified and cloned into the PCR cloning vector, TOPO pCR2.1 (Invitrogen). Plasmid DNA with the cloned insert was isolated and sequenced.

To fuse each cloned ATFα domain variant to a particular hinge sequence, a junctional oligonucleotide, whose 5' end is complementary to the 3' end of the appropriate hinge, was used in a PCR reaction against the ATFα domain variant template. This PCR product was then used in combination with the hinge template in another PCR reaction to generate the hinge-ATFα domain fragment. By design, the hinge-ATFα domain fragment has a SacI site on the N terminus and a EcoRI site on the C terminus. After sequencing, the hinge-ATFα domain fragment was cloned into the expression vector that carries the Fab fragment and was pre-digested with SacI and EcoRI, to be fused in-frame with the C terminus of the $C_H1$ domain of Fab (FIG. 1).

TABLE 2

Oligonucleotides for ATF Leucine Zipper Variants

ATF domain oligonucleotides

ATFα(1)-LI (SEQ ID NOs: 126-129):

| | |
|---|---|
| A: | CTTAGCTCTATTGAGAAGAAACTTGAGGAGATTAC CTCTCAACTGATTCAGATC |
| B: | TTGGGCCAGCTCATTGCGGATAAGGGTCAGTTCATTGC TGATCTGAATCAGTTGAG |
| P1: | CTTAGCTCTATTGAGAAG |
| P2: | CGAATTCATTGGGCCAGCTCATTGC |

ATFα(2)-LI (SEQ ID NOs: 130-133):

| | |
|---|---|
| A: | CTTAGCTCTATTGAGAAGAAACTTGAGGAGATTAC CTCTCAACTGATTCAGATC |

TABLE 2-continued

Oligonucleotides for ATF Leucine Zipper Variants

ATF domain oligonucleotides

| | |
|---|---|
| B: | TTGGGCCAGCTCATTGCGGATAAGGGTCAGTTCATTGC GGATCTGAATCAGTTGAG |
| P1: | CTTAGCTCTATTGAGAAG |
| P2: | CGAATTCATTGGGCCAGCTCATTGC |

ATFα(3)-LI (SEQ ID NOs: 134-137):

| | |
|---|---|
| A: | CTTAGCTCTATTGAGAAGAAACTTGAGGAGATTAC CTCTCAACTGCAACAGATC |
| B: | TTGGGCCAGCTCATTGCGGATAAGGGTCAGTTCATTGC TGATCTGTTGCAGTTGAG |
| P1: | CTTAGCTCTATTGAGAAG |
| P2: | CGAATTCATTGGGCCAGCTCATTGC |

ATFα-LL (SEQ ID NOs: 138-141):

| | |
|---|---|
| A: | CTTAGCTCTCTTGAGAAGAAACTTGAGGAGCTTAC CTCTCAACTGATTCAGCTTCGG |
| B: | ATTGGGCCAGCTCATTACGCAGAAGGGTCAG TTCATTCCGAAGCTGAATCAGTTG |
| P1: | CTTAGCTCTCTTGAGAAGAAAC |
| P2: | CGAATTCATTGGGCCAGCTCATTA |

ATFα-IL (SEQ ID NOs: 142-145):

| | |
|---|---|
| A: | ATTAGCTCTTTAGAGAAGAAAATTGAGGAGCTG ACCTCTCAAATCCAGCAGCTGCGT |
| B: | TTGGGCAATCTCATTACGAAGAAGGGTGATTTCATT ACGCAGCTGCTGGATTTGAGA |
| P1: | ATTAGCTCTTTAGAGAAGAAA |
| P2: | CGAATTCATTGGGCAATCTCATTACG |

ATFα-II (SEQ ID NOs: 146-149):

| | |
|---|---|
| A: | ATCAGCTCTATTGAGAAGAAAATCGAGGAGATTACCTC TCAAATCATTC |
| B: | CATTGGGCAATCTCATTACGGATAAGCGTGATTTCATT CCGAATCTGAATGATTTGAGAGGTAATC |
| P1: | ATCAGCTCTATTGAGAAG |
| P2: | CGAATTCATTGGGCAATCTCATTACG |

ATFα-VL (SEQ ID NOs: 150-153):

| | |
|---|---|
| A: | GTTAGCTCTCTTGAGAAGAAAGTTGAGGAGCTT ACCTCTCAAGTGATTCAGCTTCGG |
| B: | TTGGGCAACCTCATTACGCAGAAGGGTCACTTCATT CCGAAGCTGAATCACTTGAGAG |
| P1: | GTTAGCTCTCTTGAGAAGAAAG |
| P2: | CGAATTCATTGGGCAACCTCATTACG |

TABLE 3A

ATFα Leucine Zipper Domain Variants

| | 1 | 2 | 3 | 4 | 5 | |
|---|---|---|---|---|---|---|
| Repeats: | a b c d e f g | a b c d e f g | a b c d e f g | a b c d e f g | a b c | |
| ATFα(1)-LI: | L S S I E K K | L E E I T S Q | L I Q I S N E | L T L I R N E | L A Q | (SEQ ID NO: 1) |
| ATFα(2)-LI: | L S S I E K K | L E E I T S Q | L I Q I R N E | L T L I R N E | L A Q | (SEQ ID NO: 2) |

TABLE 3A-continued

ATFα Leucine Zipper Domain Variants

| Repeats: | 1 a b c d e f g | 2 a b c d e f g | 3 a b c d e f g | 4 a b c d e f g | 5 a b c | |
|---|---|---|---|---|---|---|
| ATFα(3)-LI: | L S S I E K K | L E E I T S Q | L Q Q I R N E | L T L I R N E | L A Q | (SEQ ID NO: 3) |
| ATEα-LL: | L S S L E K K | L E E L T S Q | L I Q L R N E | L T L L R N E | L A Q | (SEQ ID NO: 4) |
| ATFα-IL: | I S S L E K K | I E E L T S Q | I Q Q L R N E | I T L L R N E | I A Q | (SEQ ID NO: 5) |
| ATFα-I I: | I S S I E K K | I E E I T S Q | I I Q I R N E | I T L I R N E | I A Q | (SEQ ID NO: 6) |
| ATFα-VL: | V S S L E K K | V E E L T S Q | V I Q L R N E | V T L L R N E | V A Q | (SEQ ID NO: 7) |
| ATFα-WT: | V S S L E K K | A E E L T S Q | N I Q L S N E | V T L L R N E | V A Q | (SEQ ID NO: 8) |

TABLE 3B

Leucine Zipper Domains Homologous to ATFα

| Repeats: | 1 a b c d e f g | 2 a b c d e f g | 3 a b c d e f g | 4 a b c d e f g | 5 a b c | |
|---|---|---|---|---|---|---|
| ATFα-WT: | V S S L E K K | A E E L T S Q | N I Q L S N E | V T L L R N E | V A Q | (SEQ ID NO: 8) |
| CREB-Pa: | V M S L E K K | A E E L T Q T | N M Q L Q N E | V S M L K N E | V A Q | (SEQ ID NO: 38) |
| JUN-D: | I S R L E E K | V K T L K S Q | N T E L A S T | A S L L R E Q | V A Q | (SEQ ID NO: 39) |
| C-JUN: | I A R L E E K | V K T L K A Q | N S E L A S T | A N M L R E Q | V A Q | (SEQ ID NO: 40) |
| ATF-1: | V K C L E N R | V A V L E N Q | N K T L I E E | L K T L K D L | Y S N | (SEQ ID NO: 41) |
| ATF-2: | V Q S L E K K | A E D L S S L | N G Q L Q S E | V T L L R N E | V A Q | (SEQ ID NO: 42) |

TABLE 3C

Sequence Comaprison of Wild Type Leucine Zipper Domains (in % identity)

| | GCN4 | ATFα |
|---|---|---|
| GCN4 | 100% | 45% |
| ATFα | 45% | 100% |
| CREB-Pa | 45% | 74% |
| ATF1 | 35% | 29% |
| ATF2 | 39% | 77% |
| C-JUN | 29% | 39% |
| JUN-D | 32% | 48% |

TABLE 3D

Amino Acid Sequences of Coiled-Coil Domain Based Multimerization Domains

| | |
|---|---|
| ATF1-LI: | LKSIENRLAVIENQLKTIIEELKTIKDLLSN (SEQ ID NO: 9) |
| ATF1-LL: | LKSLENRLAVLENQLKTLIEELKTLKDLLSN (SEQ ID NO: 10) |
| ATF1-IL: | IKSLENRIAVLENQIKTLIEEIKTLKDLISN (SEQ ID NO: 11) |
| ATF1-II: | IKSIENRIAVIENQIKTIIEEIKTIKDLISN (SEQ ID NO: 12) |
| ATF1-VL: | VKSLENRVAVLENQVKTLIEEVKTLKDLVSN (SEQ ID NO: 13) |
| ATF1-LV: | LKSVENRLAVVENQLKTVIEELKTVKDLLSN (SEQ ID NO: 14) |
| CJUN-LI: | LARIEEKLKTIKAQLSEIASTLNMIREQLAQ (SEQ ID NO: 15) |
| CJUN-LL: | LARLEEKLKTLKAQLSELASTLNMLREQLAQ (SEQ ID NO: 16) |
| CJUN-IL: | IARLEEKIKTLKAQISELASTINMLREQIAQ (SEQ ID NO: 17) |
| CJUN-II: | IARIEEKIKTIKAQISEIASTINMIREQIAQ (SEQ ID NO: 18) |
| CJUN-VL: | VARLEEKVKTLKAQVSELASTVNMLREQVAQ (SEQ ID NO: 19) |
| CJUN-LV: | LARVEEKLKTVKAQLSEVASTLNMVREQLAQ (SEQ ID NO: 20) |
| JUND-LI: | LSRIEEKLKTIKSQLTEIASTLSLIREQLAQ (SEQ ID NO: 21) |
| JUND-LL: | LSRLEEKLKTLKSQLTELASTLSLLREQLAQ (SEQ ID NO: 22) |
| JUND-IL: | ISRLEEKIKTLKSQITELASTISLLREQIAQ (SEQ ID NO: 23) |
| JUND-II: | ISRIEEKIKTIKSQITEIASTISLIREQIAQ (SEQ ID NO: 24) |
| JUND-VL: | VSRLEEKVKTLKSQVTELASTVSLLREQVAQ (SEQ ID NO: 25) |
| JUND-LV: | LSRVEEKLKTVKSQLTEVASTLSLVREQLAQ (SEQ ID NO: 26) |
| CREB-Pa-LI: | LMSIEKKLEEITQTLMQIQNELSMIKNELAQ (SEQ ID NO: 27) |

TABLE 3D-continued

Amino Acid Sequences of Coiled-Coil Domain Based MultimerizationDomains

CREB-Pa-LL:    LMSLEKKLEELTQTLMQLQNELSMLKNELAQ (SEQ ID NO: 28)
CREB-Pa-IL:    IMSLEKKIEELTQTIMQLQNEISMLKNEIAQ (SEQ ID NO: 29)
CREB-Pa II:    IMSIEKKIEEITQTIMQIQNEISMIKNEIAQ (SEQ ID NO: 30)
CREB-PaVL:     VMSLEKKVEELTQTVMQLQNEVSMLKNEVAQ (SEQ ID NO: 31)
CREB-Pa LV:    LMSVEKKLEEVTQTLMQVQNELSMVKNELAQ (SEQ ID NO: 32)
ATF2-LI:       LQSIEKKLEDISSLLGQIQSELTLIRNELAQ (SEQ ID NO: 33)
ATF2-LL:       LQSLEKKLEDLSSLLGQLQSELTLLRNELAQ (SEQ ID NO: 34)
ATF2-IL:       IQSLEKKIEDLSSLIGQLQSEITLLRNEIAQ (SEQ ID NO: 35)
ATF2-II:       IQSIEKKIEDISSLIGQIQSEITLIRNEIAQ (SEQ ID NO: 36)

TABLE 4A

Nucleotide Sequence Encoding ATFα Leucine Zipper Domain Variants

ATFα(1)-LI:
CTTAGCTCTATTGAGAAGAAACTTGAGGAGATTACCTCTCAACTGATTCAGATCAGCAATGAA
CTGACCCTTATCCGCAATGAGCTGGCCCAATGA (SEQ ID NO: 48)

ATFα(2)-LI:
CTTAGCTCTATTGAGAAGAAACTTGAGGAGATTACCTCTCAACTGATTCAGATCCGCAATGAA
CTGACCCTTATCCGCAATGAGCTGGCCCAATGA (SEQ ID NO: 49)

ATFα(3)-LI:
CTTAGCTCTATTGAGAAGAAACTTGAGGAGATTACCTCTCAACTGCAACAGATCCGCAATGAA
CTGACCCTTATCCGCAATGAGCTGGCCCAATGA (SEQ ID NO: 50)

ATFα-IL:
ATTAGCTCTTTAGAGAAGAAAATTGAGGAGCTGACCTCTCAAATCCAGCAGCTGCGCAATGA
AATCACCCTTCTTCGTAATGAGATTGCCCAATGA (SEQ ID NO: 51)

ATFα-II:
ATCAGCTCTATTGAGAAGAAAATCGAGGAGATTACCTCTCAAATCATTCAGATTCGCAATGAA
ATCACGCTTATCCGTAATGAGATTGCCCAATGA (SEQ ID NO: 52)

ATFα-LL:
CTTAGCTCTCTTGAGAAGAAACTTGAGGAGCTTACCTCTCAACTGATTCAGCTTCGCAATGAA
CTGACCCTTCTGCGTAATGAGCTGGCCCAATGA (SEQ ID NO: 53)

ATFα-VL:
GTTAGCTCTCTTGAGAAGAAAGTTGAGGAGCTTACCTCTCAAGTGATTCAGCTTCGCAATGAA
GTGACCCTTCTGCGTAATGAGGTTGCCCAATGA (SEQ ID NO: 54)

TABLE 4B

Nucleotide Sequence of Coiled Coil Based Tetramerization Domains

ATF1-LI:
CTTAAATCTATTGAGAACCGGCTTGCCGTTATTGAGAACCAACTGAAAACCATCATTGAAGAG
CTTAAGACCATCAAAGACCTTCTGTCTAACTGA (SEQ ID NO: 55)

ATF1-LL:
CTTAAATCTCTTGAGAACCGGCTTGCCGTTCTTGAGAACCAACTGAAAACCCTGATTGAAGAG
CTTAAGACCCTGAAAGACCTTCTGTCTAACTGA (SEQ ID NO: 56)

ATF1-IL:
ATTAAATCTCTTGAGAACCGGATCGCCGTTCTTGAGAACCAAATCAAAACCCTTATTGAAGAG
ATTAAGACCCTGAAAGACCTTATCTCTAACTGA (SEQ ID NO: 57)

ATF1-II:
ATTAAATCTATTGAGAACCGGATTGCCGTTATTGAGAACCAAATCAAAACCATCATTGAAGAG
ATTAAGACCATCAAAGACCTTATCTCTAACTGA (SEQ ID NO: 58)

ATF1-VL:
GTTAAATCTCTTGAGAACCGGGTTGCCGTTCTTGAGAACCAAGTTAAAACCCTGATTGAAGAG
GTTAAGACCCTTAAAGACCTTGTTTCTAACTGA (SEQ ID NO: 59)

ATF1-LV:
CTTAAATCTGTTGAGAACCGGCTTGCCGTTGTTGAGAACCAACTGAAAACCGTTATTGAAGAG
CTTAAGACCGTTAAAGACCTTCTGTCTAACTGA (SEQ ID NO: 60)

TABLE 4B-continued

Nucleotide Sequence of Coiled Coil Based Tetramerization Domains

CJUN-LI:
CTTGCTCGGATTGAAGAGAAACTTAAAACCATTAAAGCGCAACTGTCTGAGATCGCGTCTACC
CTGAACATGATCCGTGAACAACTGGCCCAATGA (SEQ ID NO: 61)

CJUN-LL:
CTTGCTCGGCTTGAAGAGAAACTTAAAACCCTTAAAGCGCAACTGTCTGAGCTGGCGTCTACC
CTGAACATGCTCCGTGAACAACTGGCCCAATGA (SEQ ID NO: 62)

CJUN-IL:
ATTGCTCGGCTTGAAGAGAAAATTAAAACCCTGAAAGCGCAAATTTCTGAG
CTTGCGTCTACCATTAACATGCTTCGTGAACAAATCGCCCAATGA (SEQ ID NO: 63)

CJUN-II:
ATTGCTCGGATTGAAGAGAAAATCAAAACCATTAAAGCGCAAATCTCTGAG
ATCGCGTCTACCATCAACATGATCCGTGAACAAGCCCAATGA (SEQ ID NO: 64)

CJUN-VL:
GTTGCTCGGCTTGAAGAGAAAGTTAAAACCCTTAAAGCGCAAGTTTCTGAGCTTGCGTCTACC
GTTAACATGCTTCGTGAACAAGTCGCCCAATGA (SEQ ID NO: 65)

CJUN-LV:
CTTGCTCGGGTCGAAGAGAAACTTAAAACCGTTAAAGCGCAACTGTCTGAGGTCGCGTCTACC
CTGAACATGGTTCGTGAACAACTGGCCCAATGA (SEQ ID NO: 66)

JUND-LI:
CTTAGCCGGATTGAAGAGAAACTTAAAACCATTAAATCTCAACTGACTGAGATCGCGTCTACC
CTGTCTCTTATCCGTGAACAACTGGCCCAATGA (SEQ ID NO: 67)

JUND-LL:
CTTAGCCGGCTTGAAGAGAAACTTAAGACCCTGAAATCTCAACTGACTGAGCTTGCGTCTACC
CTTTCTTTGCTGCGTGAACAACTTGCCCAATGA (SEQ ID NO: 68)

JUND-IL:
ATCAGCCGGCTTGAAGAGAAGATTAAGACCCTGAAATCTCAAATCACTGAGCTTGCGTCTACC
ATTTCTCTTCTGCGTGAACAAATTGCCCAATGA (SEQ ID NO: 69)

JUND-II:
ATCAGCCGGATTGAAGAGAAGATTAAGACCATCAAATCTCAAATCACTGAG
ATTGCGTCTACCATTTCTCTTATTCGTGAACAAATTGCCCAATGA (SEQ ID NO: 70)

JUND-VL:
GTTAGCCGGCTTGAAGAGAAGGTTAAGACCCTGAAATCTCAAGTTACTGAG
CTTGCGTCTACCGTCTCTCTTCTGCGTGAACAAGTTGCCCAATGA (SEQ ID NO: 71)

JUND-LV:
CTTAGCCGGGTTGAAGAGAAGCTGAAGACCGTCAAATCTCAACTTACTGAG
GTTGCGTCTACCCTTTCTCTTGTCCGTGAACAACTTGCCCAATGA (SEQ ID NO: 72)

CREB-Pa-LI:
CTTATGTCTATTGAGAAGAAACTTGAGGAGATTACCCAGACTCTGATGCAGATCCAGAATGAA
CTGTCTATGATCAAGAATGAGCTGGCCCAATGA (SEQ ID NO: 73)

CREB-Pa-LL:
CTTATGTCTCTGGAGAAGAAACTTGAGGAGCTTACCCAGACTCTGATGCAGCTTCAGAATGAA
CTGTCTATGCTGAAGAATGAGCTGGCCCAATGA (SEQ ID NO: 74)

CREB-Pa-IL:
ATCATGTCTCTGGAGAAGAAGATCGAGGAGCTTACCCAGACTATCATGCAGCTTCAGAATGA
AATTTCTATGCTGAAGAATGAGATTGCCCAATGA (SEQ ID NO: 75)

CREB-Pa-II:
ATCATGTCTATTGAGAAGAAGATCGAGGAGATCACCCAGACTATCATGCAG
ATTCAGAATGAAATTTCTATGATCAAGAATGAGATTGCCCAATGA (SEQ ID NO: 76)

CREB-Pa-VL:
GTTATGTCTCTTGAGAAGAAGGTTGAGGAGCTTACCCAGACTGTCATGCAG
CTTCAGAATGAAGTTTCTATGCTTAAGAATGAGGTTGCCCAATGA (SEQ ID NO: 77)

CREB-Pa-LV:
CTGATGTCTGTCGAGAAGAAGCTTGAGGAGGTTACCCAGACTCTCATGCAG
GTTCAGAATGAACTTTCTATGGTTAAGAATGAGCTTGCCCAATGA (SEQ ID NO: 78)

ATF2-LI:
CTTCAGTCTATTGAGAAGAAACTTGAGGACATTAGCTCTCTTCTGGGTCAGATCCAATCTGAA
CTGACCCTTATCCGCAATGAGCTGGCCCAATGA (SEQ ID NO: 79)

TABLE 4B-continued

Nucleotide Sequence of Coiled Coil Based Tetramerization Domains

ATF2-LL:
CTTCAGTCTCTTGAGAAGAAACTTGAGGACCTTAGCTCTCTTCTGGGTCAGCTGCAATCTGAG
CTGACCCTTCTGCGCAATGAGCTGGCACAATGA (SEQ ID NO: 80)

ATF2-IL:
ATTCAGTCTCTGGAGAAGAAAATCGAGGACCTTAGCTCTCTTATTGGTCAGCTTCAATCTGAA
ATCACCCTTCTTCGCAATGAGATTGCCCAATGA (SEQ ID NO: 81)

ATF2-II:
ATTCAGTCTATTGAGAAGAAAATCGAGGACATTAGCTCTCTTATTGGTCAGATTCAATCTGAA
ATCACCCTTATCCGCAATGAGATTGCCCAATGA (SEQ ID NO: 82)

TABLE 5

Designed Hinge Sequences

D30: KAQASSVPTA QPQAEGSLAK ATTAPATTRN
(SEQ ID NO: 43)

D35: KAQASSVPTA QPQAEGSLAK ATTAPATTRN TGRGG
(SEQ ID NO: 44)

ED: KAQASSVPTA QPQAEGSLAK ATTAPATTRN TGRGGEEKKK
EKEKEEQEER ETKTPE (SEQ ID NO: 45)

EDC: KAQASSVPTA QPQAEGSLAK ATTAPATTRN TGRGGEEKKK
EKEKEEQEER ETKTPEC (SEQ ID NO: 46)

D63: KAQASSVPTA QPQAEGSLAK ATTAPATTRN TGRGGEEKKK
EKEKEEQEER ETKTPECPSH TQP (SEQ ID NO: 47)

Example 4

This example shows that residues at positions other than a and d can influence the multimeric status of a chimeric protein of the invention. This example also describes how other sequences can be produced in accordance with the invention.

Five candidate leucine zipper domains were selected based on a search of public databases (Table 3B). Multimerization domains were then designed by replacing wild type residues at positions a and d with leucine or isoleucine (Table 3D); they were synthesised by PCR according to the nucleotide sequences in Table 4B. Each variant was expressed and purified as a component of a chimeric multimeric fusion protein.

With L at position a and I at position d, four of the five multimer domains formed tetramer, but the fifth, JUND-LI, formed trimer. With I at position a and L at position d ATF-1 formed trimer, but ATF-2, CJUN, and CREB formed dimers. When L was placed at both positions a and d, ATF-2 and CREB formed tetramers, ATF-1 and CJUN formed trimers, and JUND formed dimer. Isoleucine at both positions a and d formed either trimer or dimer. These results may be contrasted with those obtained with ATFα (Example 1) where the combinations at a and d IL and LI formed tetramer while II and LL formed trimer. The data therefore indicate that sequences outside the a and d positions can modulate the type of multimer formed.

The residues at positions b, c, e, f, and g form an interlocked network of inter- and intra-helical interactions that influence the geometry of the helical bundle. This network intra- and inter-helical interactions can be analyzed from three-dimensional models. To do so, a model of the multimerization domain is constructed by homology using a coiled coil of the desired multimerization state as a template. After substituting the sequence of the domain to be analyzed in the proper register relative to the heptad repeat, the structure is energy minimized. Keeping in mind the possibility of alternative side chain rotamers, the surface residues are then analyzed by inspection. If a substitution is contemplated, the propagated effect on the entire network is considered. For example, changing an e position to a residue that can make a salt bridge to a g position in a neighboring helix may cause a third residue previously interacting with the g position to also change its interacting partner(s).

The effect of a substitution can be predicted with frequent success by this method. In order to confirm the predicted effect, the substituted multimer domain can be screened for its multimerization or other properties (e.g., stability or tightness). For example, the multimeric form produced can be determined by HPLC and/or ultracentrifugation assay methods as described herein (Example 6); the effect on tightness of multimerization can be assayed by determining melting profiles of a polypeptide having the multimerization domain.

Example 5

This example describes expression and purification of multimeric Fab protein.

To produce a multimeric Fab, a SacI/EcoRI DNA fragment encoding the ED hinge (Table 5) derived from IgD and a modified ATFα coiled-coil domain, ATFα(1)-LI+S, was cloned at 3'-end of the $C_H1$ coding sequences of Fab19 in the Fab19/Tet plasmid (FIG. 1). This plasmid was designated CFY 196.

To produce the Fab19 and the tetrameric CFY196 proteins, cultures of the *E. coli* strain JM83 expressing the Fab19/Tet or CFY196 plasmids were grown in selective TB medium to an $OD_{600}$ of 2.0. After induction by addition of IPTG to a final concentration of 0.2 mM and incubation for 8 hours at room temperature, cells were harvested by centrifugation at 4,000 g for 15 minutes at 4° C. The cell pellet was suspended in 50 ml wash buffer (50 mM Tris, pH 8.0, 150 mM NaCl, 50 μM PMSF and 5 mM EDTA) per liter culture and repelleted by centrifugation at 4,000 g for 15 minutes at 4° C. and frozen. Frozen cell pellets were resuspended in 20 ml/gram wet weight pellet of a lysis buffer (50 mM Tris, pH 8.0, 200 mM NaCl, 5 mM EDTA, 5 mM EGTA, 50 μM PMSF and 0.1 mg/ml lysozyme), and after incubation on ice for 30 minutes the pellets were sonicated, and the lysates clarified by centrifugation at 23,000 g for 30 minutes. The supernatant, containing soluble protein, was adjusted to 1M NaCl and loaded on a Protein A column (Amersham/Pharmacia). The column was then washed extensively with 2M NaCl, 25 mM Tris, pH 8.0, 5 mM EDTA and the proteins eluted with 0.1 M glycine, pH 2.5. Eluent pH was neutralized with 1/10 volume of 1 M Tris base pH 9.0.

For the purification of monovalent Fab proteins, protein-containing fractions were pooled and dialyzed against TBS and stored at 4° C. For the purification of multimeric Fab fusion proteins, fractions from the protein A column were dialyzed against 200 mM KCl in 50 mM Hepes pH 7.5, then further purified over a hydroxyapatite column (Macroprep Ceramic Hydroxyapatite Type II, Biorad). After binding the protein in dialysis buffer, the column was washed with binding buffer, then with 200 mM KCl/10 mM K phosphate/50 mM Hepes, pH 8.0. The multimeric Fab proteins were eluted with a phosphate gradient in 500 mM KCl/50 mM Hepes, pH 8.0. Positive fractions were pooled and dialyzed against TBS.

Figure 2:
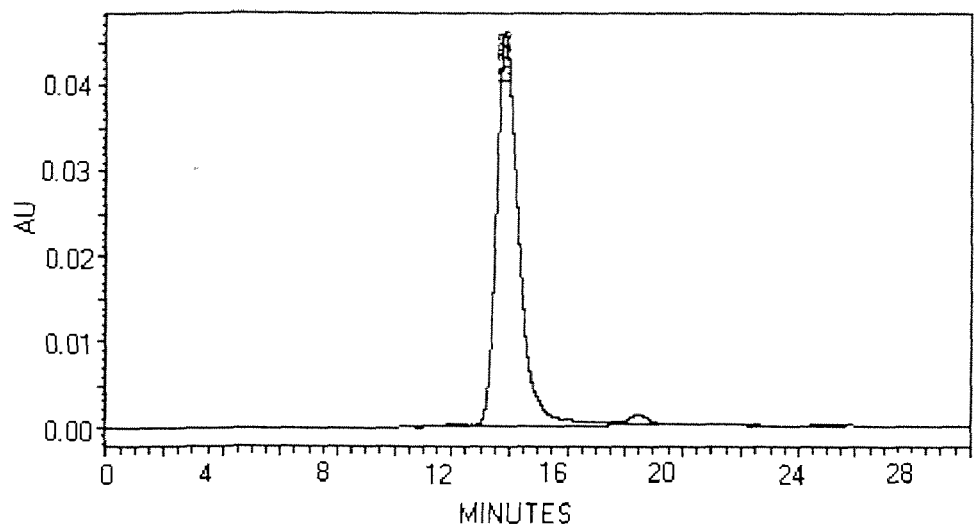
FIGS. 2A-2B show characterization of purified CFY196. A) Purified CFY196 runs as a single peak on the HPLC size exclusion column; B) Coomassie Blue stained SDS-PAGE of purified CFY196, which is shown as two components, light chain (LC) and composite heavy chain (CHC) bands (lane 1). Molecular weight markers are shown in lane 2.
Figure 2:
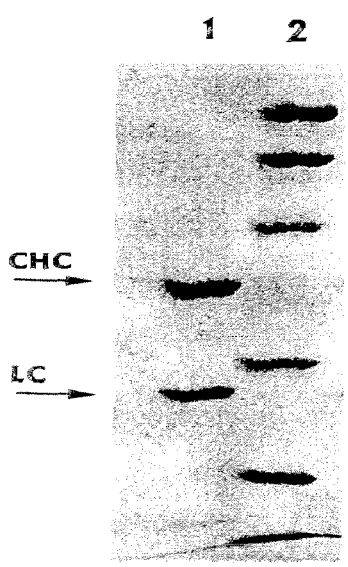

The yield was 1-2 mg/liter of culture in shake flask. The purity of protein preparations were determined by size exclusion chromatography and SDS-PAGE gel (FIG. 2).

Example 6

This example describes characterization of the multimeric status of Fab-ATFα domain fusion proteins.

Figure 3A:
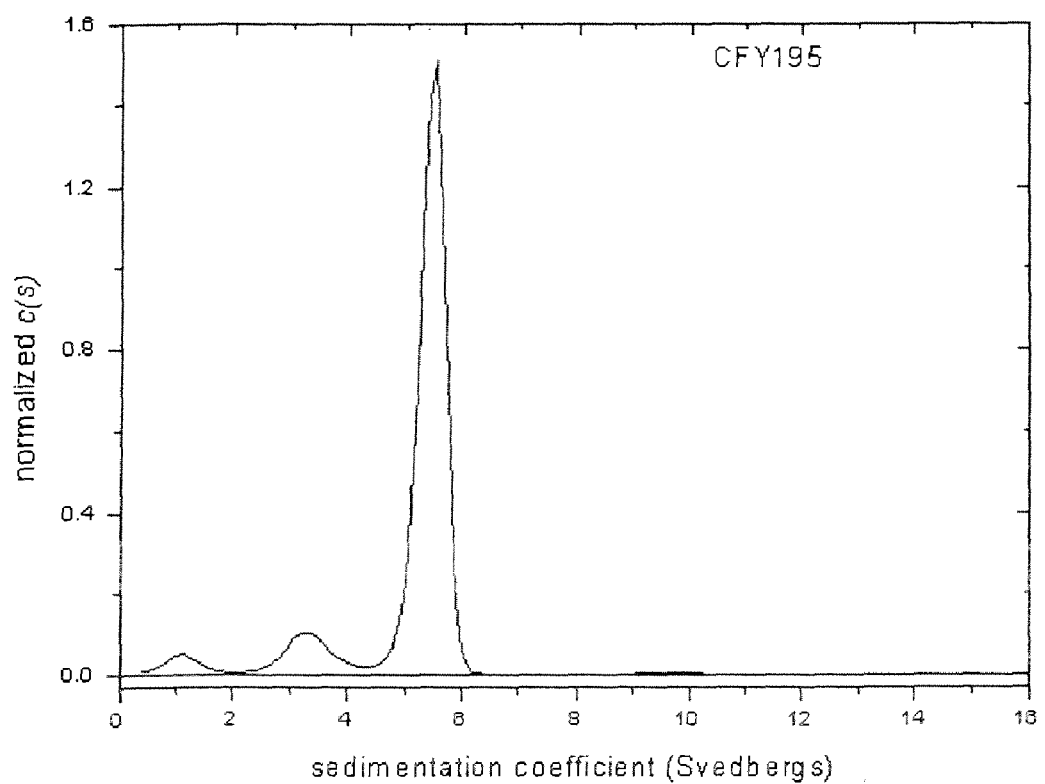
FIGS. 3A-3C show processed sedimentation velocity data from A) CFY 195 (peak is at 5.5 S); B) CFY192B; and C) CFY196 (peaks at 6.55). Note the narrower peak for CFY196.
Figures 3B, 3C:
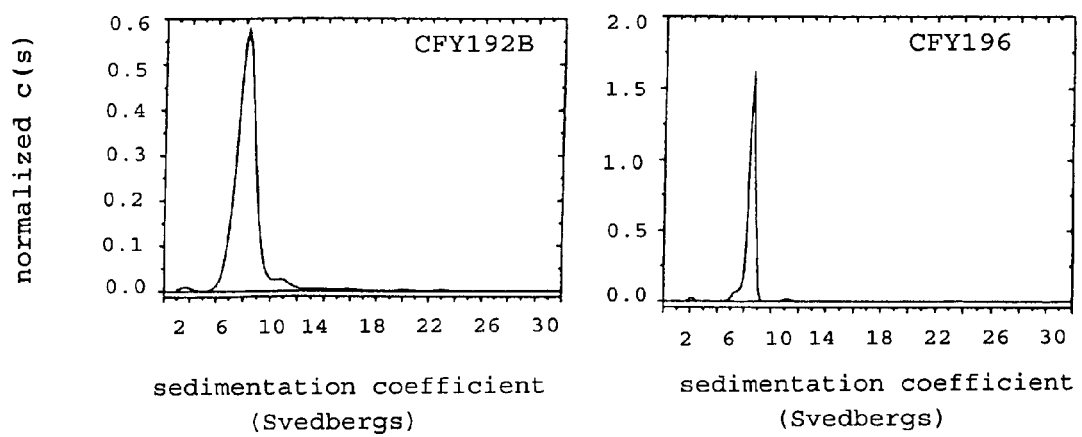

Two assays are described, a sedimentation velocity assay which can determine multimerization state and cart distinguish between multimers of different tightness, and an HPLC assay that can distinguish multimerization states after being correlated with the sedimentation velocity data. Sedimentation velocity measures the movement of a solute boundary as the solute moves through solvent under the influence of a centrifugal force. The data are a series of boundary positions recorded over time. The raw data is then processed to give a distribution of sedimentation coefficients (FIG. 3). The large peak shows the sedimentation coefficient for the major species in the sample. The number of peaks is an indication of purity, and the broadness of the major peak indicates the homogeneity of the major species.

The oligomeric state of purified multimeric Fab fusion proteins was determined by sedimentation velocity using analytical ultracentrifugation (Modern Analytical Ultracentrifugation, T M Schuster and T M Laue, eds. (1994) Birkhauser, Boston) in combination with light scattering data (Wen, et al., *Analytical Biochem* 240:155 (1996)). Trimeric Fab-ATFα domain fusion proteins sediment at about 5.5 S, and tetrameric proteins sediment at 6.5 S. The results of sedimentation studies on Fab-ATFα domain fusion proteins are summarized in Table 6.

By correlation with sedimentation velocity data, the multimerization state of additional ATFα-based domains was determined by size exclusion HPLC. HPLC size exclusion chromatography was performed on a column selected to resolve species of chimeric multimers ranging from dimers through pentamers. The selected column also resolved species including the Fab moiety of the chimera: Tetramers (6.5S by ultracentrifugation) consistently eluted from the column at 13.7±0.1 min.; trimers (5.5S) eluted at 14.0±0.1; and dimers (4.5S) eluted at 15.0±0.1 min. Data on additional domains is listed in Table 7 along with those determined by sedimentation. The multimeric status of domains derived from ATF1, ATF2, CJUN, JUND and CREB leucine zippers are summarized in Table 8.

TABLE 6

Multimer Formation

| Construct | Hinge-ATFα Domains | Sedimentation coeff | Multimer |
|---|---|---|---|
| CFY192B | ED-ATFα(2)-LI | 6.5 S | tetramer |
| CFY193B | ED-ATFα(2)-LL | 5.5 S | trimer |
| CFY195 | ED-ATFα(2)-II | 5.5 S | trimer |
| CFY196 | ED-ATFα(1)-LI + S | 6.5 S | tetramer |
| CFY197 | ED-ATFα(3)-IL | 6.5 S | tetramer |
| CFY484 | $D_{30}$-ATFα(2)-LI | 6.5 S | tetramer |

TABLE 7

Multimer Formation by ATFα Variants

| ATFα Variant | Hinge | Protein Fused With | Multimeric Status |
|---|---|---|---|
| ATFα-WT | ED-, | Fab4.8 | Tetramer |
| ATFα(1)-LI | IgG3 | Thioredoxin | Tetramer |
| ATFα(1)-LI | D-, ED- | Fab4.8, Fab17, Fab19 | Tetramer |
| ATFα(2)-LI | D30-, ED- | Fab4.8, Fab17, Fab19 | Tetramer |
| ATFα(3)-LI | D30-, ED- | Fab17 | Tetramer |
| ATFα-LL | ED-, | Fab4.8, Fab19 | Trimer |
| ATFα-II | D30-, ED- | Fab4.8, Fab19 | Trimer |
| ATFα-IL | ED-, | Fab4.8, Fab19 | Tetramer |
| ATFα-VL | ED-, | Fab4.8 | Dimer & Tetramer |

Figure 5:
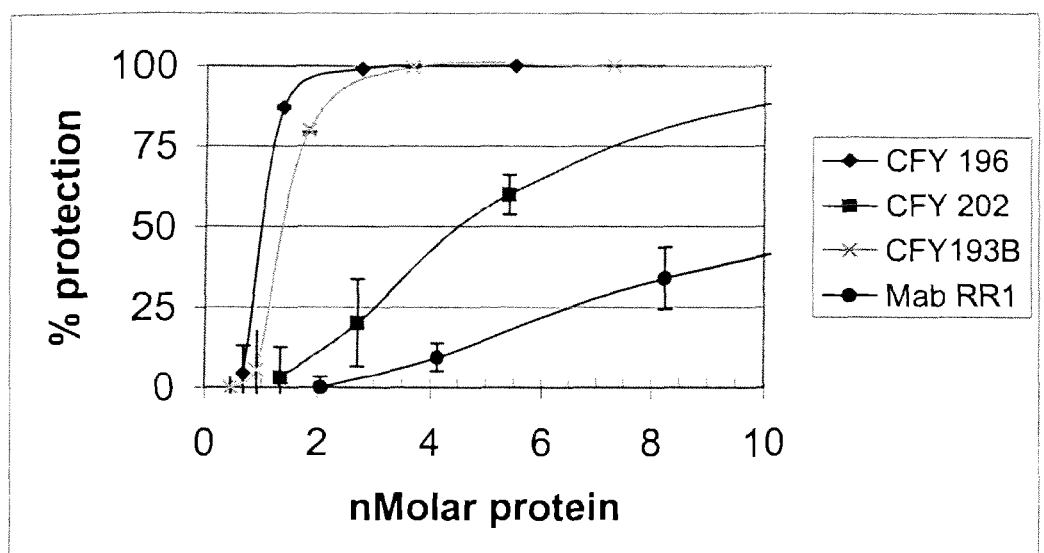
FIG. 5 shows protection of HeLa cells from HRV15 infection with monovalent Fab19, bivalent monoclonal antibody RR/1, bivalent CFY202, trimeric CFY193B, and tetrameric CFY196.

Sedimentation data also allows distinguishing between tetramers. For example, CFY 192B, 196 and 484 have the same a and d amino acids, and all form predominantly tetramers. These proteins, however, bear variations in sequence elsewhere. Examination of the c(s) vs. S plots for CFY196 and CFY192B reveals that the former is superior (FIG. 5). The distribution of sedimentation coefficient fitted for CFY196 is much narrower than that for CFY192B indicating a more homogeneous tetrameric population for CFY196.

Fab19 ED when fused to ATF(1)α-IL (SEQ ID NO:162) forms a tetramer whose sedimentation velocity analysis showed a broad peak (FIG. 7A). Changing a serine to arginine at position e of the third repeat (SEQ ID NO:163), which creates a new potential interheiical salt bridge, gave slight improvement (FIG. 7B). Combining these changes with an additional mutation of the isoleucine at position b of the third repeat to glutamine (SEQ ID NO:5) gave a much narrower sedimentation distribution (FIG. 7C). Sequences of ATFα-IL mutants:

```
                   1              2              3              4              5
Repeats:     a b c d e f g  a b c d e f g  a b c d e f g  a b c d e f g  a b c ATFα(1)-IL:  I S S L E K K  I E E L T S Q  I I Q L S N E  I T L L R N E  I A Q    (SEQ ID NO: 162)

ATFα(2)-IL:  I S S L E K K  I E E L T S Q  I I Q L R N E  I T L L R N E  I A Q    (SEQ ID NO: 163)

ATFα(3)-IL:  I S S L E K K  I E E L T S Q  I Q Q L R N E  I T L L R N E  I A Q    (SEQ ID NO: 5)
```

TABLE 8

Multimer Formation by Other Multimerization Polypeptides

| Domains | Multimeric Status |
|---|---|
| CREB-Pa-LI | Tetramer |
| CREB-Pa-LL | Tetramer |
| CREB-Pa-IL | Dimer |
| CREB-Pa-II | degradation products |
| JUN-D-LI | Trimer |
| JUN-D-LL | Dimer |
| JUN-D-II | degradation products |
| JUN-D-IL | degradation products |
| CJUN-LI | Tetramer |
| CJUN-LL | Trimer |
| CJUN-IL | Dimer |
| CJUN-II | degradation products |
| ATF-1-LI | Trimer |
| ATF-1-LL | Trimer |
| ATF-1-IL | Trimer |
| ATF-1-II | Trimer |
| ATF2-LI | Tetramer |
| ATF2-LL | Tetramer |
| ATF2-IL | Dimer |
| ATF2-II | degradation products |

Figure 4:
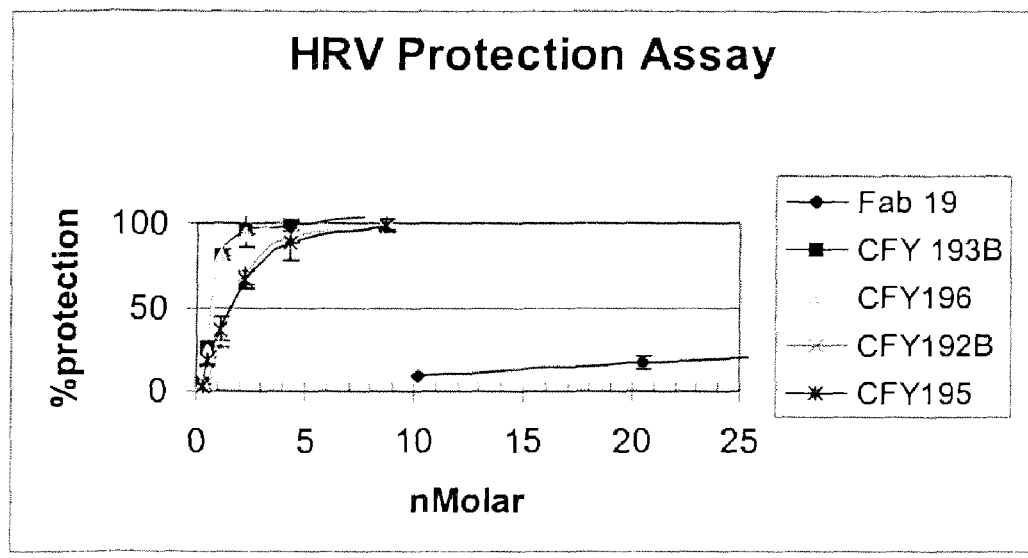
FIG. 4 shows protection of HeLa cells from infection by HRV14 with monovalent Fab and multivalent Fab-ATFα domain chimeric proteins. Chimeric proteins are denoted as follows: CFY193B, Fab-ED-ATFαLL; CFY196, Fab-ED-ATFα(1)LI+S; CFY192B, Fab-ED-ATFα(2)LI; and CFY195, Fab-ED-ATFαII.

The sedimentation data correlate well with the results of cell based functional assays (see, e.g., Example 7). These assays indicate that tetrameric proteins exceed trimers in cell protective ability, and trimeric and tetrameric proteins provide greater protection than monovalent Fab. The most homogenous tetramer provides the best protection (FIG. 4).

Example 7

This example describes biological activities of monovalent Fab19 anti human ICAM-1 protein and multivalent Fab19-EDATFα domain fusion proteins. This example also describes data indicating that trimeric and tetrameric Fab19-EDATFα proteins provide greater protection of cells from HRV infection than monovalent Fab19 and bivalent monoclonal antibody.

An HRV protection assay was performed to compare the abilities of the monovalent Fab19 protein and multivalent Fab19-based proteins to protect cells from infection. HeLa cells were plated $1\times10^5$ per well in a 48-well tissue culture dish 24 hours before the assay. Growth medium was removed and 100 μl of multivalent or monovalent proteins diluted to the indicated concentrations added to each well. The plates were incubated for one hour in a 37° C. incubator, the solution was removed and 200 μl HRV15 (at MOI of 1) added and then incubated for one hour at 33° C. Cells were washed and 1 ml/well growth medium added. Infected cells were incubated at 33° C. for 48 hours, the medium removed and the remaining viable cells stained with crystal violet. Bound crystal violet was extracted with 3 ml methanol per well, then the amount of cell staining was quantified by measuring the $A_{570}$.

The results of the protection assay are illustrated in FIG. 4. The percentage protection is calculated for each data point in triplicate using the formula:

$$\%\ \text{protection} = \frac{(100)(\text{Absorbance of sample} - \text{Absorbance of virus only})}{(\text{Absorbance of uninfected cells} - \text{Absorbance of virus only})}$$

The protective efficacy is quantitated as $EC_{50}$, the dose of antibody that gives 50% protection. Based on the data, the $EC_{50}$ of Fab19 is 76 nM. The tetrameric proteins CFY192B and CFY196 are more effective than the trimeric CFY192B and CFY195. In this group of multimers based on ATFα, CFY196 (Fab19-EDATFα(1)-LI+S) demonstrated the highest protection ($EC_{50}$ of 0.73 nM), which is 104 times greater protection than monovalent Fab 19 protein.

In another study, the protective efficacy of monovalent Fab19, bivalent anti-ICAM-1 monoclonal antibody RR/1 (Chemicon), bivalent CFY202, trimeric CFY193B and tetrameric CFY196 were compared (FIG. 5). While monovalent Fab 19 had an $EC_{50}$ of greater than 200 nM, and bivalent RR/1 has an $EC_{50}$ greater than 10 nM, the $EC_{50}$ of CFY 202 was 4.5 nM, of CFY 193B was 1.35 nM and that of CFY 196 was 0.97 nM. These data indicate that tetramer provided the greatest protective efficacy followed by trimer, dimer and monomer.

Example 8

This example describes the construction and multimeric characterization of a non-Fab chimeric polypeptide of the invention, a thioredoxin-ATFαLI fusion protein.

To demonstrate that ATFα leucine zipper domain variants can induce tetrameric complexes when fused with proteins other than Fab, the hinge-ATFα(1)-LI+$SG_3H_6$ fragment was fused to the C-terminus of thioredoxin in the expression vector pBAD-thio (Invitrogen). The expression construct, pBAD-thio-hinge-ATFα(1)-LI-+$SG_3H_6$, was transferred into the *E. coli* strain TOP-10 and grown in selective TB medium to an $OD_{600}$ of 0.8. After induction by addition of arabinose to 0.02% final concentration, and incubation overnight at room temperature, cells were harvested by centrifugation at 4,000 g for 15 minutes at 4° C. The cell pellets were suspended in lysis buffer (20 mM sodium phosphate, pH 8.0, 1% Triton X-100, 500 mM NaCl, 40 mM imidazole, 1 mM β-mercaptoethanol), 0.2 mM PMSF, 0.5 mg/ml lysozyme and incubated on ice for 20 minutes. The cells were sonicated, and another aliquot of PMSF was added. Cell debris was pelleted by centrifugation at 23,000 g and the clarified sonicate was filtered and fractionated by metal affinity chromatography.

Induced histidine-tagged proteins were bound to a Hi Trap metal chelating column (Amersham/Pharmacia) equilibrated with $Ni^{2+}$ according to the manufacturer's directions. The column was then washed with four column volumes of buffer consisting of 100 mM imidazole, 20 mM sodium phosphate, pH 7.4, 500 mM NaCl. Proteins were eluted from the column with 20 mM sodium phosphate, pH 7.4, 1 M Imidazole and collected in fractions. Protein fractions were pooled and dialyzed at 4° C. against phosphate buffered saline (PBS).

The molecular weight of the thioredoxin-ATFα(1)-LI fusion protein was determined by size exclusion chromatography, A Superdex 200 column (7.5 mm×25 cm) was equilibrated in TBS buffer (50 mM Tris-HCl, pH8.0, 150 mM NaCl) at a flow rate of 0.4 ml/min. The column was calibrated with standard proteins (ribonuclease A, 13.7; chymotrypsinogen A, 25 kDa; ovalbumin, 43 kDa; bovine serum albumin, 66 kDa; alcohol dehydrogenase, 150 kDa; and β-amylase, 200 kDa). The purified thioredoxin-ATFαLI1 fusion protein was analyzed separately at the same conditions as standard proteins.

The calculated molecular weight of a monomeric thioredoxin-ATFα(1)-LI-+$SG_3H_6$ fusion protein is 19.6 kDa. However, the calculated molecular mass of purified fusion protein is about 78 kDa. This result demonstrates that the thioredoxin-ATFα(1)LI-+$SG_3H_6$ fusion protein exists as a tetramer.

Example 9

This example describes inhibiting and treating respiratory syncytial virus (RSV) infection by multivalent ICAM-1 binding proteins of the invention.

RSV appears to bind to ICAM-1 via F protein on the surface of RSV; F protein is also the target of neutralizing antibodies against RSV. A recently published article purportedly found that human respiratory syncytial virus (RSV) infection of human epithelial cells could be inhibited either by pre-treating RSV with soluble ICAM-1 or pre-treating cells with an anti-ICAM-1 monoclonal antibody (Behera et al., *BBRC* 280:188 (2001)). However, very high antibody concentration (200-400 microgram/ml, >1 mM) was required to achieve the apparent inhibition of RSV infection indicating that a monoclonal antibody is unlikely to be an effective therapy against RSV.

Given the high concentration of the monoclonal antibody required for inhibition of RSV infection in vitro, RSV may have relatively high binding affinity, or avidity, for ICAM-1. If so, a multimeric (dimer, trimer, tetramer, pentamer or even higher order oligomer) ICAM-1 binding protein will have better efficacy against RSV infection than a monovalent ICAM-1 antibody. Additionally, although a full-blown RSV infection is a systemic disease, the virus first invades the body at the upper respiratory tract, especially at the nasopharynx area. Blocking RSV from the upper respiratory tract will prevent the entry of RSV, and therefore prevent RSV from invading the lower respiratory tract.

Although not wishing to be bound by theory, multivalent ICAM-1 binding protein appears to block the RSV foothold or entryway into cells of the upper respiratory tract. Consequently, free-floating RSV particles are re-routed by the normal mucocilliary clearing system into the gastrointestinal tract and become harmless.

Example 10

This example describes the construction and expression of polypeptides composed of two different binding specificities.

To produce a molecule with tetrameric binding capacity from a dimerization domain the multimerization domain can be at the center of a molecule linking Fab from two different antibody molecules (see, e.g., FIG. 6A). Alternatively, a trimerization or tetramerization domain could be used to produce hexavalent and octavalent molecules, respectively.

In the bispecific multimeric protein, the Fab moities illustrated with different hatching could have different specificities, such as anti-CD-3 and anti-CD-19. The Fab portion of each protein, consisting of the heavy and light chains, would be linked by a linker sequence to a dimerization domain, illustrated as a hexagon in FIG. 6A. This polypeptide is produced from one tricistronic RNA molecule. Alternatively, three promoters could drive the expression of three distinct polypeptides. The coding sequence for the first polypeptide chain translated from this message is illustrated by the hatched box in FIG. 6B, representing the anti-CD-3 light chain (LC-1). The second DNA fragment encodes the central chimeric polypeptide consisting of the anti-CD-3 heavy chain (HC-1) linked to a long hinge derived from IgD, followed by a dimerization domain, a second hinge, followed by the anti-CD19 light chain (LC-2). The third RNA, illustrated by the white box in FIG. 6B, would encode the anti-CD-19 heavy chain (HC-2).

An alternative expression construct in which the HC-2 sequences and the LC-2 sequences are switched for sequences encoding an scFv would also be possible, if the affinity of the scFv was as high as desirable.

To express a bispecific tetravalent molecule from a tricistronic message, three DNA fragments would be prepared. The first is an Nde I/Xba I fragment consisting of the light chain from the anti-CD-3 Fab and the bulk of an intervening sequence (IVS1) which includes a ribosome binding site. Downstream from this fragment the XbaI/SpeI restriction fragment consisting of six pieces fused together using PCR is ligated: the remainder of the IVS1, the heavy chain of Fab, a hinge derived from IgD, the CREB-IL dimerization domain, a second hinge derived from IgD, the light chain of anti-CD-19, and the bulk of the second intervening sequence (IVS2). The third SpeI/HindIII restriction fragment would contain the remainder of IVS2, the heavy chain of anti-CD-19, and a terminator sequence. Each of the IVS contain a ribosome binding site, and the 3' end of the construction contains the bacteriophage $\lambda t_0$ terminator (TER). When translated, each of the three polypeptides will be preceded by an enterotoxin II signal sequence (stII).

For other bispecific molecules, the multimerization domain indicated by the filled box would be replaced by alternative multimerization sequences to form tetravalent, hexavalent, octavalent or higher order binding arms. These three DNA coding sequences could be driven by multiple promoters, or be encoded on distinct vectors. A similar constuct could also be used for bispecific antibodies when two Fab molecules of different specificity share a common light chain. In this instance, the sequences encoding HC-2 in FIG. 6B would replace those of LC-2, and the TER sequences would replace IVS2. This expression vector would then produce two polypeptide chains in a biscistronic message.

Example 11

This example shows how amino acids adjacent to multimerization domains of the invention can be modified to modulate stability or tightness of the multimers that form.

In chimeric proteins of the invention with the coiled coil domain at the C terminus, the C terminus of the multimerization domain is exposed to solvent. An extra amino acid can be added to the C terminus to make a more stable, hydrophilic ending for the protein. In general, by considering the last two amino acids in the coiled coil domain a terminal amino acid can be selected to add to the C terminus that will not disturb the interactions in which these residues participate. For ATFα (1)-LI, a serine fits these criteria. A serine in this position can stabilize the fold of the multimerization domain by allowing the formation of a series of water-mediated hydrogen bonds that provide a hydrophilic termination for the C terminus of the coiled coil.

ATFα(1)-LI (SEQ ID NO:1) was modified by the addition of a C terminal serine (SEQ ID NO:154). When this multimerization domain was used in an anti-ICAM antibody chimera (CFY196), the purified protein multimer (tetramer) was found to give an exceptionally narrow distribution of sedimentation coefficient (FIG. 3C, Example 6), which indicates tighter multimerization, (i.e., the $K_D$ decreases) for the subunits that comprise the multimer. The sequence of ATF(1)α-LI+S:

|  | 1 | 2 | 3 | 4 | 5 |
|---|---|---|---|---|---|
| Repeats: | a b c d e f g | a b c d e f g | a b c d e f g | a b c d e f g | a b c d |
| ATFα(1)-LI+S: | L S S I E K K | L E E I T S Q | L I Q I S N E | L T L I R N E | L A Q S (SEQ ID NO: 154) |

Example 12

This example describes the construction of pentamers with a method of the invention.

To construct a pentamer, the multimerization domain ATFα-II (SEQ ID NO:6), which forms trimers when used in a chimeric anti-ICAM antibody, termed CFY195, was selected. This sequence was chosen because the beta branched isoleucine residues can pack efficiently in the hydrophobic core of a pentamer. Residues at the interface between the hydrophobic core and the solvent exposed exterior of the domain must be changed to be more hydrophobic in order to change the trimer to a pentamer. Accordingly, four residues at e and g positions were changed to leucine. Two additional changes were made at one b and one c position to adjust the network of inter- and intra-helical interactions to favor pentamer formation. Both of these mutations, which change hydrophobic residues to hydrophilic residues, provide proper orientation of interacting interhelical surfaces. This sequence was designated ATFα-II-g (SEQ ID NO:159).

Using overlapping oligonucleotides, both ATFα-II-g and several variants (Table 9) containing subsets of the mutations in ATFα-II-g were generated by PCR, subcloned, and sequenced in their entirety. These all have isoleucine in their a and d positions, but differ in the six amino acids that are underlined in Table 9. These domains were each fused to Fab19 and the ED hinge and assessed for their multimerization state by size-exclusion chromatography as described in Example 6.

Multimeric proteins composed of Fab 19, an ED hinge and the multimerization domains ATFα-II-a through ATFα-II-g (SEQ ID NO:155-159) exhibited a retention time greater than trimeric CFY195, but a, b, and c eluted from the HPLC column as broad peaks, indicating substantial heterogeneity. Only the ATFα-II-f and ATFα-II-g multimers produced the homogeneous species and eluted before tetramer, at a retention time expected for pentamer. The activity of ATFα-II-g multimer was measured in a cell protection assay as described in Example 7. It was found to have similar protective ability to tetrameric CFY196 and superior ability to trimeric CFY195.

TABLE 9

ATFα-II Leucine Zipper Domain Variants

| | 1 | 2 | 3 | 4 | 5 | |
|---|---|---|---|---|---|---|
| Repeats: | a b c d e f g | a b c d e f g | a b c d e f g | a b c d e f g | a b c | |
| ATFα-II: | I S S I E K K | I E E I T S Q | I I Q I R N E | I T L I R N E | I A Q | (SEQ ID NO: 6) |
| ATFα-II-a: | I S S I E K L | I E E I L S Q | I I Q I R N L | I T L I L N E | I A Q | (SEQ ID NO: 155) |
| ATFα-II-b: | I S S I E K K | I E E I L S Q | I Q Q I R N L | I T S I L N E | I A Q | (SEQ ID NO: 156) |
| ATFα-II-c: | I S S I E K L | I E E I L S Q | I Q Q I R N L | I T L I R N E | I A Q | (SEQ ID NO: 157) |
| ATFα-II-f: | I S S I E K L | I E E I L S Q | I Q Q I R N L | I T S I R N E | I A Q | (SEQ ID NO: 158) |
| ATFα-II-g: | I S S I E K L | I E E I L S Q | I Q Q I R N L | I T S I L N E | I A Q | (SEQ ID NO: 159) |

To further demonstrate that one can change a trimer to a higher order multimer by enlarging the hydrophobic core, a pentamer in the context of another coiled-coil domain, ATF-1, was produced. In Table 10 is the sequence of ATF1-II and a variant, ATF1-IIa, designed to form pentamers. The two sequences differ at the positions indicated by underlined amino acids. Comparison by HPLC of two chimeric proteins prepared from these domains indicate that the amino acid alterations changed the trimeric protein prepared from ATF1-II into a higher order multimer.

TABLE 10

ATF1-II Leucine Zipper Domain Variants

| | 1 | 2 | 3 | 4 | 5 | |
|---|---|---|---|---|---|---|
| Repeats: | a b c d e f g | a b c d e f g | a b c d e f g | a b c d e f g | a b c | |
| ATF1-II: | I K S I E N R | I A V I E N Q | I K T I I E E | I K T I K D L | I S N | (SEQ ID NO: 12) |
| ATF1-II-a: | I K S I E N L | I A Q I L N Q | I K T I I E L | I K T I L D L | I S N | (SEQ ID NO: 160) |

Example 13

This example describes a competition ELISA assay for evaluation of binding affinity of monomeric and multimeric Fab antibodies.

A tetrameric Fab19, termed 196TGC, conjugated with horesradish peroxidase (HRP) was developed for use as a tracer. A cysteine was introduced into a tetratmeric anti-ICAM antibody by adding the sequence TGC to the C terminus of a chimeric Fab19-ED protein containing the ATF(1)α-LI multimeriztion domain (196TGC). HRP was chemically coupled to 196TGC using EZ-Link maleimide activated HRP (Pierce). The sequence of the 196TGC multimerization domain:

| | 1 | 2 | 3 | 4 | 5 | |
|---|---|---|---|---|---|---|
| Repeats: | a b c d e f g | a b c d e f g | a b c d e f g | a b c d e f g | a b c d f g | |
| ATFα(1)-TGC: | L S S I E K K | L E E I T S Q | L I Q I S N E | L T L I R N E | L A Q T G C | (SEQ ID NO: 161) |

A 96-well EIA plate (Corning, Inc.) was coated with 100 µl/well soluble ICAM-1 (Bender MedSystems) at 1 µg/ml in 0.1 M NaHCO$_3$. After washing with TBST (50 mM Tris, pH8.0, 150 mM NaCl, 0.05% Tween-20), the plate was blocked with 3% non-fat milk in TBST at room temperature for 1 hour. After washing with TBST, anti-ICAM-1 Fab samples (monomer or multimer) diluted serially 1% non-fat milk/TBST solution were added and incubated at room temperature for 1 hour. After washing with TBST, the plate was incubated with the horseradish peroxidase-conjugated anti-ICAM-1 tetrameric antibody (196TGC-HRP) diluted 1:50,000 in 1% non-fat milk/TBST at room temperature for 2 hours. The plate was washed thoroughly with TBST and 100 µl/well 3,3',5,5'-tetramethybenzidine substrate solution (Kirkegaard and Perry Laboratories) was added. After 15 min incubation, the color development was stopped by adding 100 ml/well 0.12 N HCl and the absorbance of the wells at 450 nm was measured by a plate reader (ICN).

The percentage of inhibition of tracer antibody (196TGC-HRP) binding was calculated as follows:

$$\% \text{ Inhibition} = 100 \times (A_0 - A_s)/A_0$$

Where $A_0$ is OD$_{450}$ of the reference well without samples (196TGC-HRP only); $A_s$ is the OD$_{450}$ reading from the diluted sample. The relative binding affinity of the anti-ICAM-1 antibodies were represented by the protein concentration that blocks tracer antibody (TGC-HRP) at 50% (IC$_{50}$).

Figure 8:
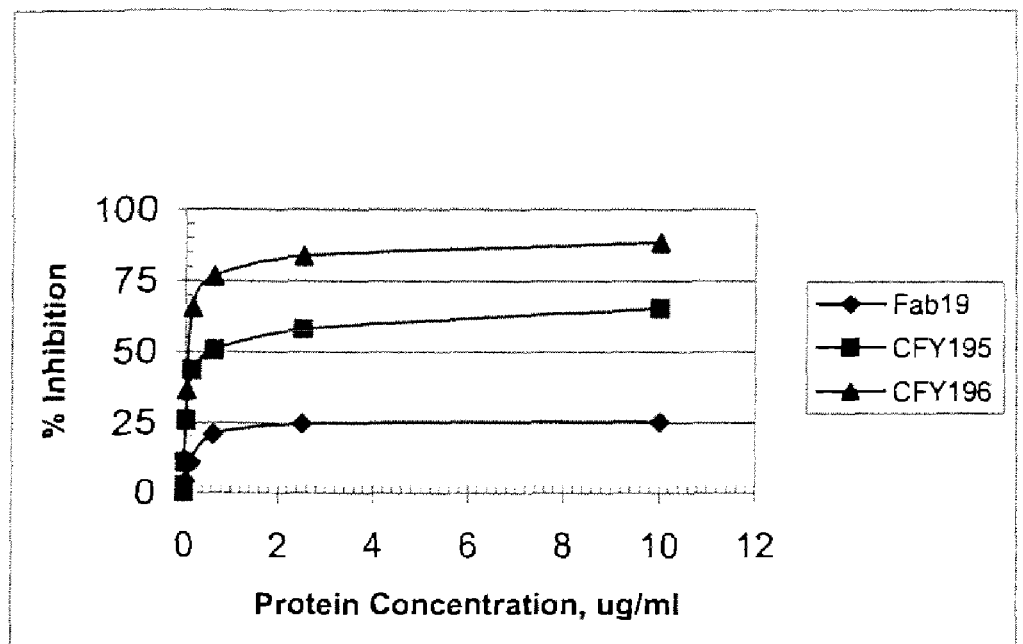
FIG. 8 shows the results of a competition ELISA. The data is presented as a percent of inhibition of tracer antibody binding to ICAM-1.

FIG. 8 shows that monomeric Fab (Fab19) only inhibits 25% tracer antibody (TGC-HRP) binding at the highest concentration tested. However, its trimer (Fab19-EDATFα-II) or its tetramer (Fab19-EDATFα-LI) gave a much higher percentage inhibition. The IC$_{50}$ for these three molecules are as follows:

| Samples | IC$_{50}$ (µg/ml) |
|---|---|
| Fab19 | below IC$_{50}$ |
| Fab19-EDATFα-II | 0.54 |
| Fab19-EDATF(1)α-LI + S | 0.069 |

Example 14

This example describes additional applications of the invention multimer polypeptides.

Multimers may be used in any context where greater binding affinity or multivalent binding is desired. The only requirement is the availability of a moiety that can be adapted for use in the construction of a chimeric protein of the invention. The moiety may be a binding protein or any synthetic or natural molecule that can be coupled by a chemical bond to form the chimera. Examples of such moieties include chelators, binding peptides, binding proteins, and the like.

Multimeric molecules of the invention could be used for various environmental applications. For example, invention multimers that bound heavy metals or toxins could be used in bioremediation. Multimers that bound a protein on the surface of a pathogen can be used to neutralize that pathogen in the environment, for example, in a field where cattle graze.

Multimers of the invention can also be constructed that act as insecticides or herbicides free of the unintended toxicity of many small molecules.

Multimeric molecules of the invention can also have industrial applications. For example, a multimer could be used in industrial chemistry to either remove a product of a reaction, thus speeding the reaction or driving it to completion, or to remove a reactant or catalyst, thus stopping a reaction. In addition, multimeric molecules can be used to recover substances from dilute solutions. Furthermore, bispecific molecules can be constructed from two successive enzymes in a synthetic pathway in order to increase the reaction rate for the combined steps.

Example 15

This example describes additional kinds of multimeric peptide-based drugs that can be made in accordance with the invention.

Binding molecules, such as antibodies against a target can be identified by any means known in the art. For example, CDR regions of an antibody that binds to a target of interest can be transferred to a humanized framework using methods known in the art. The humanized antibody can optionally be expressed as either ScFv or Fab fragments as part of a chimeric multimeric protein. Particular non-limiting examples of target proteins of interest along with an indication of the medical condition that can be treated by binding of a multimeric protein to the target:

Beta tryptase (allergy, inflammation)
LFA-1 (transplant rejection)
CD105, VEGF (macular degeneration, cancer)
IgE (asthma)
CD154 (lupus, transplant rejection)
CD14 (sepsis)
Folate receptor alpha (filovirus infection, e.g., Ebola and Marburg viruses)
nectin-1, also known as CD111-(human herpesviruses)
gp120 (HIV-1/AIDS)
IL-6 (arthritis)
IL-5 (asthma)
IL-8 (general inflammation)
or any other interleukin (general inflammation)
Any growth factor receptor (cancer)

In addition, therapeutic antibodies already developed could be enhanced by application of this invention. Examples include:
anti-von Willebrand factor (coronary thrombosis)
anti-TNF alpha (Crohn's disease)
anti-Her-2 (breast cancer)
anti-CD-3 (transplant rejection)
anti-CD-20 (non Hodgkin's lymphoma)

SEQUENCE LISTING

The present specification is being filed with a computer readable form (CRF) copy of the Sequence Listing. The CRF entitled 13189-012-999SEQLIST.txt, which was created on Oct. 11, 2012 and is 48,620 bytes in size, is identical to the paper copy of the Sequence Listing and is incorporated herein by reference in its entirety.

What is claimed is:

1. A multimerization polypeptide comprising an amino acid sequence selected from the group consisting of (i) SEQ ID NO: 154; and (ii) SEQ ID NO: 154, wherein one or more of amino acid positions 1, 4, 8, 11, 15, 18, 22, 25, and 29 is substituted with leucine, isoleucine, or valine.

2. The multimerization polypeptide of claim 1, wherein the polypeptide comprises the amino acid sequence of SEQ ID NO: 154.

3. The multimerization polypeptide of claim 1, wherein the polypeptide comprises the amino acid sequence of SEQ ID NO: 154, wherein one or more of amino acid positions 1, 4, 8, 11, 15, 18, 22, 25, and 29 is substituted with leucine, isoleucine, or valine.

4. The multimerization polypeptide of claim 2, wherein the polypeptide consists of the amino acid sequence of SEQ ID NO: 154.

5. The multimerization polypeptide of claim 4, wherein the polypeptide consists of the amino acid sequence of SEQ ID NO: 154, wherein one or more of amino acid positions 1, 4, 8, 11, 15, 18, 22, 25, and 29 is substituted with leucine, isoleucine, or valine.

6. A chimeric protein comprising a heterologous polypeptide fused to the N-terminus of the multimerization polypeptide of claim 1.

7. The chimeric protein of claim 6, wherein the heterologous polypeptide is selected from the group consisting of a binding protein, enzyme, receptor, ligand, nucleic acid binding protein, growth regulatory factor, differentiative factor, and chemotactic factor.

8. The chimeric protein of claim 7, wherein the binding protein comprises an antigen binding polypeptide.

9. The chimeric protein of claim 8, wherein the antigen binding polypeptide comprises at least one antibody variable domain.

10. The chimeric protein of claim 9, wherein the antibody variable domain is human or humanized.

11. The chimeric protein of claim 8, wherein the antigen binding polypeptide comprises a single chain antibody, Fab, Fab', (Fab')$_2$, or Fv antibody subsequence.

12. The chimeric protein of claim 8, wherein the antigen binding polypeptide comprises a multispecific or multifunctional antibody.

13. The chimeric protein of claim 8, wherein the antigen binding polypeptide binds to ICAM-1 or an epitope thereof.

14. The chimeric protein of claim 6, wherein said chimeric protein contains a linker between the heterologous polypeptide and multimerization polypeptide.

15. The chimeric protein of claim 14, wherein the linker comprises a hinge domain.

16. The chimeric protein of claim 14, wherein the linker comprises an amino acid sequence set forth in any of SEQ ID NO: 43, SEQ ID NO: 44, SEQ ID NO: 45, SEQ ID NO: 46 or SEQ ID NO: 47.

17. The chimeric protein of claim 14, wherein the linker comprises an amino acid sequence having a length of from about 5 to 20 amino acids.

18. The chimeric protein of claim 14, wherein the linker comprises an amino acid sequence having a length of from about 10 to 30 amino acids.

19. The chimeric protein of claim 14, wherein the linker comprises an amino acid sequence having a length of from about 25 to 50 amino acids.

20. The chimeric protein of claim 14, wherein the linker comprises an amino acid sequence having a length of from about 30 to 60 amino acids.

21. The chimeric protein of claim 14, wherein the linker comprises an amino acid sequence having a length of from about 50 to 75 amino acids.

22. A polypeptide oligomer comprising at least two chimeric proteins of claim 6.

23. The polypeptide oligomer of claim 22 that is a tetramer.

24. The polypeptide oligomer of claim 23 that is homomeric tetramer.

25. A pharmaceutical formulation comprising the chimeric protein of claim 6 and a pharmaceutical carrier.

26. The pharmaceutical formulation of claim 25, wherein the pharmaceutical carrier is a sterile, aqueous solution.

27. The pharmaceutical formulation of claim 26, wherein the pharmaceutical carrier is an ointment, salve, gel, or cream.

28. A kit comprising the pharmaceutical formulation of claim 26 in a container.

29. The kit of claim 28, further comprising instructions for administration of the pharmaceutical formulation.

\* \* \* \* \*